US009561064B2

(12) United States Patent
Goodwin et al.

(10) Patent No.: US 9,561,064 B2
(45) Date of Patent: Feb. 7, 2017

(54) BONE PLATE SYSTEM AND METHOD

(71) Applicants: Robert Goodwin, Marquette, MI (US); Peter Didyk, Marquette, MI (US); Jamie Close, Chocolay Township, MI (US); Matthew Gephart, Marquette, MI (US)

(72) Inventors: Robert Goodwin, Marquette, MI (US); Peter Didyk, Marquette, MI (US); Jamie Close, Chocolay Township, MI (US); Matthew Gephart, Marquette, MI (US)

(73) Assignee: PIONEER SURGICAL TECHNOLOGY, INC., Marquette, MI (US)

( * ) Notice: Subject to any disclaimer, the term of this patent is extended or adjusted under 35 U.S.C. 154(b) by 94 days.

(21) Appl. No.: 13/837,615

(22) Filed: Mar. 15, 2013

(65) Prior Publication Data

US 2014/0142638 A1     May 22, 2014

Related U.S. Application Data

(60) Provisional application No. 61/728,930, filed on Nov. 21, 2012.

(51) Int. Cl.
*A61B 17/80*     (2006.01)
*A61B 17/82*     (2006.01)
(Continued)

(52) U.S. Cl.
CPC ......... *A61B 17/8869* (2013.01); *A61B 17/808* (2013.01); *A61B 17/8076* (2013.01);
(Continued)

(58) Field of Classification Search
CPC ... A61B 17/82; A61B 17/823; A61B 17/8076; A61B 17/808; A61B 17/8057; A61B 17/842; A61B 17/8033–17/8047; A61B 17/08; A61B 17/083; A61B 17/085; A61B 2017/081; A61B 2017/086; A61B 2017/088; A61B 2017/0446
(Continued)

(56) References Cited

U.S. PATENT DOCUMENTS

| 1,988,534 A | 1/1935 | Abbott |
| 2,002,977 A | 5/1935 | Carr |

(Continued)

FOREIGN PATENT DOCUMENTS

| AU | 743254 B | 1/2002 |
| CN | 201260694 Y | 6/2009 |

(Continued)

OTHER PUBLICATIONS

Ease of Wire with the Stability of a Plate, AcuTie Sternal Closure System, 12 pages, Oct. 2010.

(Continued)

*Primary Examiner* — Todd E Manahan
*Assistant Examiner* — Marcela I Shirsat
(74) *Attorney, Agent, or Firm* — Fitch, Even, Tabin & Flannery LLP

(57) ABSTRACT

A bone plate system for securing a plurality of bones is provided including a plate member, a locking device of the bone plate, and a surgical cable having a trailing end for being connected to the bone plate and a leading end for being advanced around the bones and into the locking device. The surgical cable may be tensioned to approximate the bones, urge the bones together, and seat the bone plate against the bones. The locking device may be reconfigured to a locked configuration to fix the bone plate to the surgical cable. The bone plate further includes a plurality of through-bores for receiving bone anchors that rigidly fix the bone (Continued)

plate to the bones. The bone plate system utilizes the tensile strength of the surgical cable and the rigid fixation between the bone anchors and the bone plate to resist relative movement of the bones.

53 Claims, 73 Drawing Sheets

(51) Int. Cl.
    A61B 17/88    (2006.01)
    A61B 17/84    (2006.01)
    B60P 7/08    (2006.01)
    A61B 17/68    (2006.01)

(52) U.S. Cl.
    CPC .......... *A61B 17/823* (2013.01); *A61B 17/842* (2013.01); *A61B 17/8057* (2013.01); *A61B 2017/681* (2013.01); *B60P 7/083* (2013.01); *B60P 7/0823* (2013.01); *B60P 7/0838* (2013.01)

(58) Field of Classification Search
    USPC ............ 606/213–231, 70–71, 280–299, 902, 232,606/233, 74, 103, 138–150; 24/527; 623/13.13, 623/13.14
    See application file for complete search history.

(56) References Cited

U.S. PATENT DOCUMENTS

| | | | |
|---|---|---|---|
| 2,557,877 A | 6/1951 | Kluson | |
| 3,959,960 A | 6/1976 | Santos | |
| 4,050,464 A | 9/1977 | Hall | |
| 4,269,180 A * | 5/1981 | Dall | A61B 17/0642 606/281 |
| 4,327,715 A | 5/1982 | Corvisier | |
| 4,583,541 A | 4/1986 | Barry | |
| 4,959,065 A | 9/1990 | Arnett et al. | |
| 5,015,248 A | 5/1991 | Burstein | |
| 5,139,498 A * | 8/1992 | Astudillo Ley | A61B 17/8076 606/216 |
| 5,312,410 A | 5/1994 | Miller et al. | |
| 5,395,374 A | 3/1995 | Miller et al. | |
| 5,415,658 A | 5/1995 | Kilpela et al. | |
| 5,449,361 A | 9/1995 | Preissman | |
| 5,456,722 A | 10/1995 | McLeod et al. | |
| 5,522,827 A | 6/1996 | Combs et al. | |
| 5,536,270 A | 7/1996 | Songer et al. | |
| 5,568,865 A | 10/1996 | Mase et al. | |
| 5,569,253 A | 10/1996 | Farris et al. | |
| 5,578,057 A | 11/1996 | Wenstrom | |
| 5,660,091 A | 8/1997 | Stone et al. | |
| 5,702,399 A | 12/1997 | Kilpela et al. | |
| 5,752,959 A | 5/1998 | Korhonen | |
| 5,810,825 A | 9/1998 | Huebner | |
| 5,849,012 A | 12/1998 | Abboudi | |
| 5,902,305 A | 5/1999 | Beger et al. | |
| 5,935,130 A | 8/1999 | Kilpela et al. | |
| 5,935,133 A | 8/1999 | Wagner et al. | |
| 6,017,347 A | 1/2000 | Huebner et al. | |
| 6,077,268 A | 6/2000 | Farris et al. | |
| 6,086,590 A | 7/2000 | Margulies et al. | |
| 6,099,527 A | 8/2000 | Hochschuler et al. | |
| 6,120,506 A | 9/2000 | Kohrs et al. | |
| 6,123,709 A * | 9/2000 | Jones | 606/281 |
| 6,277,120 B1 | 8/2001 | Lawson | |
| 6,378,289 B1 | 4/2002 | Trudeau et al. | |
| 6,387,099 B1 | 5/2002 | Lange et al. | |
| 6,398,787 B1 | 6/2002 | Itoman | |
| 6,454,770 B1 * | 9/2002 | Klaue | 606/281 |
| 6,475,220 B1 | 11/2002 | Whiteside | |
| 6,520,965 B2 | 2/2003 | Chervitz et al. | |
| 6,605,091 B1 | 8/2003 | Iwanski | |
| 6,629,975 B1 | 10/2003 | Kilpela et al. | |
| 6,730,091 B1 | 5/2004 | Pfefferle et al. | |
| 6,832,532 B2 | 12/2004 | Kilpela et al. | |
| 6,872,210 B2 | 3/2005 | Hearn | |
| 7,052,499 B2 | 5/2006 | Steger et al. | |
| 7,156,847 B2 | 1/2007 | Abramson | |
| 7,207,993 B1 | 4/2007 | Baldwin et al. | |
| 7,229,444 B2 | 6/2007 | Boyd | |
| 7,250,054 B2 | 7/2007 | Allen et al. | |
| 7,494,461 B2 | 2/2009 | Wells et al. | |
| 7,635,365 B2 | 12/2009 | Ellis | |
| 7,695,501 B2 | 4/2010 | Ellis | |
| 7,785,355 B2 | 8/2010 | Mohr | |
| 7,803,176 B2 | 9/2010 | Teague et al. | |
| 8,282,675 B2 | 10/2012 | Maguire et al. | |
| 8,298,247 B2 | 10/2012 | Sterrett | |
| 8,313,517 B2 | 11/2012 | Mohr | |
| 8,337,497 B2 | 12/2012 | Deslauriers et al. | |
| 8,372,123 B2 | 2/2013 | Smisson, III et al. | |
| 8,460,295 B2 | 6/2013 | McClellan et al. | |
| 8,460,345 B2 | 6/2013 | Steger et al. | |
| 8,984,720 B2 | 3/2015 | Gephart | |
| 9,265,543 B2 | 2/2016 | Gephart | |
| 2002/0072753 A1 | 6/2002 | Cohen | |
| 2002/0177861 A1 | 11/2002 | Sugiyama et al. | |
| 2004/0138666 A1 | 7/2004 | Molz et al. | |
| 2004/0199169 A1 | 10/2004 | Koons et al. | |
| 2005/0171547 A1 | 8/2005 | Aram | |
| 2005/0177179 A1 | 8/2005 | Baynham et al. | |
| 2006/0089646 A1 | 4/2006 | Bonutti | |
| 2006/0167464 A1 | 7/2006 | Allen et al. | |
| 2006/0271060 A1 | 11/2006 | Gordon | |
| 2007/0225715 A1 | 9/2007 | Deffenbaugh | |
| 2008/0195145 A1 | 8/2008 | Bonutti et al. | |
| 2008/0275477 A1 | 11/2008 | Sterrett et al. | |
| 2008/0287951 A1 | 11/2008 | Stoneburner et al. | |
| 2009/0043316 A1 | 2/2009 | Durgin et al. | |
| 2009/0054933 A1 | 2/2009 | Mickiewicz et al. | |
| 2009/0069812 A1 | 3/2009 | Gillard | |
| 2009/0069851 A1 | 3/2009 | Gillard et al. | |
| 2009/0105717 A1 | 4/2009 | Bluechel | |
| 2009/0171402 A1 | 7/2009 | Dell'Oca | |
| 2010/0042106 A1 | 2/2010 | Bryant et al. | |
| 2010/0057091 A1 | 3/2010 | Oosterom | |
| 2010/0094294 A1 | 4/2010 | Gillard et al. | |
| 2010/0094362 A1 | 4/2010 | Lutze et al. | |
| 2010/0179595 A1 | 7/2010 | Bao et al. | |
| 2010/0305571 A1 | 12/2010 | Pratt et al. | |
| 2010/0318137 A1 | 12/2010 | Stucki et al. | |
| 2010/0331844 A1 | 12/2010 | Ellis | |
| 2010/0331892 A1 | 12/2010 | Fell | |
| 2011/0112537 A1 | 5/2011 | Bernstein et al. | |
| 2011/0218580 A1 | 9/2011 | Schwager et al. | |
| 2012/0089193 A1 * | 4/2012 | Stone et al. | 606/301 |
| 2012/0215224 A1 | 8/2012 | Songer | |
| 2012/0226321 A1 | 9/2012 | Gonzalez-Hernandez | |
| 2012/0303065 A1 | 11/2012 | Larroque-Lahitette | |
| 2013/0167334 A1 | 7/2013 | Gephart | |
| 2013/0289564 A1 | 10/2013 | Bernstein et al. | |
| 2014/0142638 A1 | 5/2014 | Goodwin | |

FOREIGN PATENT DOCUMENTS

| | | |
|---|---|---|
| TW | 314764 Y | 9/1997 |
| WO | 9428812 | 12/1994 |
| WO | 01/49191 A1 | 7/2001 |
| WO | 0234120 A2 | 5/2002 |
| WO | 2006088452 A | 8/2006 |
| WO | 2011/041624 A1 | 4/2011 |
| WO | 2011/116364 A1 | 9/2011 |
| WO | 2013003719 A1 | 1/2013 |

OTHER PUBLICATIONS

SternaLock Blu Primary Closure System, Biomet Microfixation, Form No. BMF00-3265, Rev 05k1110, 10 pages, 2011.
Acute Innovation-Quick and Easy Installation & Re-entry, Acute Innovation, LLC, http://www.acuteinnovations.com/products/

(56) References Cited

OTHER PUBLICATIONS

AcuTie/Installtion, 7 pages, May 16, 2012.
Re-Entry Options, AcuTie Sternal Closure System, 1 page, accessed May 16, 2012.
Technique Guide, Modular Sternal Cable System Flexibility and Strength in Sternal Closure and Repair, Synthes CMF, 39 pages, Jul. 2008.
Technique Guide, Titanium Sternal Fixation System for Stable Internal Fixation of the Sternum, Synthes, Inc., 36 pages, Oct. 2010.
International Search Report and Written Opinion for corresponding International Application No. PCT/US13/68725, dated Apr. 4, 2014, 18 pages.
Search Report in corresponding Chinese Application No. 201380071031.X, dated Aug. 25, 2016, 3 pages.
First Office Action in corresponding Chinese Application No. 201380071031.X, dated Sep. 18, 2016, 14 pages.

\* cited by examiner

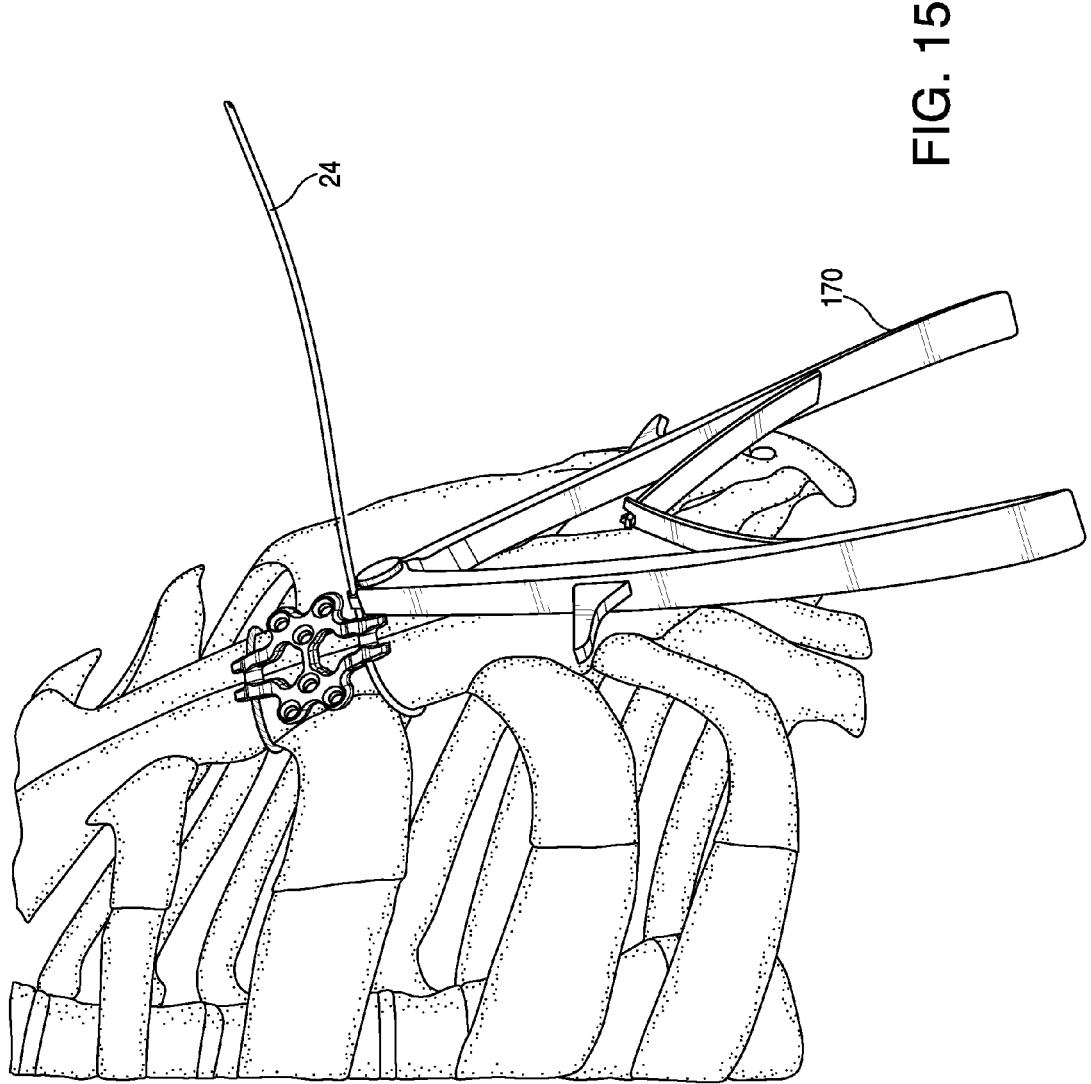

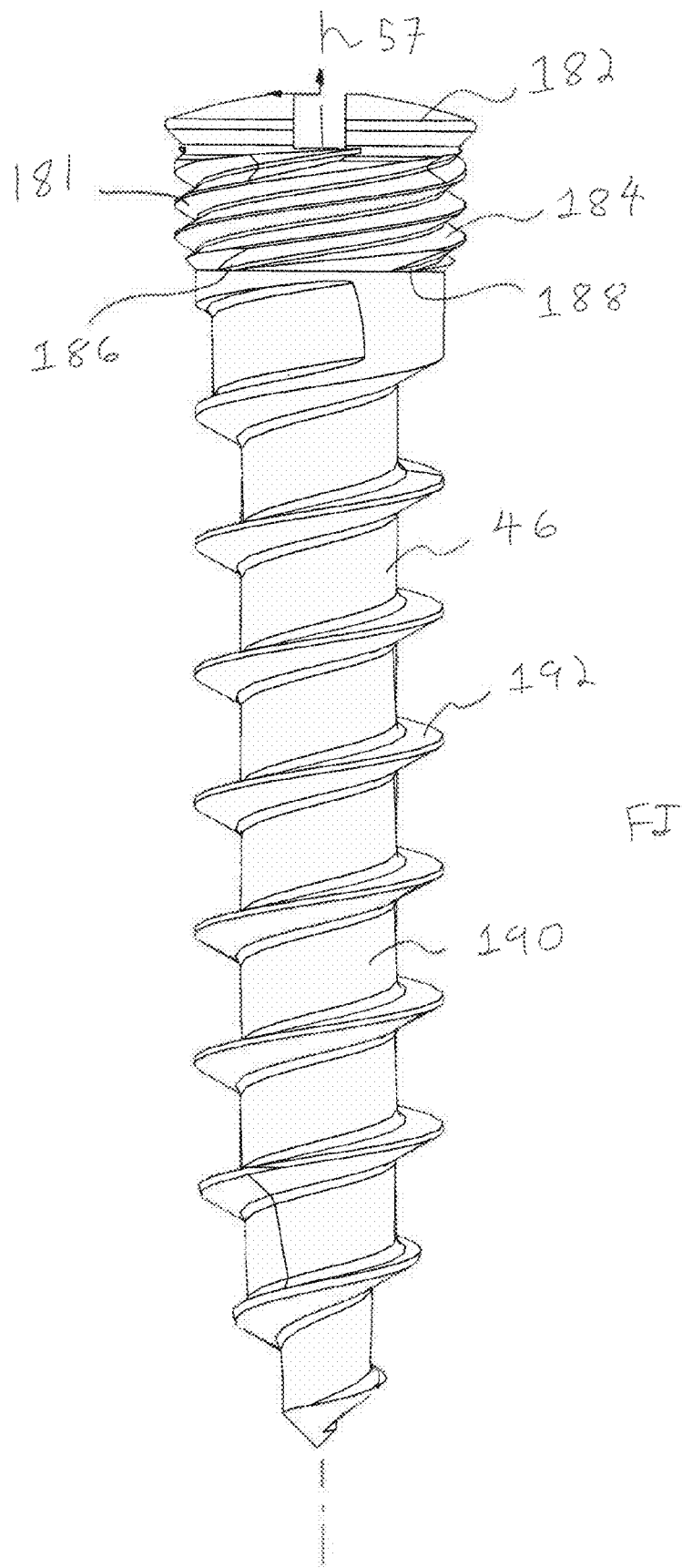

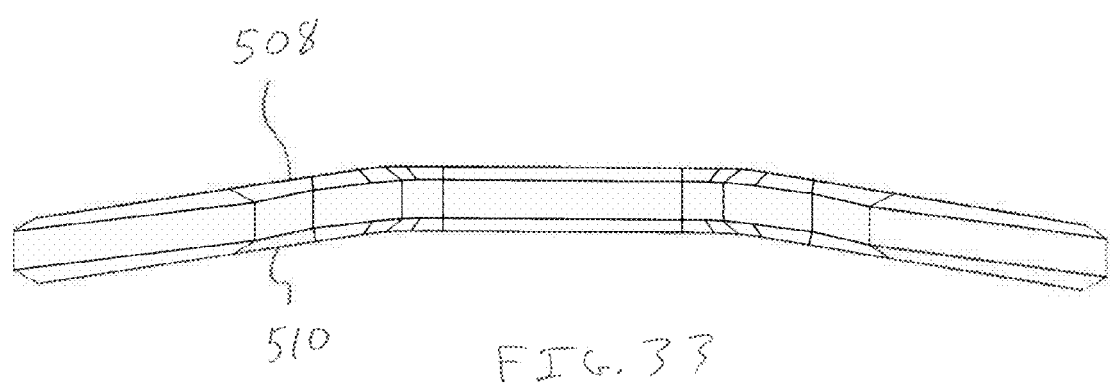

9,561,064 B2

BONE PLATE SYSTEM AND METHOD

CROSS-REFERENCE TO RELATED APPLICATION

The application claims the benefit of U.S. Patent Application No. 61/728,930 filed Nov. 21, 2012, which is hereby incorporated by reference in its entirety.

FIELD OF THE INVENTION

The invention relates to a bone plate system and, more particularly, to a bone plate system for securing and stabilizing a plurality of bones.

BACKGROUND OF THE INVENTION

There are presently many different types of plate and fixture systems for securing bones so that the secured bones may fuse or heal. As used herein, the term bone may refer to a bone or a portion of a bone. One application for plate and fixture systems is in the field of cardiovascular surgery, where access to a patient's heart may be obtained by cutting the sternum of the patient longitudinally from the manubrium through the xiphoid process. Cutting the sternum longitudinally creates halves of the sternum that may be separated to provide access to the chest cavity. After the patient's heart is operated upon, the sternal halves are brought back together and secured to one another. One approach for securing the sternal halves involves looping a metal wire around the sternal halves and twisting ends of the wire to secure the wire in tight engagement extending about the cut sternum bone halves. This process is repeated at several longitudinally spaced positions along the cut sternum in order to restrict separation and shifting of the sternal halves post-surgery. However, the twisted wires may loosen over time and permit relative movement of the sternal halves which adversely affects post-operative fusion of the sternal halves.

SUMMARY OF THE INVENTION

In accordance with one aspect, a bone plate system is provided for securing and stabilizing portions of one or more bones, such as halves of a sternum after the sternum has been cut longitudinally to provide access to an underlying chest cavity. The bone plate system includes a bone plate, a cable configured to be looped around the portions of the one or more bones and connected to the bone plate, and opposite halves of the bone plate that are laterally spaced apart from each other and which are configured for engaging a bone portion on either side of an incision that separates the bone portions. The bone plate has a locking device that interconnects and extends laterally between the spaced bone plate halves and resists relative movement therebetween. The locking device has an unlocked configuration that allows the cable to be shifted relative to the bone plate as tension is applied to the cable. Tensioning the cable tightly wraps the cable about the bone portions, approximates the bone portions together, and draws the bone plate tightly against the approximated bone portions to rapidly and efficiently produce a construct of the bone plate, cable, and approximated bone portions.

Once the cable has been tightened to a desired tension, the locking device of the bone plate may be reconfigured to a locked configuration which rigidly fixes the cable to the bone plate and secures the bone plate and cable about the bones. The bone plate halves include a plurality of throughbores for receiving bone anchors for anchoring the bone plate halves in engagement with the bone portions. In this manner, the bone plate system utilizes both the high tensile strength of the cable and the rigid fixation of the bone anchors to the bone plate to provide two load bearing mechanisms which resist separation and movement of the bone portions.

In accordance with another aspect, a method of securing and stabilizing a plurality of bone portions is provided. The method includes connecting a trailing end portion of a cable to a bone plate, positioning the bone plate adjacent the bone portions, advancing a leading end portion of the cable around the bones to form a loop of the cable around the bone portions, and connecting the leading end portion of the cable to the bone plate. In one form, connecting the cable to the bone plate includes advancing the leading end portion of the cable through an aperture of the bone plate sized so that there is a slip fit between the cable and the bone plate. The method further includes tightening the loop of cable around the bone portions to seat the bone plate against the bone portions. In one approach, tightening the loop of cable around the bone portions includes pulling the leading end portion of the cable away from the bone plate and urging the bone portions together. As the cable loop is tightened around the bone portions, the tension force acting along the surgical cable substantially simultaneously urges the bone portions together (if they are separated), draws the bone plate against the bone portions, and firmly seats the bone plate against the bone portions. The method further includes reconfiguring a locking device associated with the bone plate to a locked configuration to fix the locking device to the cable and secure the bone plate, cable, and bone portions to one another. In this manner, the method provides a rapid and straightforward approach for urging a plurality of bone portions together, seating a bone plate against the bone portions, and securing the bone plate, cable, and bone portions to one another.

The method further includes driving bone anchors through openings in the bone plate and into the bone portions to rigidly fix the bone plate to the bone portions. One advantage of using the cable to draw the bone plate against the bone portions and seat the bone plate against the bone portions is that the bone plate can be secured against the bone portions using the cable before the bone anchors are used to provide additional fixation of the bone plate to the bone portions. This may reduce shifting of the bone plate on the bone portions while driving the bone anchors through the openings in the bone plate. Another advantage of using the cable to draw the bone plate against the bone portions and seat the bone plate against the bone portions is that the bone plate may be firmly seated against the bone portions even if the bone portions are weakened, such as bones having a thin cortical section and/or voids between cortical sections. This approach stands in contrast to some prior fixation systems that exclusively utilize bone screws to seat a plate member against bones. If the bones are weakened, the bone screws of these prior fixation systems may not have sufficient purchase with the bones to draw the bone plate against the bones and fully seat the bone plate.

In another aspect, a bone plate system is provided for stabilizing portions of one or more bones that provides an easier-to-use approach for stabilizing the bone portions. The bone plate system includes a bone plate and a connector device having a flexible portion for being looped around the bone portions and secured to the bone plate. The bone plate has a deformable member with a throughbore configured to receive the connector device extending therethrough. The deformable member has exposed opposing crimp portions disposed across the throughbore from one another with the opposed crimp portions being configured to be deformed toward each other to fix the connector device to the bone plate. The exposed opposing crimp portions may thereby provide more secure and durable locking of the connector device to the bone plate than some conventional approaches that utilize a single stud to pinch a wire or cable against a channel wall.

The deformable member may be a cylindrical, tubular member and the crimp portions may be diametrically opposed from one another across the throughbore. The tubular member presents a less obtrusive profile than some prior approaches that utilize outwardly projecting locking members. This reduces the likelihood of tissues becoming pinched by or otherwise entangled with the features of the locking device.

In one form, the bone plate includes a pair of tool-receiving through openings on opposite sides of the deformable member. The tool-receiving through openings are sized to accommodate a user positioning a tool in the through openings, such as advancing jaws of a crimping tool into the through openings. One of the opposing crimp portions of the deformable member extend along one of the pair of bone plate through openings and the other crimp portion extends along the other of the pair of through openings. In this manner, the crimp portions of the deformable member are readily accessible to a tool advanced into the bone plate through openings so that the tool may be used to deform the deformable portions.

In another form, the bone plate includes a pair of elongated, spaced tool alignment members connected to the deformable member and extending generally parallel to one another on opposite sides of the deformable member. The tool alignment members define at least a portion of a tool-receiving through opening of the bone plate. The tool alignment members may be separated by a predetermined distance that is slightly larger than a width of a jaw of a crimping tool to provide the jaw with clearance to be inserted into the tool-receiving through opening. This cooperating configuration also aligns the jaws of the crimping tool with the crimp portions along the deformable member and ensures that the jaws of the crimping tool engage the crimp portions of the deformable member.

The bone plate system is especially advantageous for emergency reentry situations wherein the chest cavity must be accessed after utilizing the bone plate system to secure halves of a cut sternum together. Emergent reentry situations may include situations where the patient suffers a heart attack after installation of the bone plate system. Because the cable is disposed within the throughbore of the bone plate deformable member, cutting the deformable member cuts the deformable member and the cable in one step. This is especially advantageous when compared to prior systems with separate approximating wires and bone plates disposed along the cut sternum which may require separate tools for cutting the approximating wires and the bone plates. Separately cutting the approximating wires and the bone plates of these prior systems may increase the time it takes to gain access to the chest cavity of the patient in an emergent reentry situation.

In accordance with another aspect, an instrument for tensioning a surgical cable is provided. The tensioning device has a rotary tensioning device configured to have a cable wound thereon and a ratchet assembly that permits turning of the rotary tensioning device in a wind up direction and selectively resists turning of the rotary tensioning device in a pay out direction. By wrapping the surgical cable about the rotary tensioning device, the tensioning device can take up and tension a relatively long section of surgical cable. This approach stands in contrast to some prior surgical cable tensioning instruments that, in order to tension a cable, utilize a cable tensioning mechanism which linearly translates a cable locking mechanism secured to the cable. With these devices, the overall length of the device is directly proportional to the length of linear travel of the tensioning mechanism such that tensioning larger sections of cable requires a proportionally larger tensioning device.

The rotary tensioning device has gripping portions configured to shift relative to each other with turning of the rotary tensioning device. Specifically, turning the rotary tensioning device in the wind up direction shifts the rotary tensioning device form a pass through configuration that permits the cable to be drawn through the gripping portions to a gripped configuration that fixes the cable relative to the shifted gripping portions. In this manner, tension can be applied to the fixed cable by simply turning the rotary tensioning device in the wind up direction. Thus, the tensioning instrument provides an improvement over some conventional tensioning instruments that require a user to perform separate manual operations of locking the tensioning instrument to the cable and then applying tension to the cable, such as by using different handles of the instrument to perform the locking and tensioning operations.

In one form, the ratchet assembly has a tensioning configuration that permits a surgeon to incrementally rotate the rotary tensioning device in a wind up direction, wrap the cable about the rotary tensioning device, and apply tension to the cable. By permitting incremental tensioning of the cable, the surgeon receives tactile feedback as the cable is tensioned and may stop rotating the rotary tensioning device once the desired tension has been reached. At this point, the cable may be secured, for example, in a looped configuration around a pair of bone portions using a locking device of a bone plate as described in greater detail below. With the cable secured, the ratchet assembly may be reconfigured to a release configuration to permit the rotary tensioning device to rotate in the pay out direction and allow the tensioning device to be removed from the surgical cable.

The ratchet assembly may include a drive for turning the rotary tensioning device and a release mechanism having a release configuration that disengages the drive from the rotary tensioning device and a tensioning configuration that engages the drive to the rotary tensioning device. With the release mechanism in the engaged configuration, the drive is connected to the rotary drive device such that turning of the drive produces turning of the rotary tensioning device. With the release mechanism in the disengaged configuration, the rotary tensioning device can turn relative to the drive which allows the tensioning instrument to be removed from the cable, such as by pulling the tensioning instrument off of the surgical cable. Pulling the tensioning instrument off of the surgical cable turns the rotary tensioning device and causes the cable to be unwound from the rotary tensioning device. Further, because the drive is disengaged from the rotary tensioning device, turning of the rotary tensioning device due to unwinding of the cable therefrom generally does not produce movement of the drive which makes the tensioning instrument easier to handle as it is removed from the cable.

In another aspect, a method is provided for approximating and securing a plurality of bone portions using a cable and a tensioning instrument that is configured to quickly and easily tension the cable around the bone portions. The method includes positioning a trailing end portion of the cable and a locking device connected thereto adjacent one or more of the plurality of bone portions and advancing a leading end portion of the cable around the plurality of bone portions and into the locking device to form a loop of the cable around the bone portions. The method includes feeding the leading end portion of the cable through a distal end of the tensioning instrument, advancing the cable between gripping portions of a rotary tensioning device of the tensioning instrument, and outward though a proximal end of the tensioning instrument. Next, the tensioning instrument is shifted downward along the cable until the distal end of the tensioning instrument abuts the locking device. The leading end portion of the cable is then pulled away from the locking device to draw slack out of the cable.

The method further includes turning the rotary tensioning device to substantially simultaneously lock the rotary tensioning device to the cable and tension the cable. Turning the rotary tensioning device locks the cable to the rotary tensioning device by reconfiguring the gripping portions of the rotary tensioning device from a pass-through configuration that permits the cable to be advanced through the gripping portions to a gripped configuration which fixes the cable relative to the shifted gripping portions. Further, turning the rotary tensioning device tensions the cable by drawing a portion of the cable on a distal side of the rotary tensioning device onto the rotary tensioning device while the distal end of the tensioning instrument remains abutting the locking device. If the bone portions are separated, turning of the rotary tensioning device tensions the looped cable around the bone portions and approximates the bone portions together. The method further includes selectively locking the rotary position of the rotary tensioning device once the cable has been sufficiently tensioned in order to maintain the cable at the desired tension. The locking device of the cable may then be reconfigured to a locked configuration to secure the tightened loop of cable around the bone portions. In one form, turning the rotary tensioning device also draws a portion of the cable onto the rotary tensioning device from a proximal side of the rotary tensioning device. The tensioning device preferably has an interior cavity sized to accommodate relatively long lengths of cable being drawn onto the rotary tensioning device from both the distal and proximal sides of the rotary tensioning device. The method thereby provides a quick and elegant approach to tensioning and securing a cable around a plurality of bone portions and, in some applications, approximating the bone portions while tensioning the cable.

BRIEF DESCRIPTION OF THE DRAWINGS

FIGS. 9-16 illustrate a method of using the bone plate system of FIG. 1 to secure the halves of the cut sternum;

FIG. 17 is an elevational view of one of the bone screws of the bone plate system of FIG. 1 showing threads on both the head and shank of the bone screw;

FIG. 33 is an elevational view of the bone plate of FIG. 29 showing a generally convex upper surface and a generally concave lower surface of the bone plate;

FIGS. 37 and 38 are elevational views of the bone plate of FIG. 36 showing a generally convex upper surface of the bone plate and a generally concave lower surface of the bone plate;

FIG. 41 is an exploded perspective view of the tensioning device of FIG. 39;

DETAILED DESCRIPTION OF THE PREFERRED EMBODIMENTS

Figure 1:
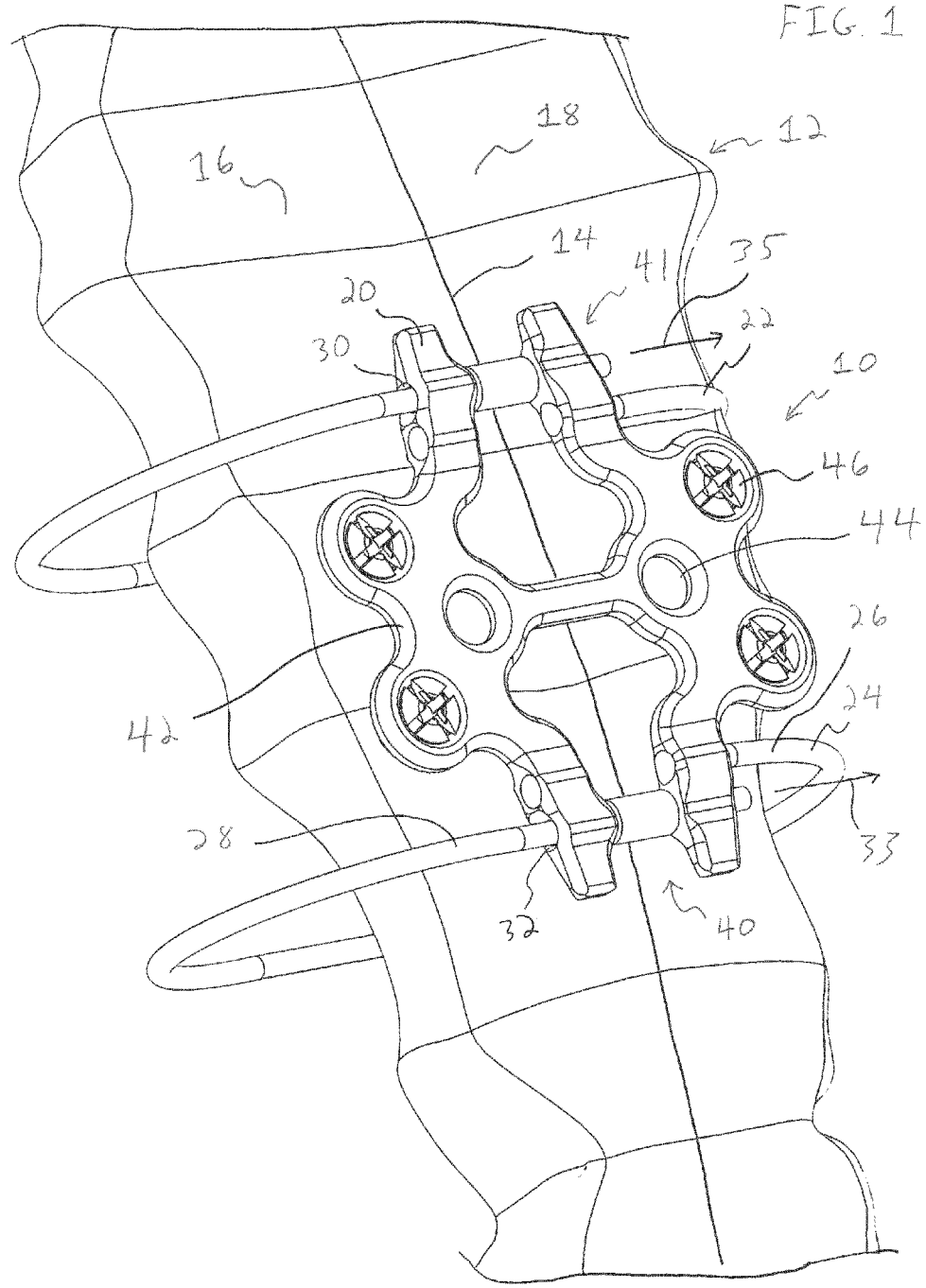
FIG. 1 is a perspective view of a bone plate system in accordance with the present invention positioned on a sternum that has been cut longitudinally.

Referring to FIG. 1, there is provided a bone plate system 10 for securing portions of one or more bones. In one approach, the bone plate system 10 is used to secure a sternum 12 that has been cut 14 into halves 16, 18 with the cut 14 extending longitudinally along the sternum 12. The bone plate system 10 includes a bone plate, such as plate member 20, and surgical cables 22, 24 configured to be advanced around the sternal halves 16, 18 and form loops 23, 25 (see FIG. 2) about the sternal halves 16, 18. Each surgical cable 22, 24 has a trailing end portion 26 connected to the bone plate 20 and a leading end portion 28 configured to be advanced around the sternal halves 16, 18 and into openings 30, 32 of the bone plate 20. The openings 30, 32 are sized to form a slip fit between the bone plate 20 and the surgical cables 22, 24. To tighten the loops of the cables 22, 24 about the sternal halves 16, 18, the bone plate 20 is held adjacent the sternal halves 16, 18 and the leading end portions 28 of the surgical cables 22, 24 are advanced in directions 33, 35. As the surgical cables 22, 24 tighten around the sternal halves 16, 18, the tension forces in the surgical cables 22, 24 urge the sternal halves 16, 18 together, draw the bone plate 20 against the sternal halves 16, 18, and firmly seat the bone plate 20 against the sternal halves 16, 18. The bone plate system 10 thereby allows rapid and substantially simultaneous approximation of the sternal halves 16, 18, drawing of the bone plate 20 toward the sternal halves 16, 18, and seating the bone plate 20 against the sternal halves 16, 18 as the surgical cables 22, 24 are tensioned about the sternal halves 16, 18.

The bone plate system 10 has a pair of locking devices 40, 41 disposed at opposite ends of the bone plate 20 for fixing the bone plate 20 to the surgical cables 22, 24. As discussed in greater detail below, after the leading end portions 28 of the surgical cables 22, 24 have been advanced through openings 30, 32 of the bone plate 20 and properly tensioned, the locking devices 40, 41 are reconfigured to a locked configuration to fix the bone plate 20 to the surgical cables 22, 24. The surgical cables 22, 24 have high tensile strength and, once looped around the sternal halves 16, 18 and fixed to the bone plate 20, serve as a primary load bearing mechanism that resists separation and relative movement of the sternal halves 16, 18. Thus, the bone plate system 10 provides a straightforward and easy-to-use apparatus for forming a secure construct of the sternal halves 16, 18, bone plate member 20, and surgical cables 22, 24.

The bone plate 20 has a body 42 extending along the length of the bone plate 20 between the locking devices 40, 41 that includes a plurality of throughbores 44 for receiving bone anchors, such as bone screws 46. The bone screws 46 are driven into the throughbores 44 and sternum 12 to fix the bone plate 20 to both halves 16, 18 of the sternum 12. With the bone screws 46 fully driven into the sternal halves 16, 18, the bone screws 46 provide anchor points to transmit loading from the sternal halves 16, 18 to the bone plate 20 and reinforce the sternum 12. In this manner, the bone plate system 10 utilizes the high tensile strength of the surgical cables 22, 24 extending tightly about the bone plate 20 as a primary load bearing mechanism and the rigid engagement between the screws 46 and the bone plate 20 as a secondary load bearing mechanism to resist to relative movement of the sternal halves 16, 18. By utilizing both load bearing mechanisms, the bone plate system 10 provides for load bearing between the primary load bearing cables 22, 24 and the secondary load bearing screws 46 with greater postoperative stability and fixation of the sternal halves 16, 18 than either load bearing mechanism on its own. As will be apparent, the bone plate system 10 may be used to secure and stabilize many different types of bones, bone fragments, and portions of bones. The bone plate system 10 may also be used to hold one or more medical implant devices, such as a splint, rod, graft, or the like, against one or more bones.

Figure 2:
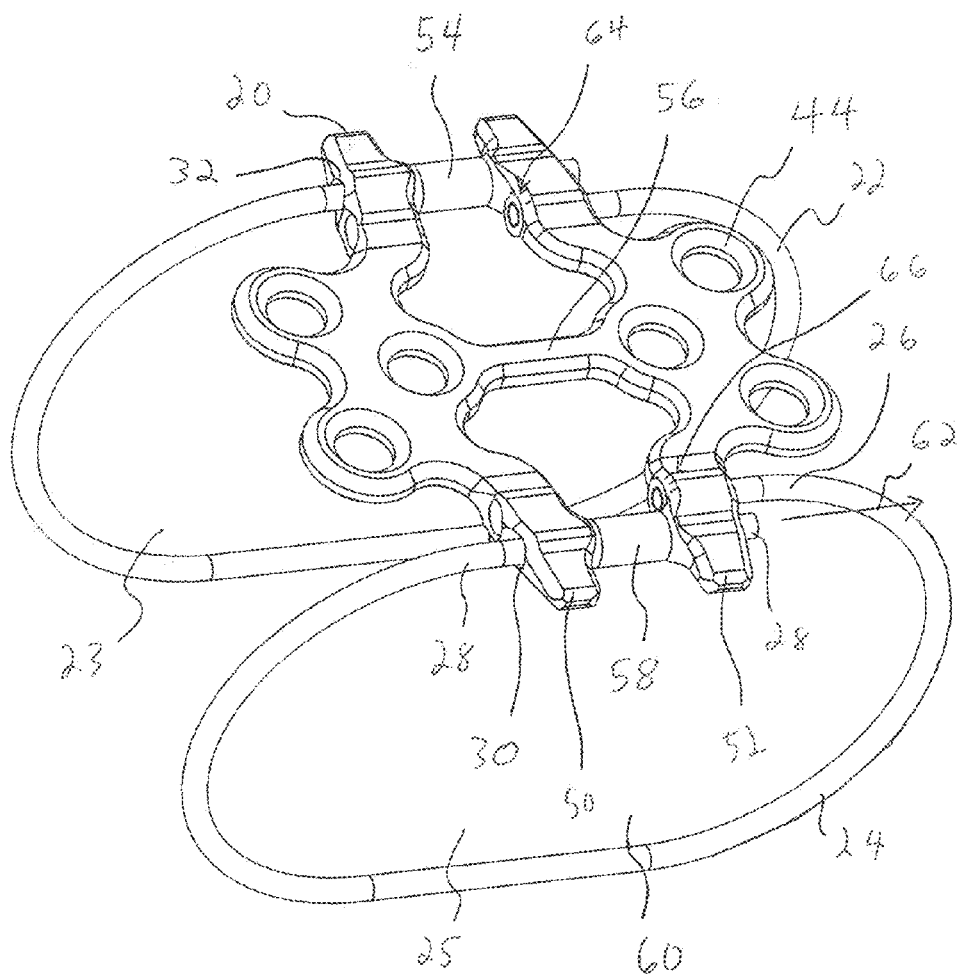
FIG. 2 is a perspective view of the bone plate system of FIG. 1 showing surgical cables of the bone plate system having opposite ends of the surgical cables connected to a plate member of the bone plate system.

With respect to FIG. 2, the bone plate 20 has a pair of tool alignment members, such as longitudinal members 50, 52, positioned on opposite side of the cut 14 (see FIG. 1) that extend along the length of the bone plate 20. Transverse supports 54, 56, 58 extend across the cut 14 between the longitudinal members 50, 52 and serve to interconnect and brace the longitudinal members 50, 52. The transverse supports 54, 56, 58 rigidly restrict lateral, rostral caudal, and anterior posterior movement of the longitudinal members 50, 52 and the sternal halves 16, 18 secured thereto.

Figure 3:
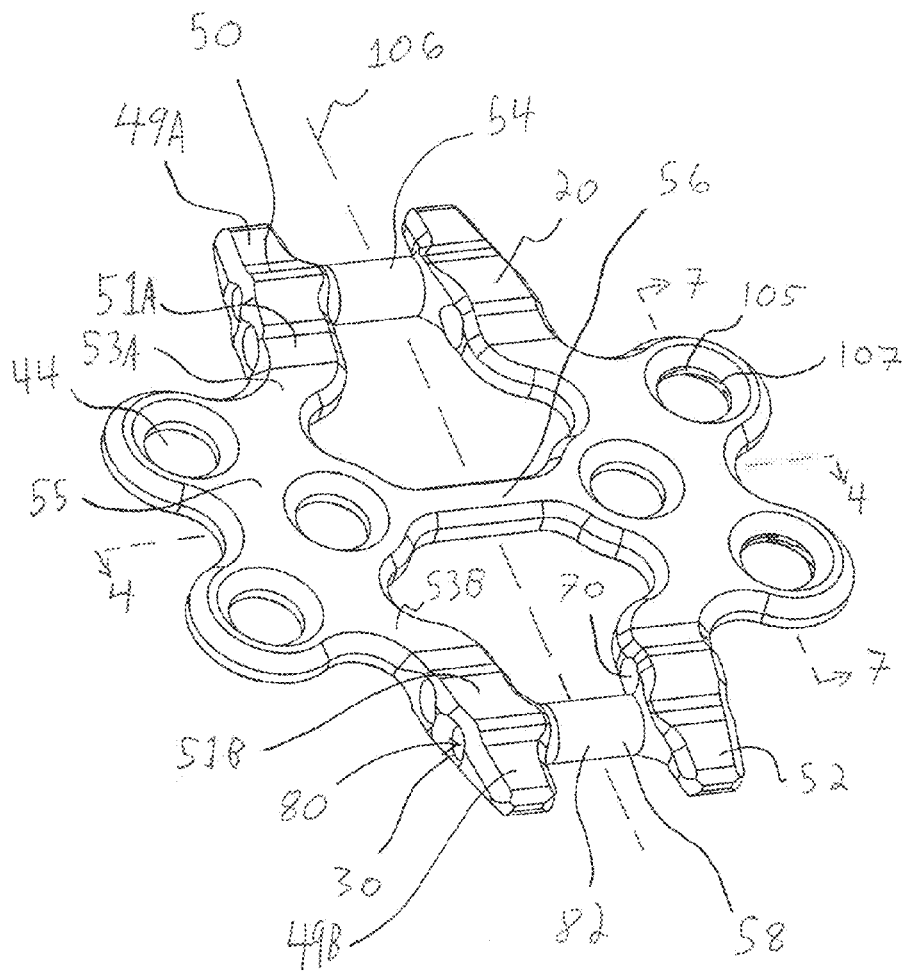
FIG. 3 is a perspective view of the bone plate of the bone plate system of FIG. 1 showing laterally spaced halves of the bone plate with throughbores therein for receiving bone anchors.
Figure 14:
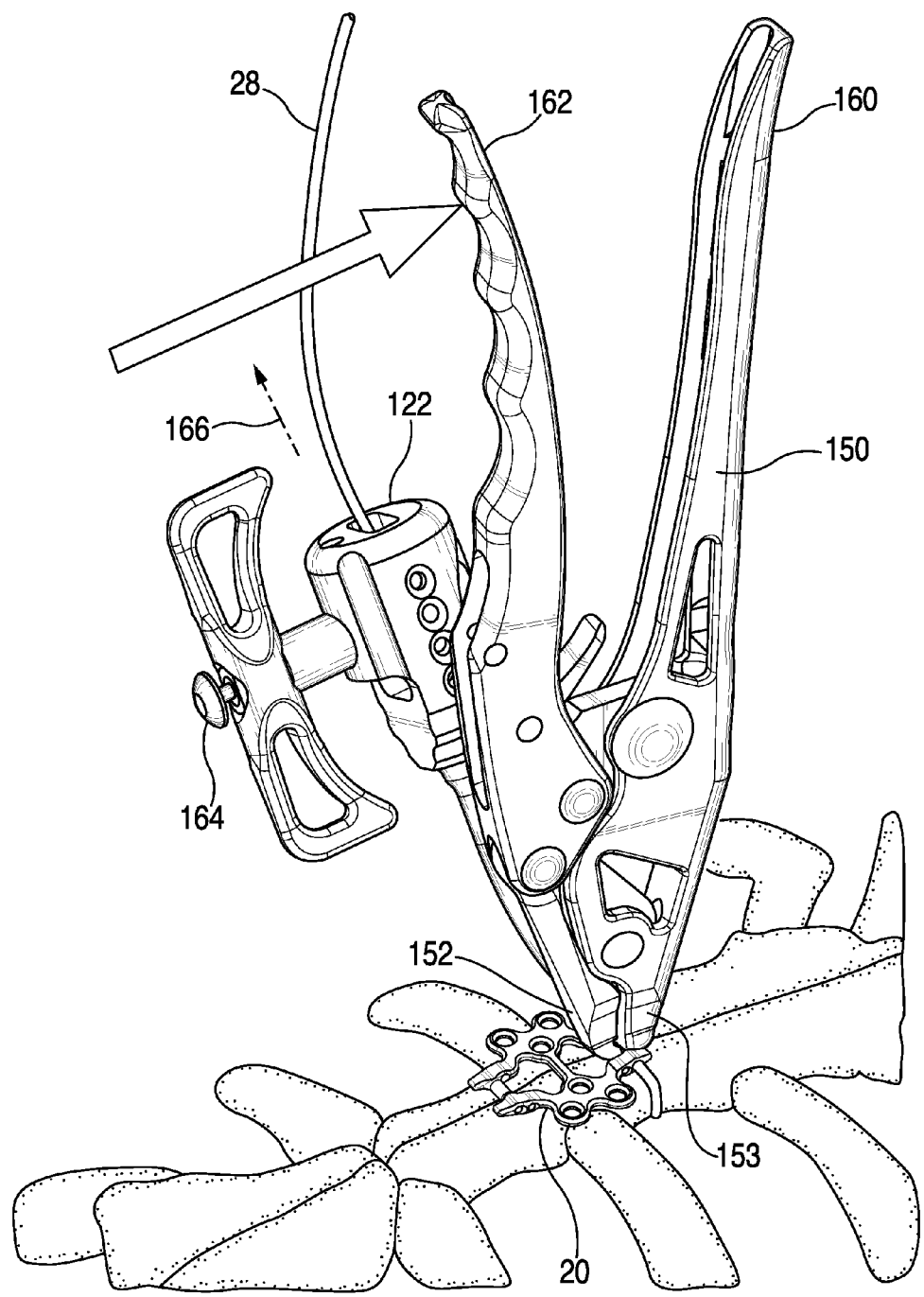
Figure 14A:
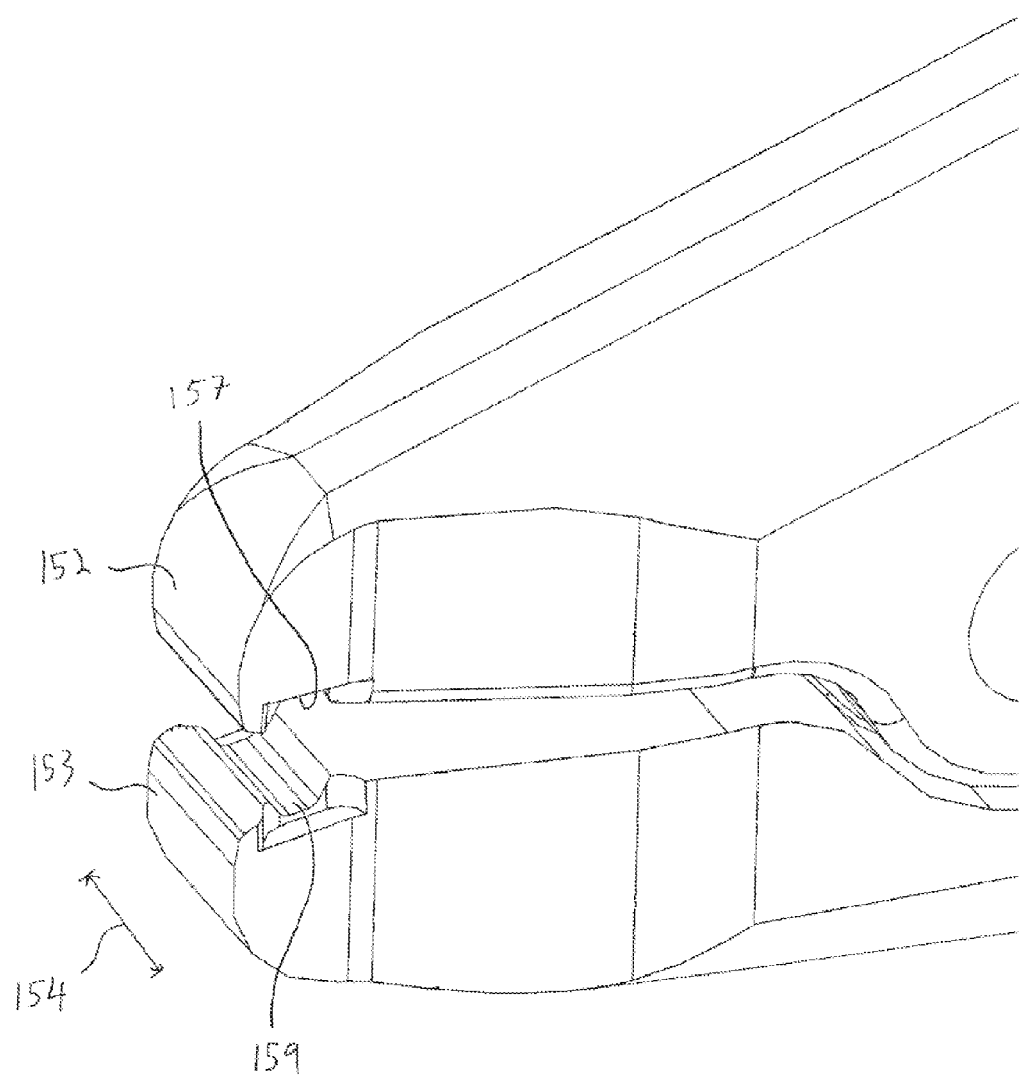
Figure 14B:
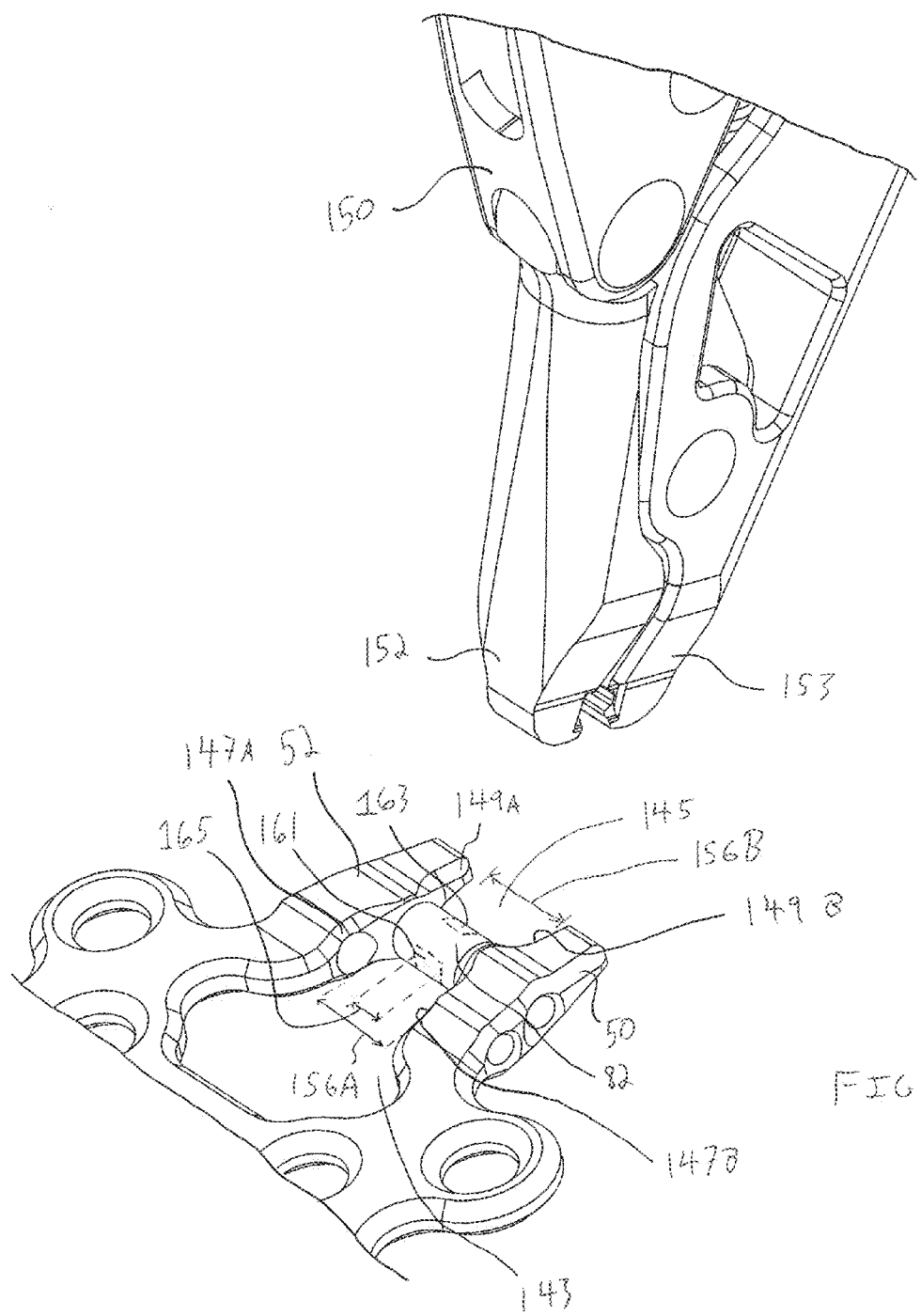

With reference to the longitudinal member 50 as shown in FIG. 3, each of the longitudinal members 50, 52 have portions 49A, 49B projecting beyond the transverse supports 54, 58 and along the sternal half 16 to increase the contact area between the bone plate 20 and the sternal half 16 along the cut 14 and further secure the bone plate 20 to the sternal half 16. The projecting portions 49A, 49B also serve to guide one of the jaws 152, 153 of a crimping tool 150 (see FIG. 14B) into an aligned position with the locking devices 40, 41, as will be discussed in greater detail below. Extending inward toward the center of the bone plate 20 are inner guide portions 51A, 51B of the longitudinal members 50, 52. The inner guide portions 51A, 51B serve to guide the other one of the jaws 152, 153 of the crimping tool 150 into an aligned position on the opposite side of the locking devices 40, 41. The longitudinal members 50, 52 further have angled portions 53A, 53B that bow outward from the inner guide portions 51A, 51B to laterally space halves of the bone plate 20, such as generally triangular lobes 55, outward from a central, longitudinal axis 106 of the bone plate 50. The lobes 55 have throughbores 44 formed therein such that positioning the lobes 55 outward from the longitudinal axis 106 positions longitudinal axes 57 (see FIG. 17) of the bone screws 46 away from the cut 14. This improves the engagement between the bone screws 46 and the sternal half 16 by keeping the bone screws 46 from splintering the bone adjacent the cut 14.

Figure 4:
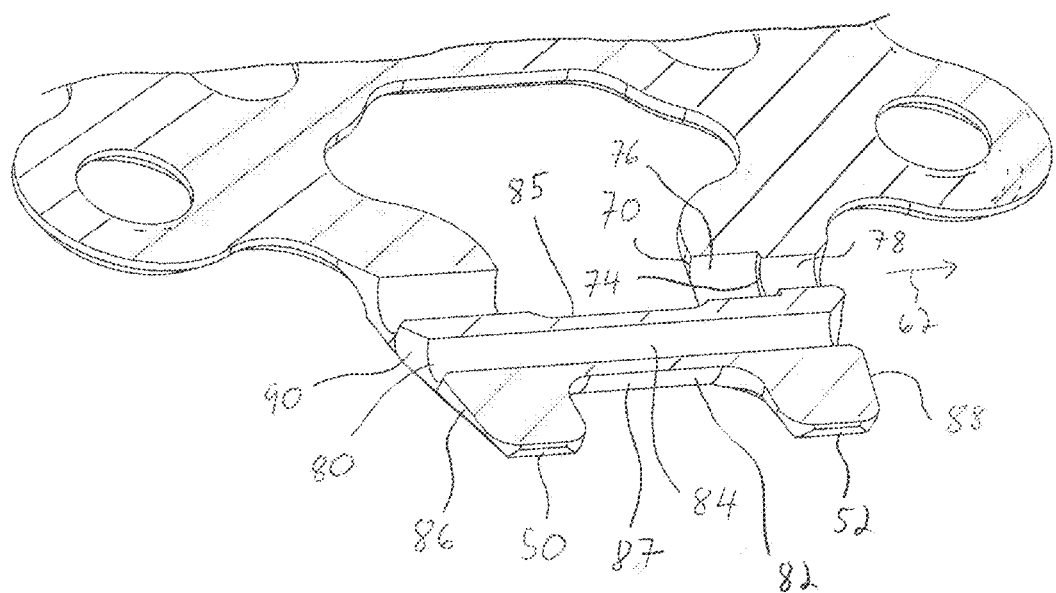
FIG. 4 is a cross sectional view taken across line 4-4 in FIG. 3 showing through apertures of the bone plate at one end thereof.
Figure 6:
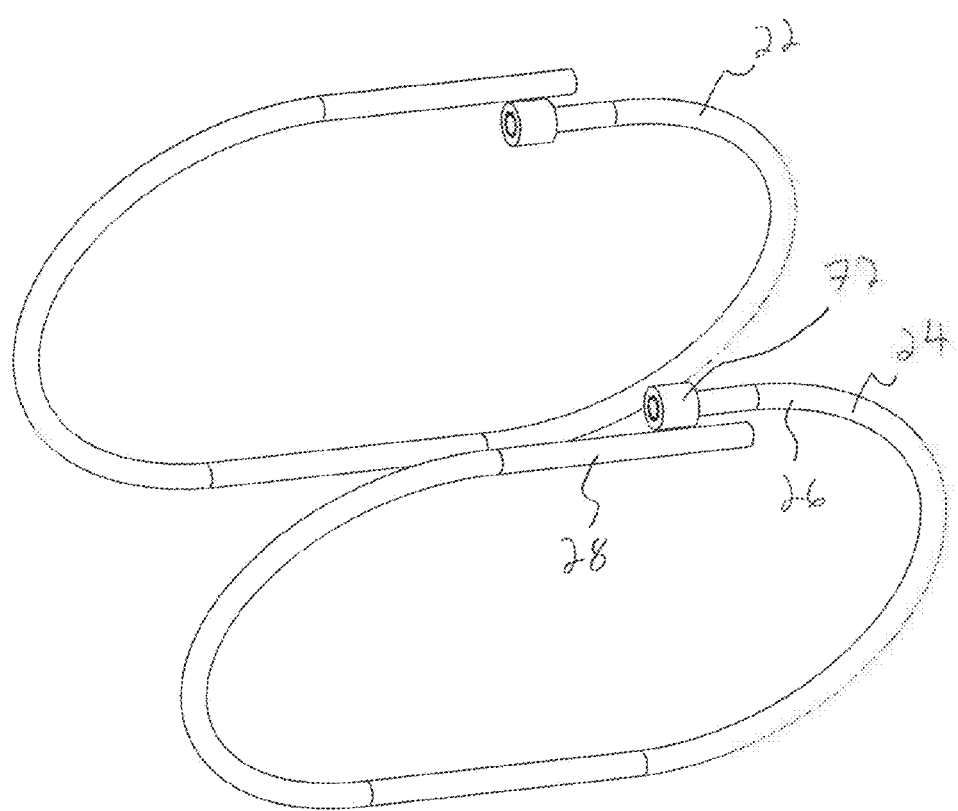
FIG. 6 is a perspective view of the surgical cables of the bone plate system of FIG. 1 showing plugs of the surgical cables that abut surfaces of the through apertures of the bone plate and restrict the surgical cables from passing through the apertures.

With reference to FIGS. 2-4, the bone plate system 10 includes connections 64, 66 between the trailing ends 26 of the surgical cables 22, 24 and the bone plate 20. The connections 64, 66 are similar and, as shown with respect to connection 66 and cable 24, each have a stop aperture 70 of the bone plate 20 sized to permit the leading end portion 28 of the surgical cable 24 to be advanced therethrough until an end plug 72 (see FIG. 6) of the trailing end portion 26 of the cable 24 enters the stop aperture 70 and abuts against an interior shoulder or annular surface 74 of the bone plate 20. As shown in FIG. 4, the stop aperture 70 includes a larger diameter portion 76 sized to permit the surgical cable 24 and the end plug 72 thereof to travel through the larger diameter portion 76 and abut the annular surface 74. The stop aperture 70 also has a smaller diameter portion 78 that includes the annular surface 74 and is configured to restrict the end plug 72 from advancing out of the stop aperture 70 in direction 62. The end plug 72 may be swedged onto the braided multi-stranded wires of the cable 24 or secured using, for example, welding. In an alternative form, the connections 64, 66 may have, for example, a press fit or weld between the trailing end portions 26 of the surgical cables 24, 26 and the bone plate 20.

Figure 5:
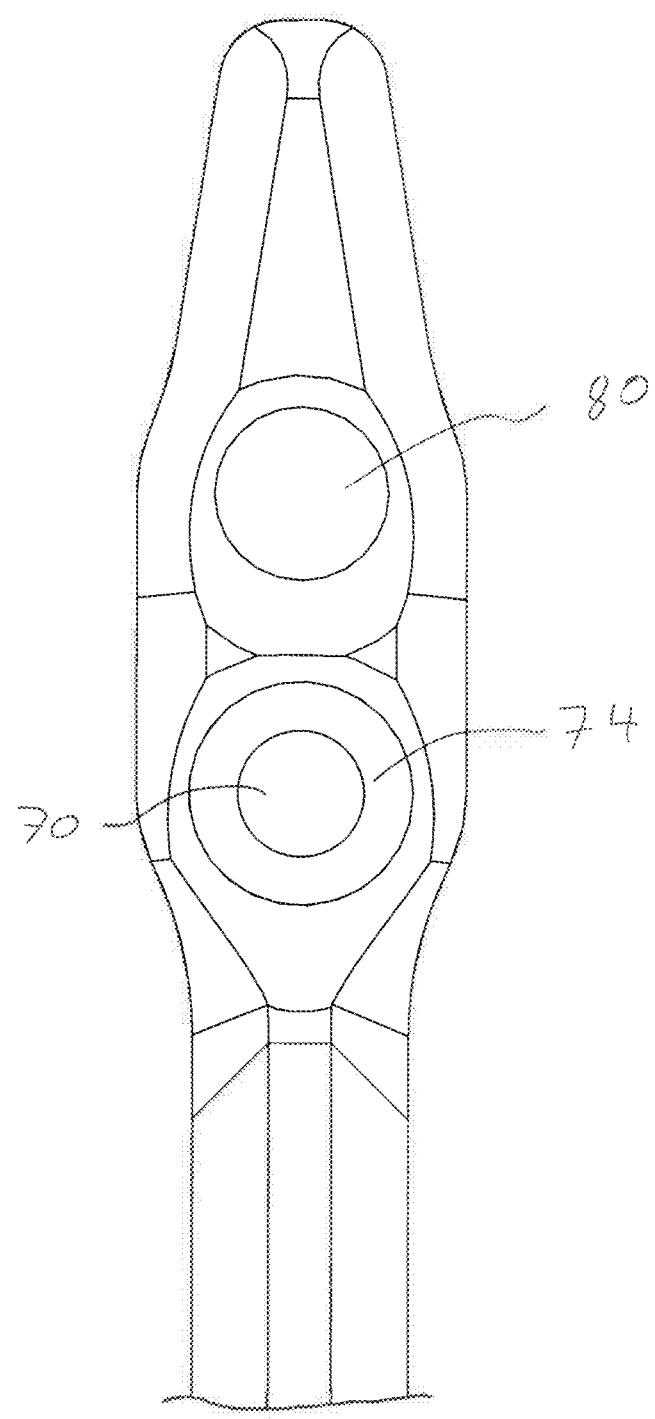
FIG. 5 is an enlarged elevational view of the bone plate member of FIG. 1 showing the through apertures of the bone plate shown in FIG. 4.

As shown in FIGS. 4 and 5, the annular surface 74 of the stop aperture 70 narrows the stop aperture 70 to block the movement of end plug 72 beyond the annular surface 74. At this point, the trailing end 26 of the surgical cable 24 can no longer be moved in direction 62 beyond the stop surface 74. Utilizing the abutting contact between the end plug 72 and the annular surface 74 provides an easy to use approach for connecting the trailing end 26 of the surgical cable 24 to the bone plate 20. The bone plate 20 and surgical cables 22, 24 may be assembled in an operating room by first selecting surgical cables 22, 24 suitable for a particular patient anatomy and then advancing the leading end portions 28 of the selected surgical cables 22, 24 through the stop aperture 70 of the bone plate 20. In another approach, the bone plate 20 and preselected surgical cables 22, 24 may be packaged in a preassembled configuration to save assembly time in the operating room.

In one form, the transverse support 58 has a tubular wall 82 with an inner surface 84 thereof defining a locking aperture 80 as shown in FIG. 4. The tubular wall 82 includes exposed crimp portions 85, 85 on opposite sides of the aperture 80 configured to be deformed toward each other and fix the cable 28 to the bone plate 20. The locking aperture 80 extends between opposite lateral surfaces 86, 88 of the bone plate 20 and is configured to receive the leading end portion 28 of the surgical cable 24. To increase the ease with which the leading end portion 28 of the surgical cable 24 may be advanced into the locking aperture 80, the bone plate 20 may include a chamfered surface 90 adjacent the openings of the aperture 70. Further, the tubular wall 82 may have a generally constant diameter along its length. In one form, the tubular wall 82 is free of any openings in communication with the locking aperture 84 which reduces the likelihood of tissues entering the aperture 84. This may also increase the strength of the tubular wall 82. Still further, the locking devices 40, 41 may be integral with the bone plate 20 and have a portion of the transverse supports 54, 58.

The locking aperture 80 is preferably sized with a diameter slightly larger than the surgical cable 24 such that the inner surface 84 of the tubular wall 82 is initially in a slip fit configuration with the surgical cable 24. The locking aperture 80 is also sized to provide a compression fit between the inner surface 84 of the tubular wall 82 and the surgical cable 24 to maintain the positioning of the tubular wall 84 along the surgical cable 24 once the tubular wall 82 has been crimped. Using a surgical cable 24 having a diameter of about 0.049 inches as an example, the outer diameter of the tubular wall 82 is initially about 0.096 inches and the diameter of the locking aperture 80 may be about 0.055 inches. Crimping the tubular wall 82 against the surgical cable 24 flattens out the tubular wall 82, decreases the diameter of the locking aperture 80 by about 0.01 inches, and forms a compression fit between the inner surface 84 of the tubular wall 82 and the surgical cable 24.

Rather than utilizing stop apertures 70 to connect one end of the surgical cables 22, 24 to the bone plate 20 and a locking aperture 80 to connect the other end of the surgical cables 22, 24 to the bone plate 20, the locking devices 40, 41 may have multiple lumen crimps with a separate lumen for crimping each end of the cables 22, 24. In other forms, the locking devices 40, 41 may be separate from the bone plate 20. For example, the bone plate 20 may have apertures for receiving the surgical cables 22, 24 but a separate and distinct crimp may be applied to each of the surgical cables 22, 24 to fix the cables 22, 24 in the closed loop configuration about the sternal halves 16, 18 after the surgical cables 22, 24 have been advanced through the apertures of the bone plate. Examples of separate and distinct crimps that could be used with such a plate member include the multiple lumen crimps disclosed in U.S. Pat. Nos. 6,832,532 and 6,629,975.

Figure 7:
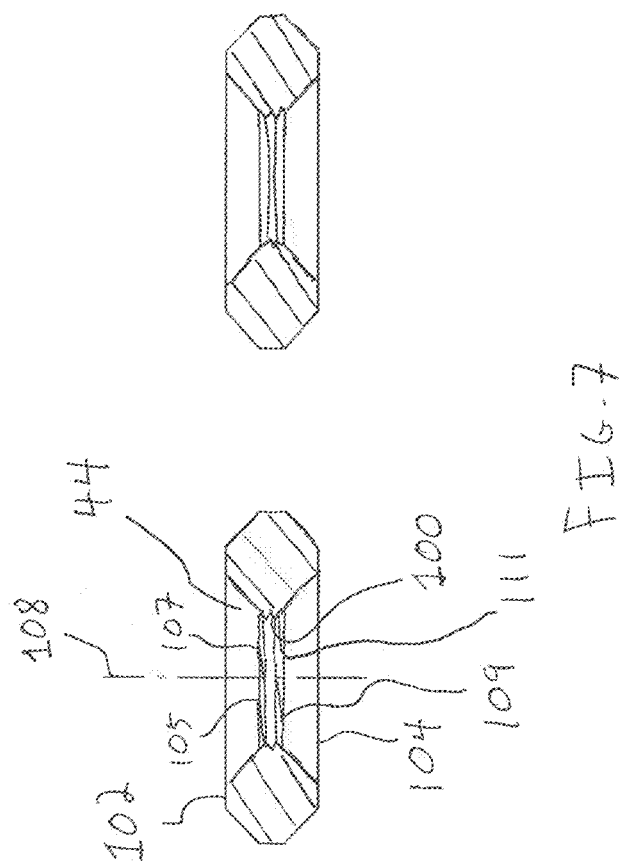
FIG. 7 is a cross sectional view taken across line 7-7 in FIG. 4 showing threads of the throughbores disposed between the upper and lower surfaces of the bone plate.
Figure 8:
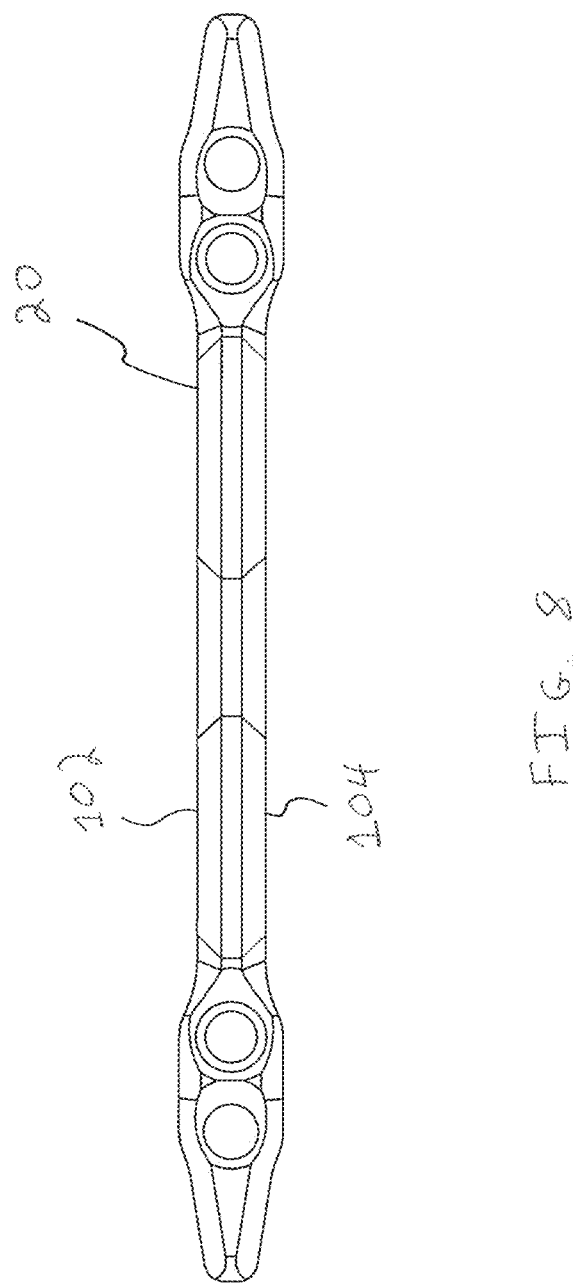
FIG. 8 is a side elevational view of the bone plate of FIG. 1 showing generally flat upper and lower surfaces of the bone plate.
Figure 9:
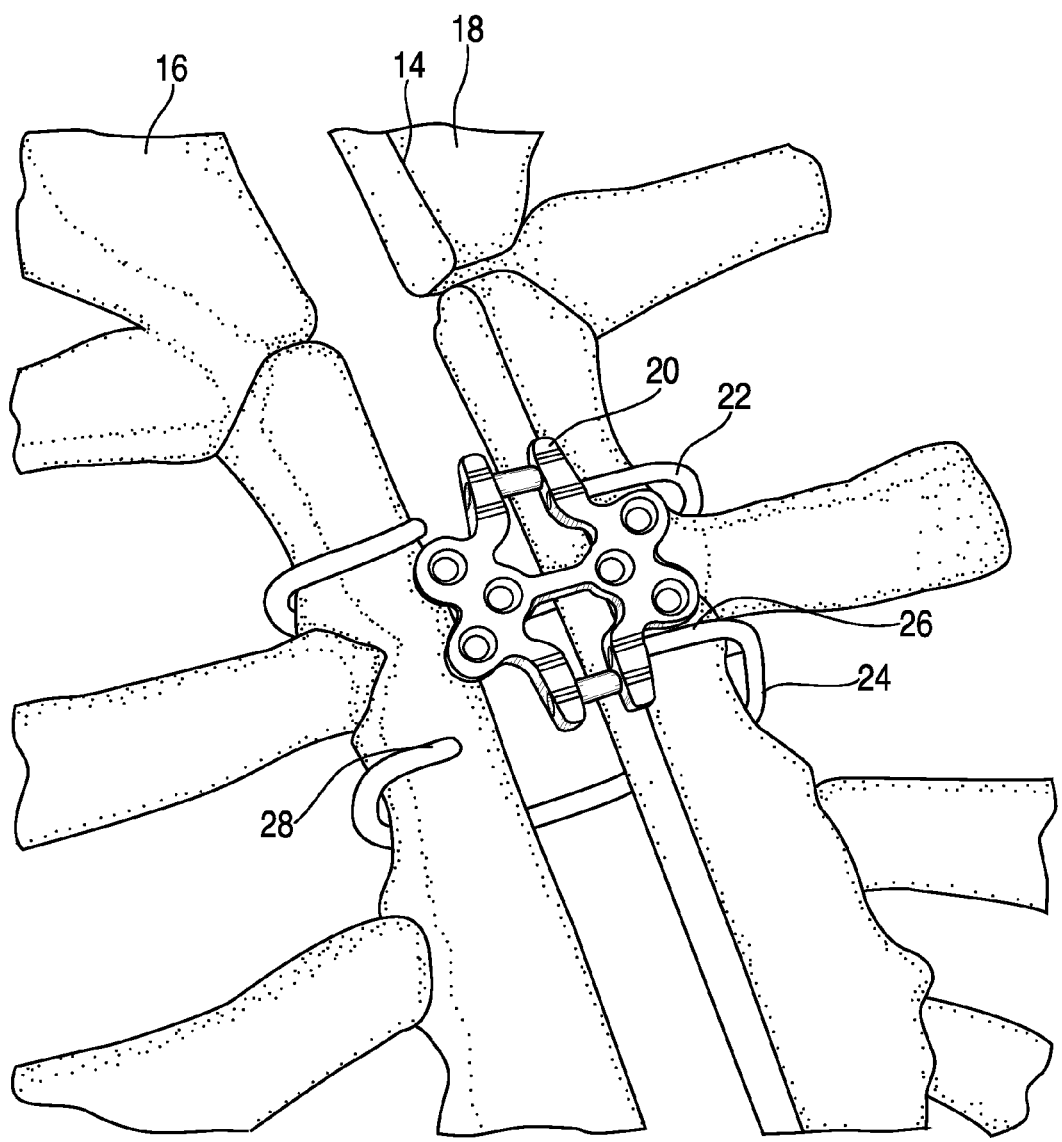

With reference to FIG. 7, the throughbores 44 of the bone plate 20 have retention devices, such as threads 100, configured for engaging threads 184 on the heads 181 of the bone screws 46 (see FIG. 17) and resisting back-out of the screws 46 from the throughbores 44. The threads 100 of each throughbore 44 are spaced inward from the upper and lower surfaces 102, 104 of the bone plate 20 along a bore axis 108 by equal distances. With reference to FIG. 8, the upper and lower surfaces 102, 104 of the bone plate 20 are generally straight and permit either the upper and lower surface 102, 104 to be placed against sternal halves 16, 18. By positioning the threads 100 inward from the upper and lower surfaces 102, 104 equal distances, the threads 184 of the bone screw 46 can engage the threads 100 of the aperture 44 regardless of whether the upper surface 102 or the lower surface 104 is facing the sternal halves 16, 18.

The threads 100 include a plurality of leads adjacent the upper and lower surfaces 102, 103 of the bone plate 20, such as leads 105, 107 adjacent the upper surface 102 and leads 109, 111 adjacent the lower surface 104. The head 181 of the bone screw 46 has threads 184 with a matching number of leads 186, 188 (see FIG. 17) that are adapted to mate with the leads 105, 107 or 109, 111 of the throughbore 44 depending on which direction the bone screw 46 is driven into the throughbore 44. For example, with reference to FIG. 7, with the lower surface 104 of the bone plate 20 positioned against the sternal halves 16, 18, a surgeon can drive the bone screw 46 from above the upper surface 102 into one of the throughbores 44 until the head 181 of the bone screw 46 is proximal the threads 100 of the throughbore 44. Rotation of the bone screw 46 brings the leads 186, 188 of the head 181 into engagement with the leads 105, 107 of the throughbore 44. Conversely, if the upper surface 102 of the bone plate 20 is positioned against the sternal halves 16, 18, the bone screw 46 would be driven from above the lower surface 104 into the throughbore 44 and the leads 186, 188 of the head 181 would engage the leads 109, 111 of the throughbore 44. In this manner, the bone screws 46 can be driven into the throughbores 44 and rotated to bring the leads 186, 188 into engagement with either of the leads 105, 107 or 109, 111 of the throughbore 44 regardless of whether the upper surface 102 or the lower surface 104 of the bone plate 20 is positioned against the sternal halves 16, 18. Although only two leads (either 105, 107 or 109, 111 depending on the orientation of the bone plate 20) are identified as engaging the leads 186, 188 of the screw head 181, the threads 100 of the throughbore 44 and the threads 184 of the head 181 each have four leads configured so that the threads 184 engage the threads 100 with a quarter-turn or less of the screw 46. Preferably, the number of leads of the throughbore threads 100 and the number of leads of the screw head threads 184 match so that all of the leads of the throughbore threads 100 engage all of the leads of the screw head threads 184 as the bone screw 46 is driven into the throughbore 44.

Figure 10:
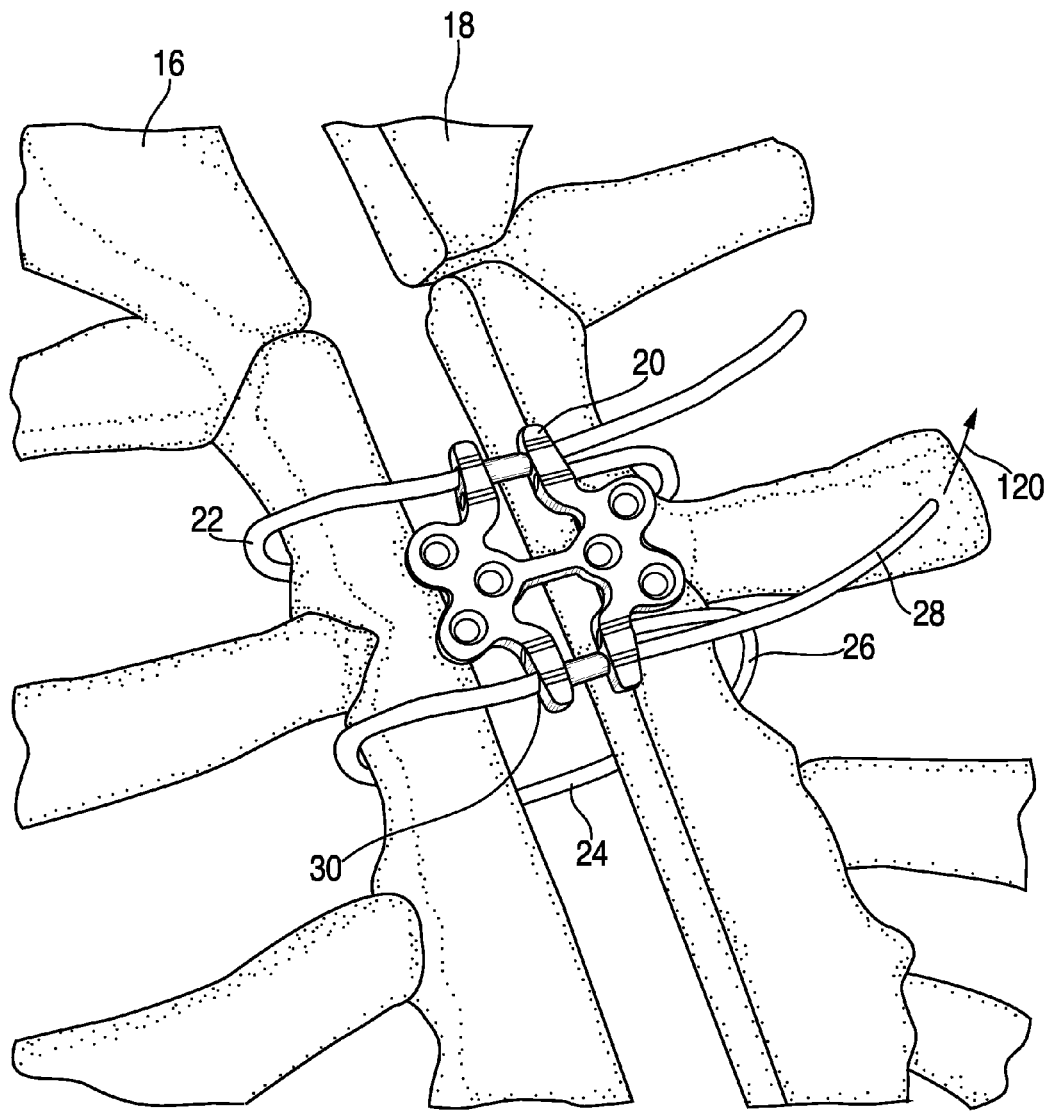
Figure 11:
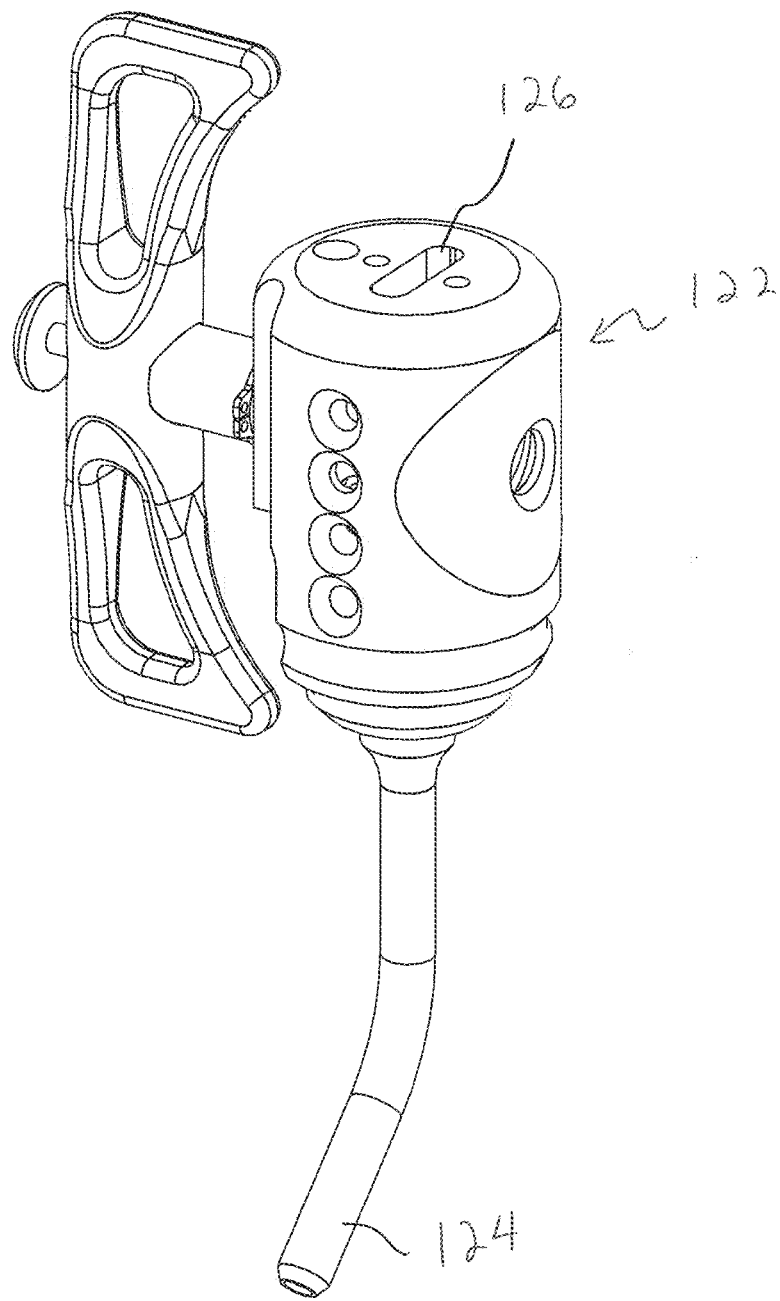

With respect to FIGS. 9-16, a method is disclosed for utilizing the bone plate system 10 to secure the halves 16, 18 of a cut sternum 12. The trailing end 26 of each cable 22, 24 may be connected to the bone plate 20 as discussed above and the bone plate 20 may be positioned above the sternal halves 16, 18. The leading end portion 28 of each cable 22, 24 is advanced around the sternal halves 16, 18 and into the locking aperture 80 adjacent lateral surface 86 (see FIG. 4). The leading end portion 28 is advanced outward from the locking aperture 80 adjacent the opposite lateral surface 88 in direction 120, as shown in FIG. 10.

Figure 12:
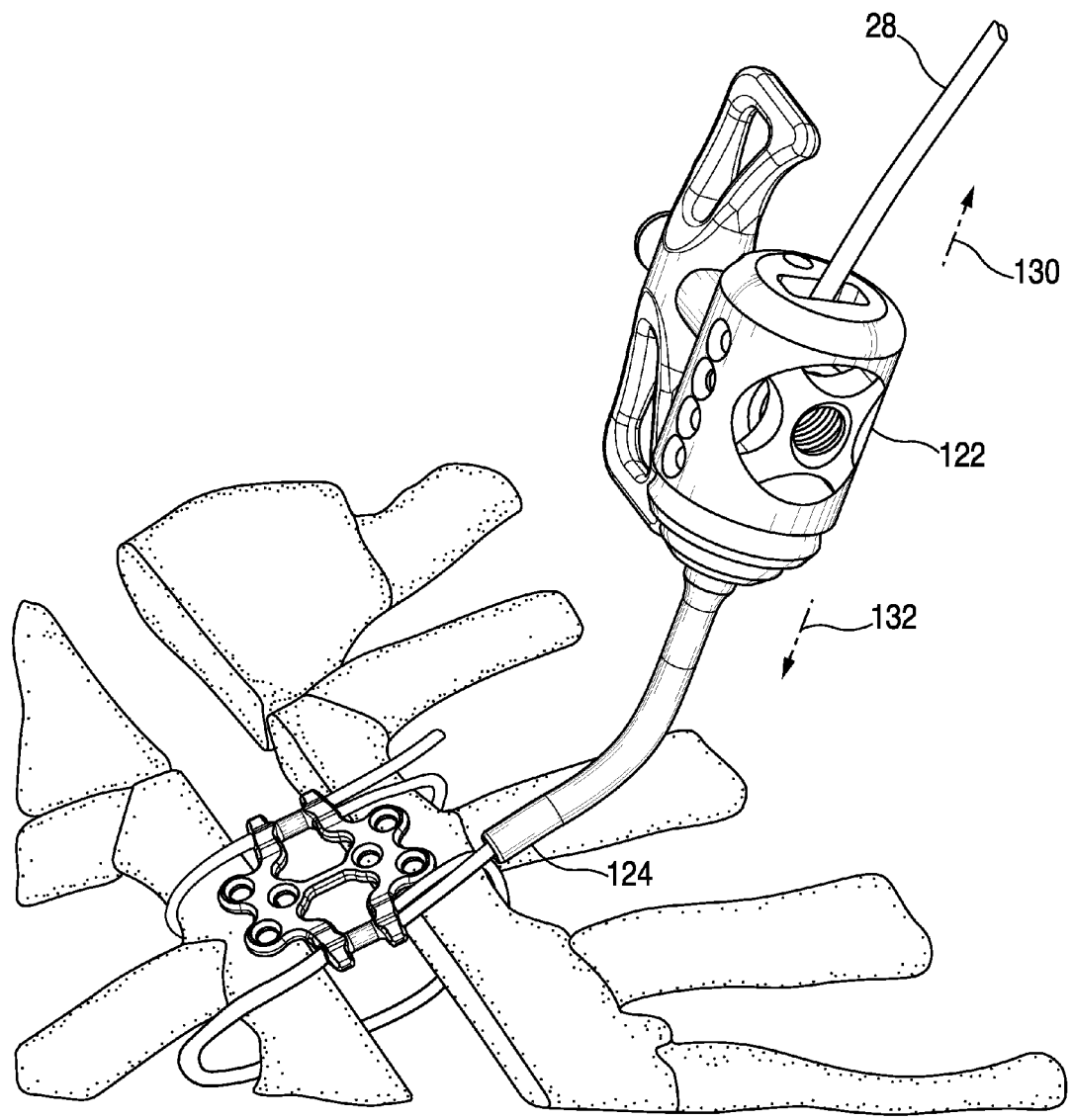
Figure 13:
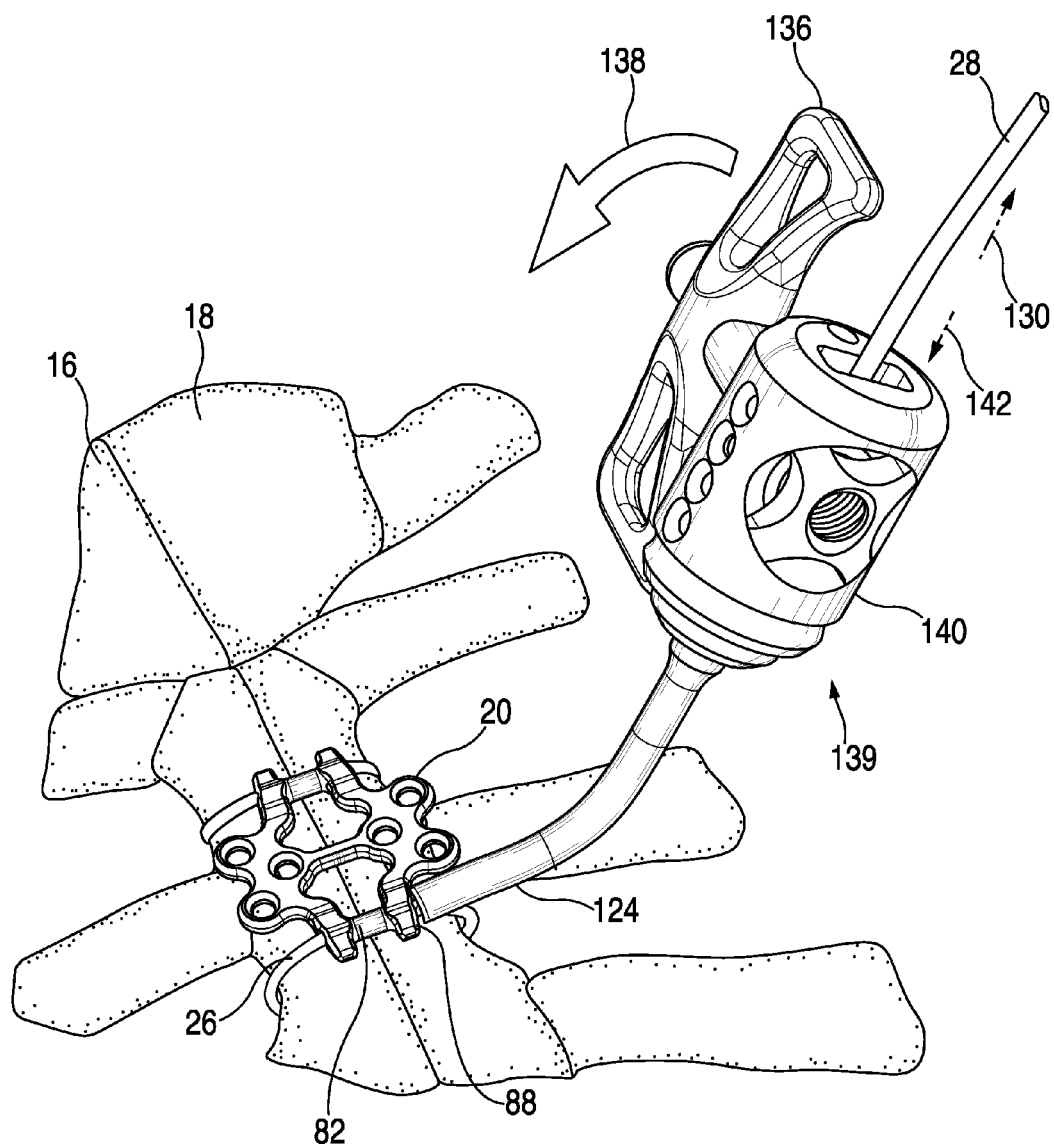

With the leading end 28 of each surgical cable 22, 24 extending beyond the lateral surface 88 of the bone plate 20, the bone plate 20 is held against the sternal halves 16, 18 and a tensioning instrument 122 (see FIG. 11) is used to apply tension to the surgical cables 22, 24 and draw the bone plate 20 against the sternal halves 16, 18. More specifically, the leading end portion 28 of the surgical cable 24 is advanced through a distal end 124 of the tensioning instrument 122 until the leading end 28 advances outward from a proximal end 126 of the tensioning instrument 122, as shown in FIG. 12. The leading end 28 of the surgical cable 24 may be grasped and pulled in direction 130 and the tensioning instrument 122 slid downward along the surgical cable 24 in direction 132 until the distal end 124 thereof abuts the lateral surface 88 of the bone plate. The handle 136 of the tensioning instrument 122 is rotated in direction 138 which causes a rotary tensioning device 139 of the tensioning instrument 122 to lock onto the surgical cable 24 and shift the surgical cable 24 in direction 130. A ratchet assembly 140 of the tensioning instrument 122 restricts return of the surgical cable 24 in direction 142 once tension has been applied to the surgical cable 24 by way of rotation of the handle 136. Continued rotation of the handle 136 advances the surgical cable 28 in direction 130, tightens the surgical cable 24 around the sternal halves 16, 18, and compresses the sternal halves 16, 18 together. Further, tensioning the surgical cable 24 draws the bone plate 20 downward against the sternal halves 16, 18 and seats the bone plate 20 securely against the compressed sternal halves 16, 18. In one approach, forceps are used in conjunction with tensioning of the surgical cable 24 to bring the sternal halves 16, 18 together.

Once the desired amount of tension has been applied to the surgical cable 24, the crimping tool 150 is used to clamp the tubular wall 82 of transverse support 58 to the surgical cable 24. The crimping tool 150 has jaws 152, 153 for being positioned on opposite sides of the tubular wall 82 with jaw surfaces 157, 159 positioned adjacent crimp portions of the tubular wall 82, such as the portions 161, 163 shown in dashed lines in FIG. 14B. To permit access to the crimp portions 161, 163, the bone plate 20 has access openings, such as through openings 143, 145, sized to permit the jaws 152, 153 to be inserted therein. The through openings 143, 145 have alignment walls, such as walls 147A, 147B and 149A, 149B extending away from the tubular wall 82 on opposite sides of the through openings 143, 145. The jaws 152, 153 have a width 154 sized to fit snugly between the walls 147A, 147B and 149A, 149B and into position on opposite sides of the tubular wall 82. More specifically, the width 154 of the jaws 152, 153 is less than a distance 156A between the walls 147A, 147B and a distance 156B between the walls 149A, 149. The close tolerances between the jaws 152, 153 and the walls 147A, 147B and 149A, 149B ensures that the jaw surfaces 157, 159 are aligned with the crimp portions 161, 163 before the crimping tool 150 crimps the tubular wall 82. For example, the distances 156A, 156B are about 0.21 inches, the width 154 of the jaws 152, 153 are about 0.2 inches, and the crimp portions 161, 163 extend along the tubular member 82 a distance 165 of about 0.140 inches.

Next, handles 160, 162 of the crimping tool 150 are squeezed together to shift the jaws 152, 153 against the crimp portions 161, 163, deform the crimp portions 161, 163 toward each other, and crimp the tubular wall 82 to the surgical cable 24. Once the tubular wall 82 has been crimped onto the surgical cable 24, the crimping tool 150 can be removed and the tensioning instrument 122 may be removed by depressing a ratchet release button 164 thereof and sliding the tensioning tool 122 along the surgical cable 24 in direction 166 (see FIG. 14). Using a cable cutter 170, the leading end portion 28 is then cut flush with the lateral surface 88 of the bone plate 20. The process of tensioning and crimping is repeated with the surgical cable 22. In some applications, the crimping tool 150 may be configured to require a particular amount of travel of the jaws 152, 153 towards one another before the crimping tool 150 may be disengaged from the tubular wall 82. This configuration ensures that the tubular wall 82 has deformed a predetermined distance into engagement with the surgical cable 24 and achieved a sufficient crimp strength therewith before the surgeon can remove the crimping tool 150.

Figure 16:
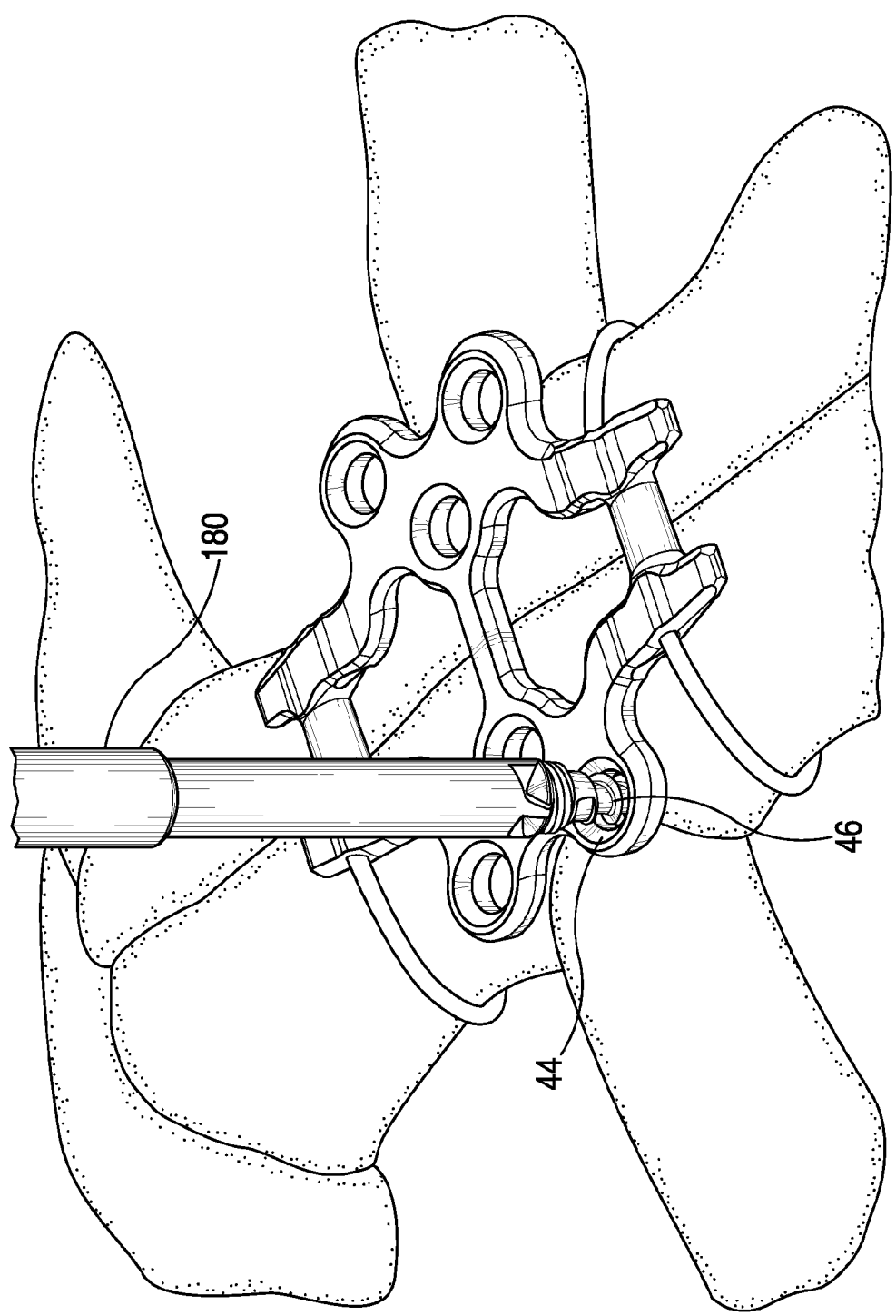

With the surgical cables 22, 24 tensioned and crimped to the bone plate 20, the bone screws 46 may be connected to a driver tool 180 (see FIG. 18A) and driven into throughbores 44 of the bone plate 20 to secure the bone plate 20 to the sternal halves 16, 18, as shown in FIG. 16.

Figure 16A:
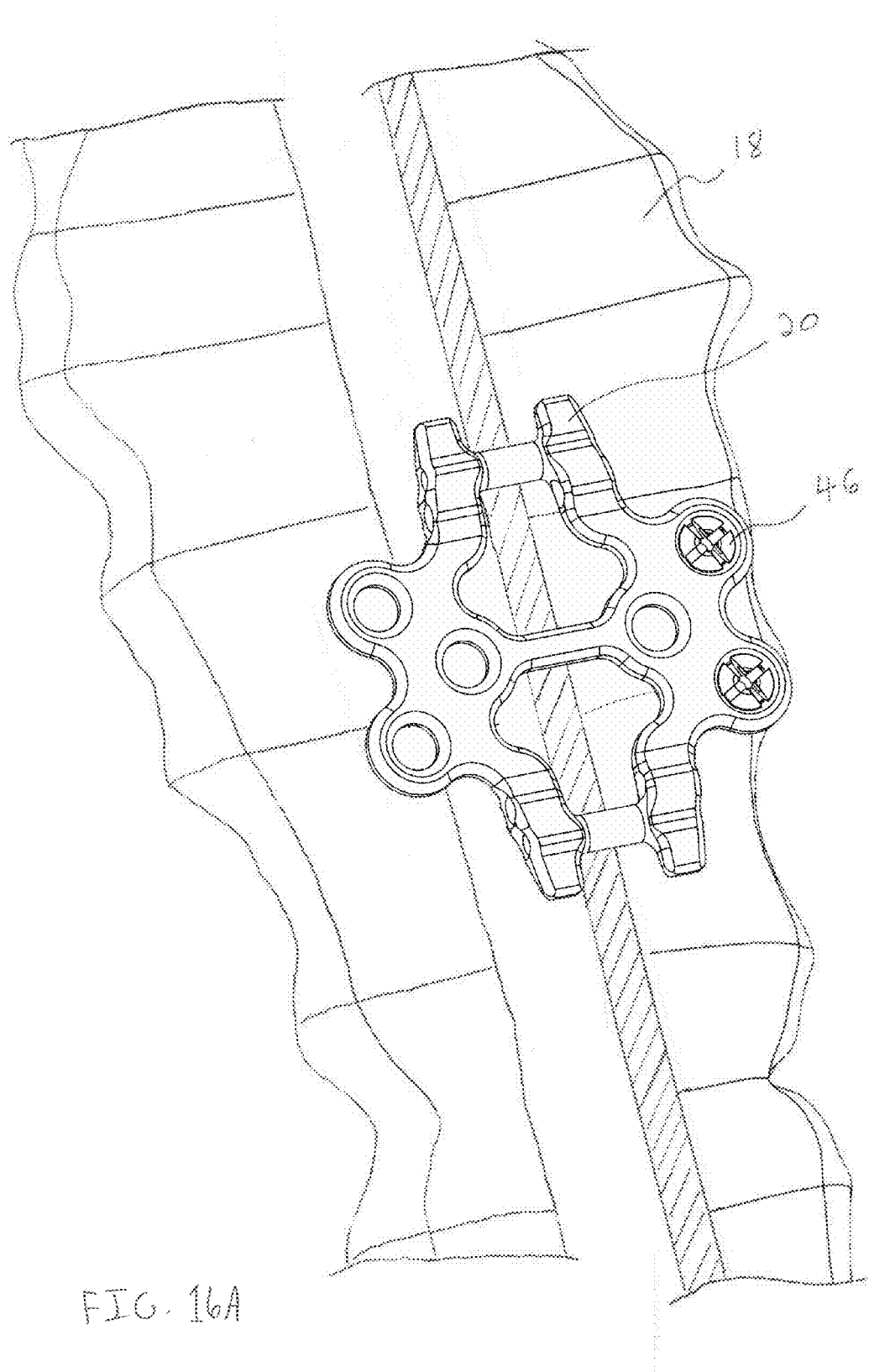
FIGS. 16A-16D illustrate an alternative approach of using the bone plate system of FIG. 1 to secure the halves of the cut sternum.
Figure 16B:
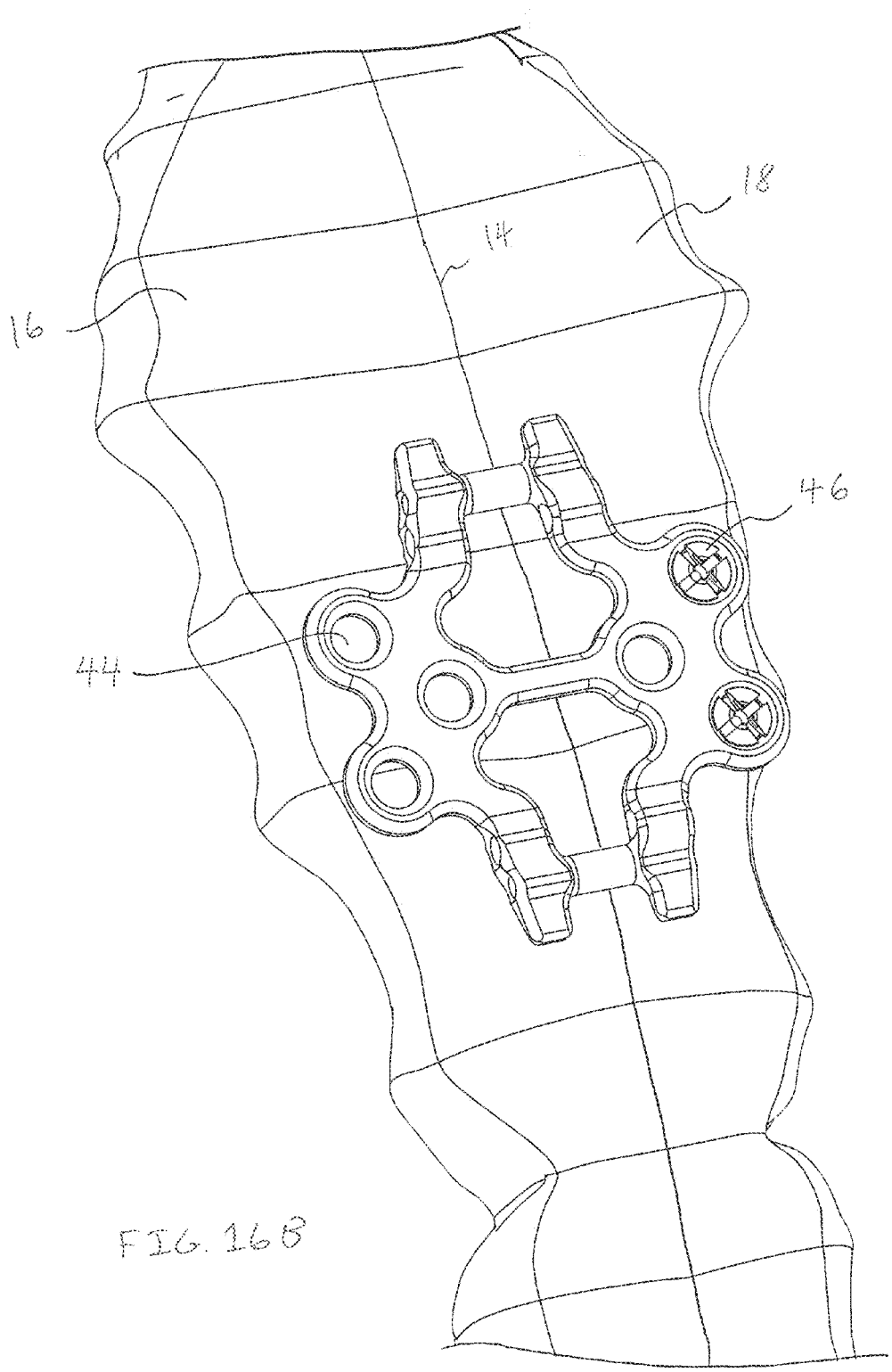
Figure 16C:
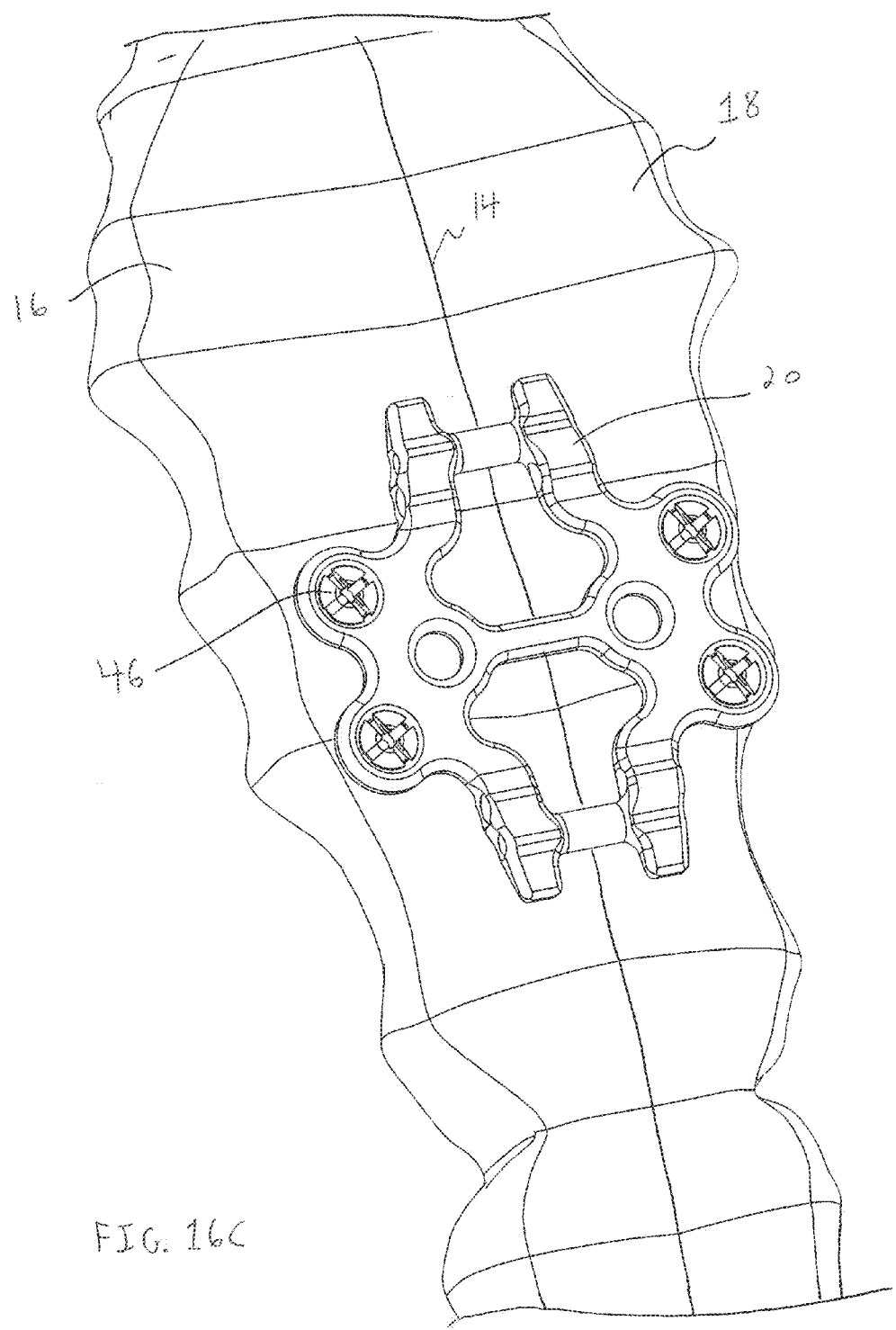
Figure 16D:
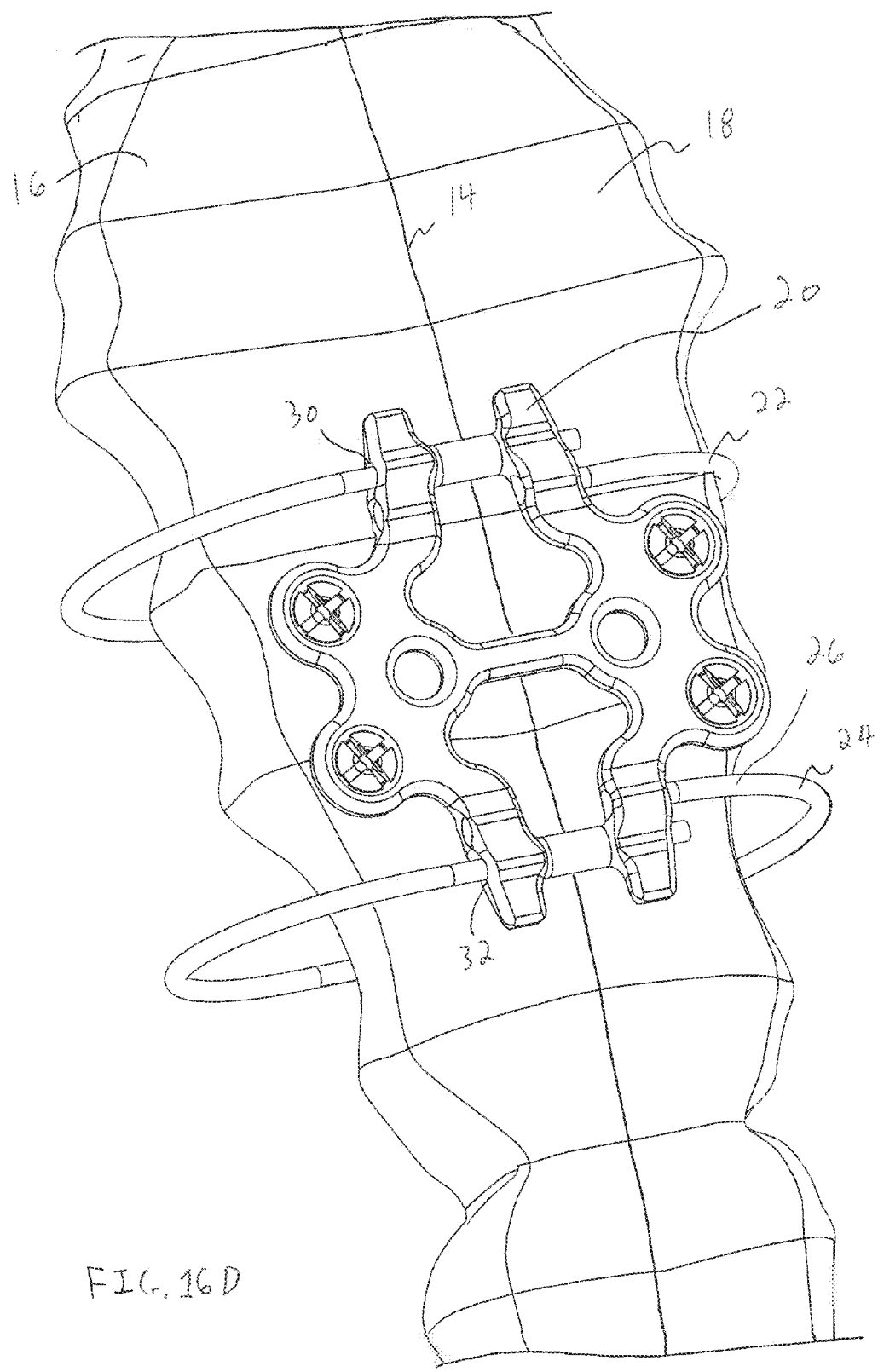

In an alternative approach shown in FIGS. 16A-D, the bone screws 46 may be used to secure the bone plate 20 to one of the sternal halves 16, 18, such as sternal half 18 as shown in FIG. 16A. Next, the sternal halves 16, 18 are approximated together using forceps, wire, or another approach, as shown in FIG. 16B. With the sternal halves 16, 18 approximated, bone screws 46 are driven into the throughbores 44 of the bone plate 20 disposed above sternal half 16, as shown in FIG. 16C. Next, the distal end portions 26 of the surgical cables 22, 24 are connected to the bone plate 20 and the leading end portions 28 of the surgical cables 22, 24 are looped around the sternal halves 16, 18 and into openings 30, 32 of the bone plate 20, as shown in FIG. 16D. The surgical cables 22, 24 are then tensioned and locked to the bone plate as described above. Although the surgical cables 22, 24 are connected to the bone plate 20 after the bone screws 46 have secured the bone plate 20 to the sternal halves 16, 18, the surgical cables 22, 24 may still act as a primary load bearing mechanism to resist movement of the sternal halves 16, 18.

In yet another approach, the sternal halves 16, 18 may be approximated together using forceps, wires, or another approach before placing the bone plate 20 on the approximated sternal halves 16, 18, looping the surgical cables 22, 24 around the sternal halves 16, 18, tensioning the surgical cables 22, 24, locking the bone plate 20 to the surgical cables 22, 24, and driving the bone screws 46 into the throughbores 44 of the bone plate 20 to fix the bone plate 20 to the sternal halves 16, 18. This approach is similar to the method described above with respect to FIGS. 9-16, with the exception that the forceps or wires are used to approximate the sternal halves rather than the surgical cables 22, 24.

Figure 18:
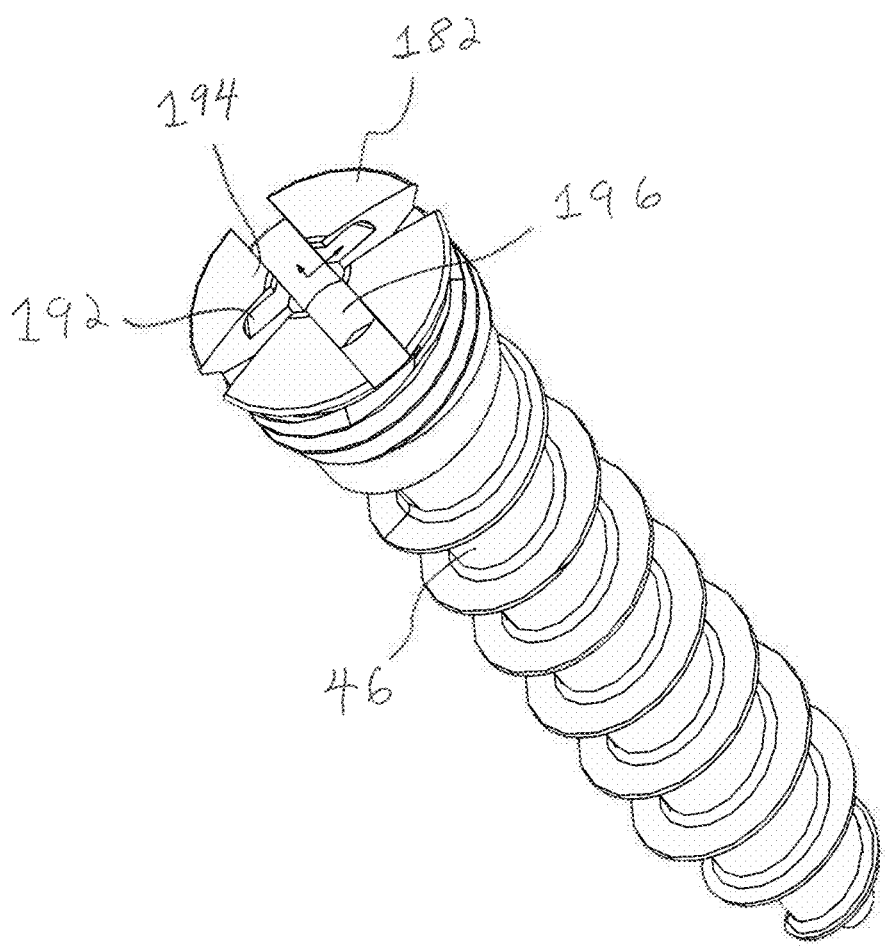
FIG. 18 is a perspective view of the bone screw of FIG. 17 showing radially extending undercuts in the head of the bone screw for engaging a retention mechanism of a driver tool.
Figure 18A:
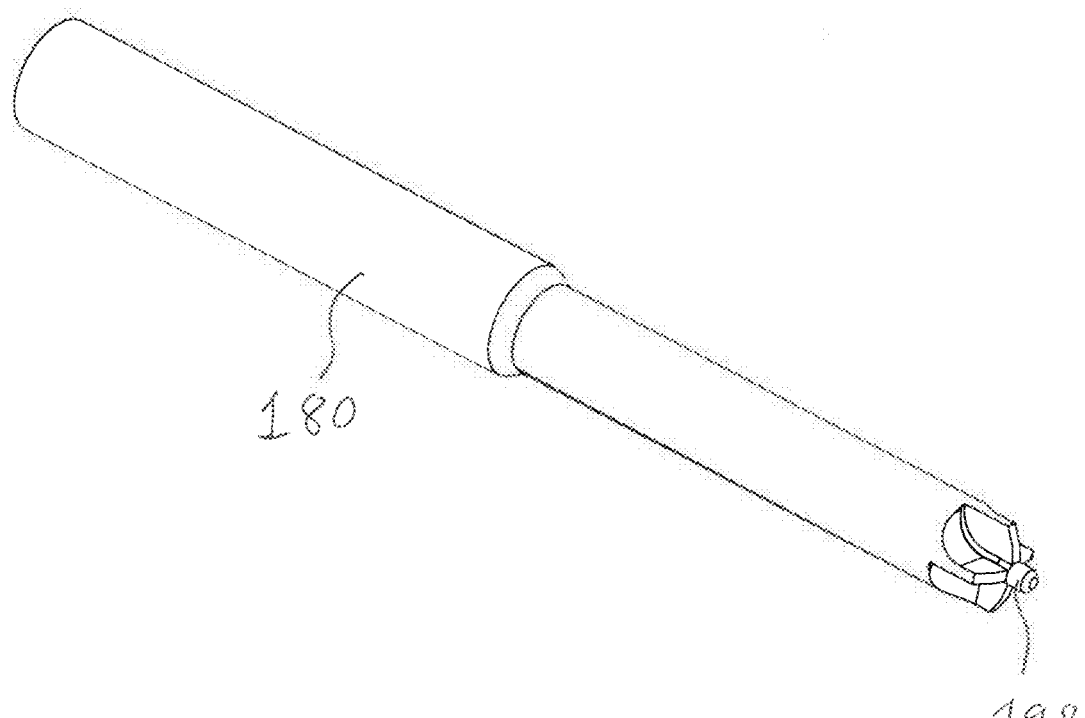
FIG. 18A is a perspective view of a driver tool showing a centering pin projecting from a distal end of the tool for centering the tool on a screw head.

With reference to FIGS. 17 and 18, an elevational view of one of the bone screws 46 is shown. The bone screw 46 has a head 181 having drive structures 182 for receiving a distal end of the driving tool 180. The drive structures 182 have undercuts 192 and radially extending members 194 for engaging corresponding a screw retention feature on the driving tool 180, such as a centering pin 198 of the driving tool 180. Advancing the centering pin 198 into a blind bore 196 of the screw head 181 centers the distal end of the driving tool 180 on the screw head 181 and causes the centering pin 198 to resiliently deflect the radially extending members 194 downward. This produces a friction fit between the centering pin 198 and the radially extending members 194 which keeps the screw 46 retained on the distal end of the driving tool 180 before driving the screw 46 into bone.

The head 181 also includes threads 184 that include multiple leads 186, 188 for engaging the multiple lead threads 100 of the throughbore 44. The threads 184 provide tactile feedback to the surgeon driving the bone screw 46 into bone that the head 181 is engaged with the bone plate 20. Further, the threads 184 provide resistance to the bone screw 46 backing out of the throughbore 44 of the bone plate 20. As shown in FIG. 17, the screw 46 has an elongate shank 190 with threads 192 thereon that may have a different pitch, size, and number of leads than the threads 184 of the head 181. In one form, the shank 190 is configured to be self-drilling and self-tapping.

The surgical cables 22, 24 are made of surgical grade braided multi-stranded stainless steel cable. Other materials such as titanium alloy, cobalt chromium alloy, polymers, or other biocompatible materials may also be used. The braided surgical cables 22, 24 have a significantly higher tensile strength than surgical wires and provide better resistance to separation and relative movement of the sternal halves 16, 18. In one form, the cables 22, 24 have a diameter in the range of about 0.8 mm to about 2.4 mm, and more preferably about 1.3 mm. The cables 22, 24 may be swedged to reduce surface roughness and may have a high flexibility which may provide a tighter loop yet avoid damage to surrounding tissue. The bone plate 20 may be fabricated from a surgical grade stainless steel, titanium, titanium alloy, cobalt chromium alloy, nitinol, polyether ether ketone, or other biocompatible materials. Likewise, the bone screws 46 may be made of, for example, stainless steel, titanium, titanium alloy, or cobalt chromium alloy. The components of the cable tensioner 122 may be made of metals or alloys including stainless steel.

Figure 19:
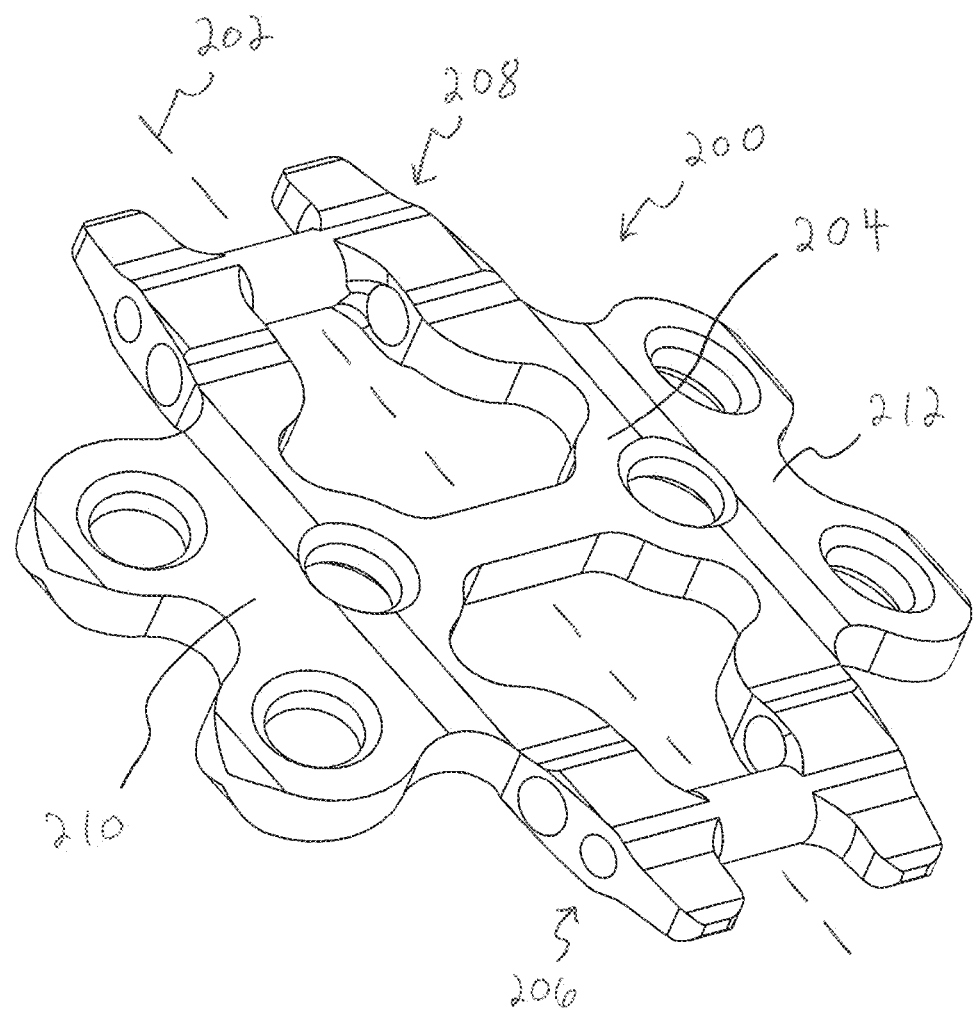
FIG. 19 is a perspective view of another bone plate member having a general curvature of the bone plate along its length.
Figure 20:
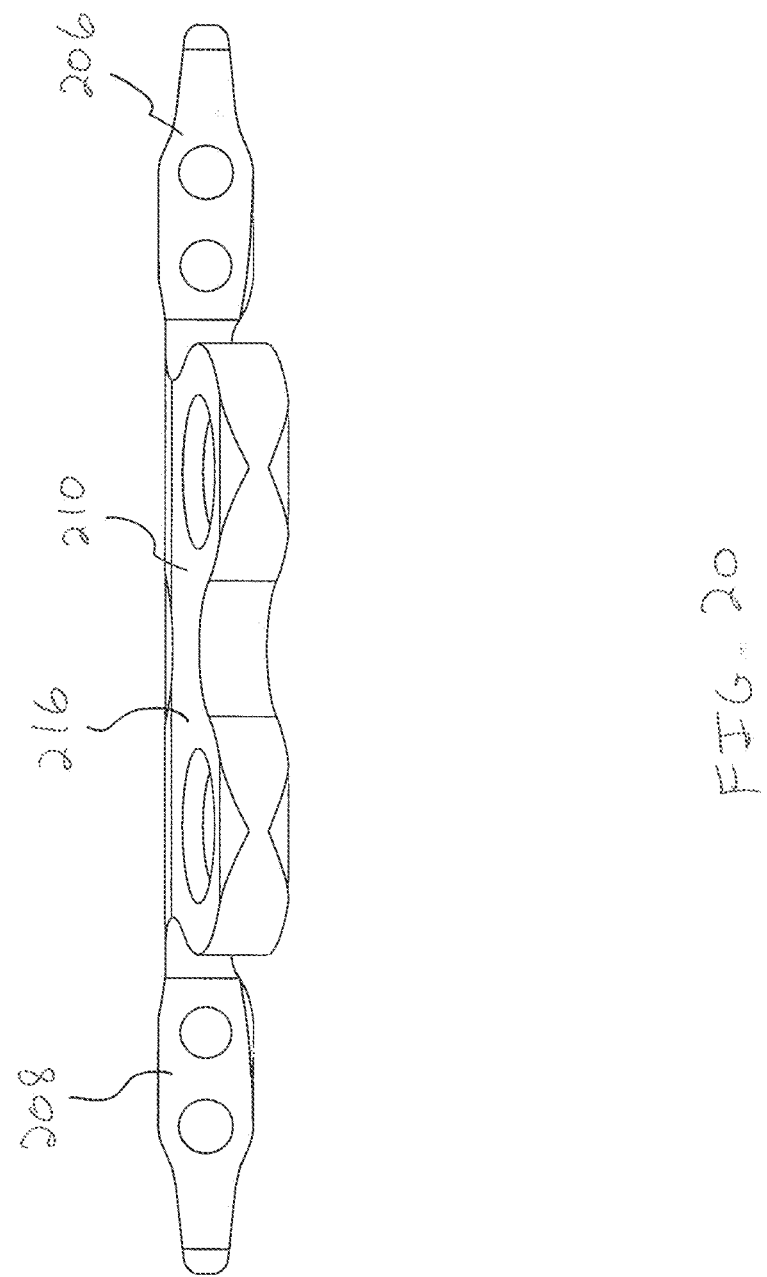
FIGS. 20 and 21 are elevational views of the bone plate of FIG. 19 showing a generally convex upper surface of the bone plate and a generally concave lower surface of the bone plate.
Figure 21:
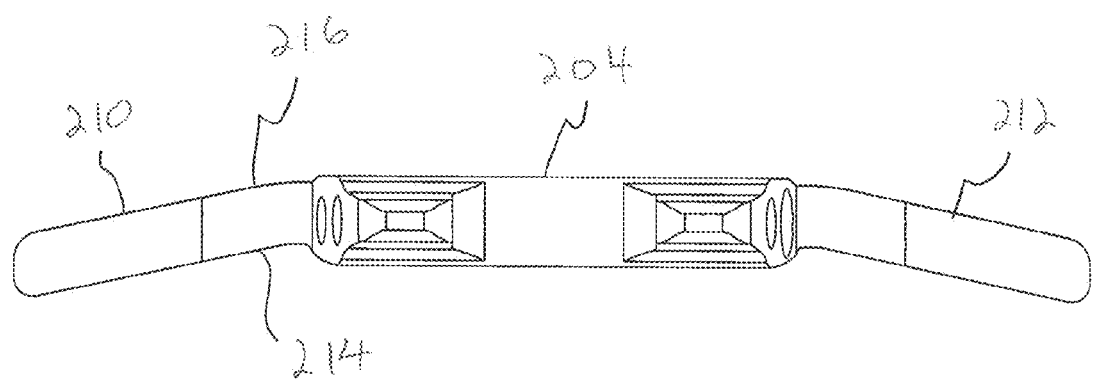
Figure 22:
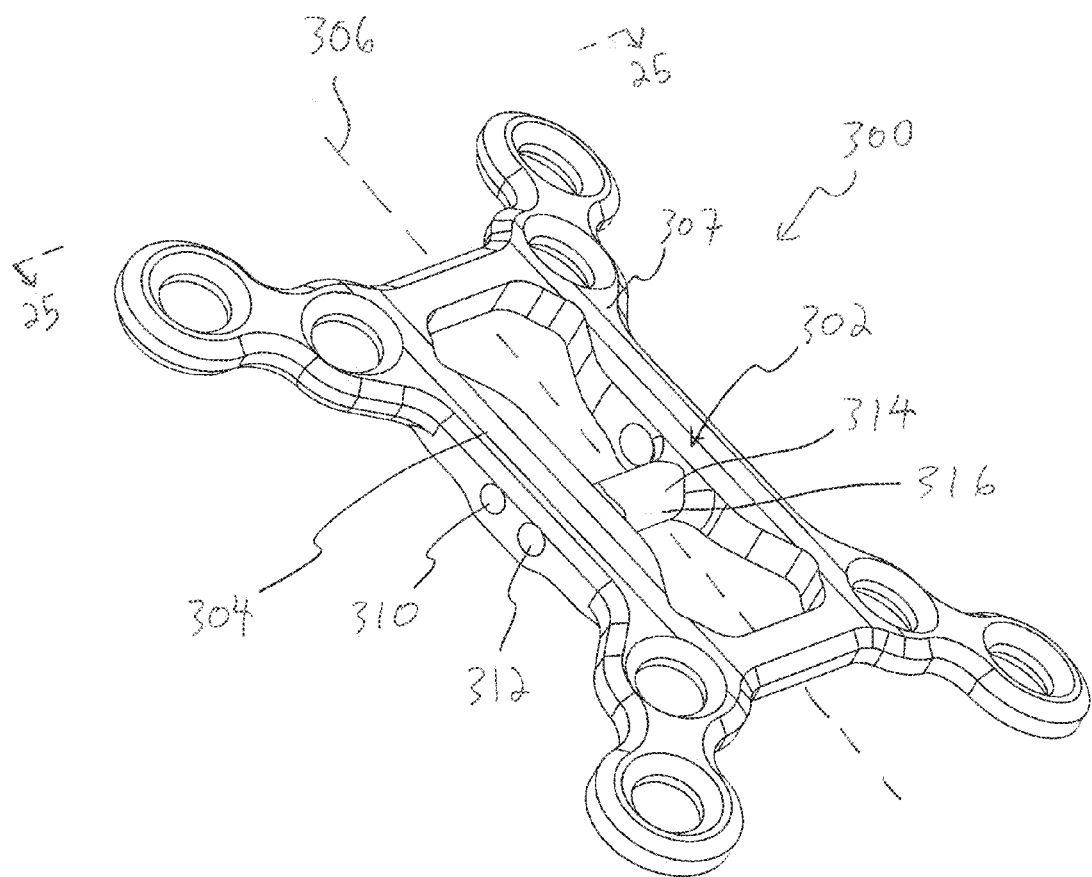
FIG. 22 is a perspective view of another plate member having a single locking device for locking a surgical cable to the bone plate.

Referring now to FIGS. 19-21, there is illustrated another embodiment of a plate member 200 in accordance with the present invention. The bone plate 200 is generally the same as plate member 20 described above with respect to FIGS. 1-8, with the exception of a curvature of the bone plate about at longitudinal axis 202 thereof.

More particularly, the bone plate 200 has a central portion 204 aligned along the longitudinal axis 202 and locking devices 206, 208 also aligned along the longitudinal axis 202 on opposite sides of the central portion 204. The bone plate 200 has curved plate halves 210, 212 that are shaped to conform to bones having either a convex or concave outer surface. More specifically, if the bones (such as sternal halves 16, 18) have a convex outer surface, a concave lower surface 214 (see FIG. 21) of the bone plate 200 would be positioned against the outer surfaces of the bones. However, if the bones had a concave outer surface, a convex upper surface 216 of the bone plate 200 would be positioned against the bones. In this manner, the bone plate 200 can be flipped to position either the concave lower surface 214 or the convex upper surface 216 against the bones to be secured depending on the anatomy of the patient. This provides greater flexibility and the ability to utilize a single plate member 200 for two different anatomies.

Figure 26:
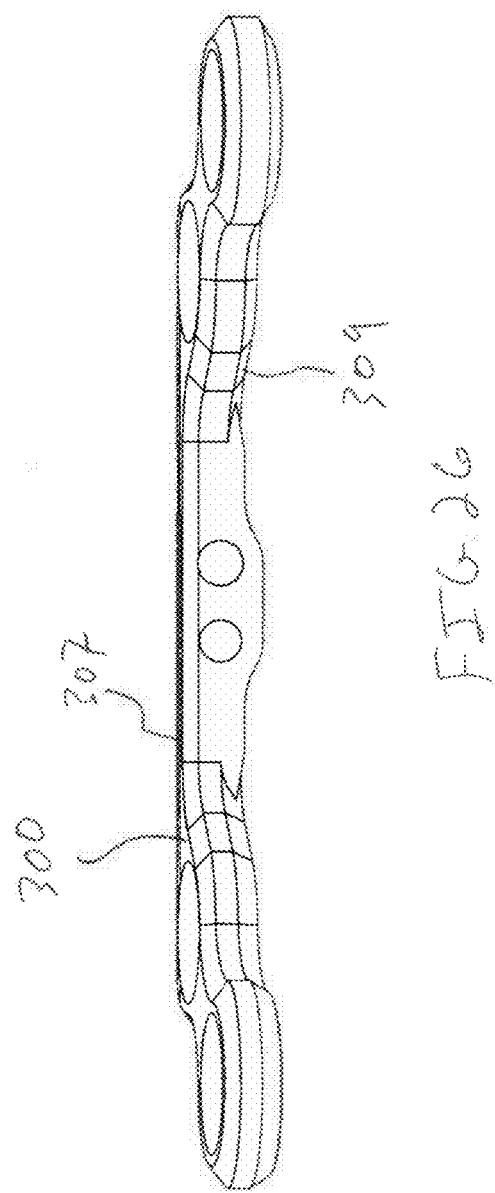
FIGS. 26 and 27 are elevational views of the bone plate of FIG. 22 showing a generally convex upper surface and a generally concave lower surface of the bone plate.
Figure 27:
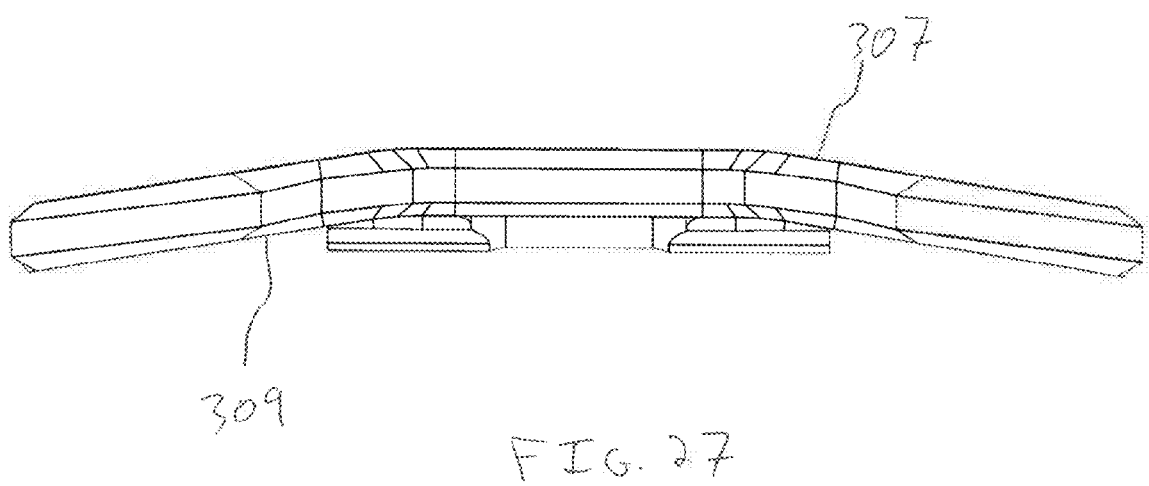

With reference to FIGS. 22-27, another embodiment of a plate member 300 is shown. The bone plate 300 is similar to the bone plates 20, 200 except that the bone plate 300 has a single locking device disposed on a central portion 304 of the bone plate 300. Further, like the bone plate 200, the bone plate 300 has a curvature about a longitudinal axis 306 thereof such that the bone plate 300 has a convex upper surface 307 and a concave lower surface 309, as shown in FIGS. 26 and 27.

Figure 23:
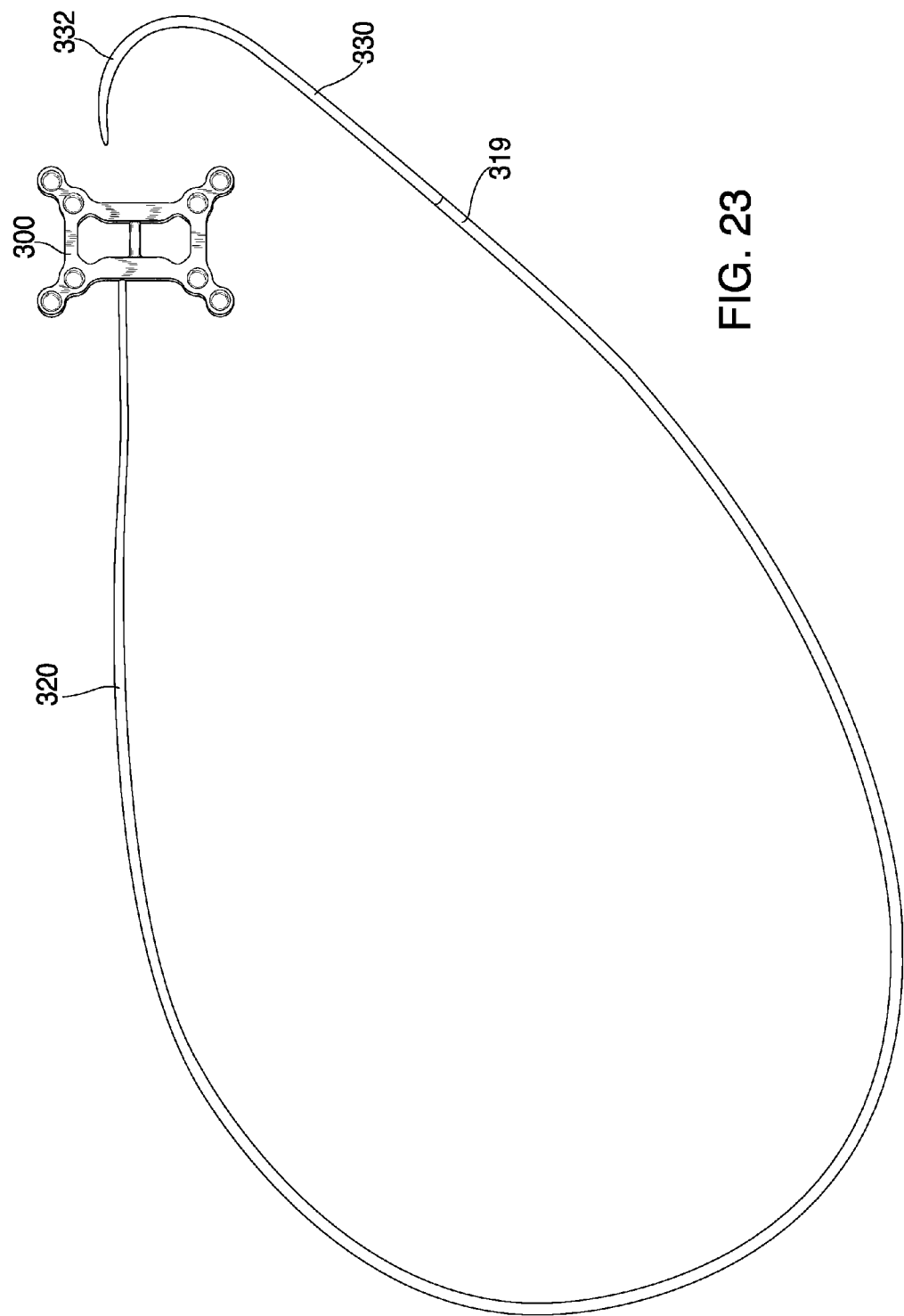
FIG. 23 is a plan view of the bone plate of FIG. 22 with a surgical cable having one end connected to the bone plate and an opposite end with a hook disposed thereon for advancing around bones.
Figure 24:
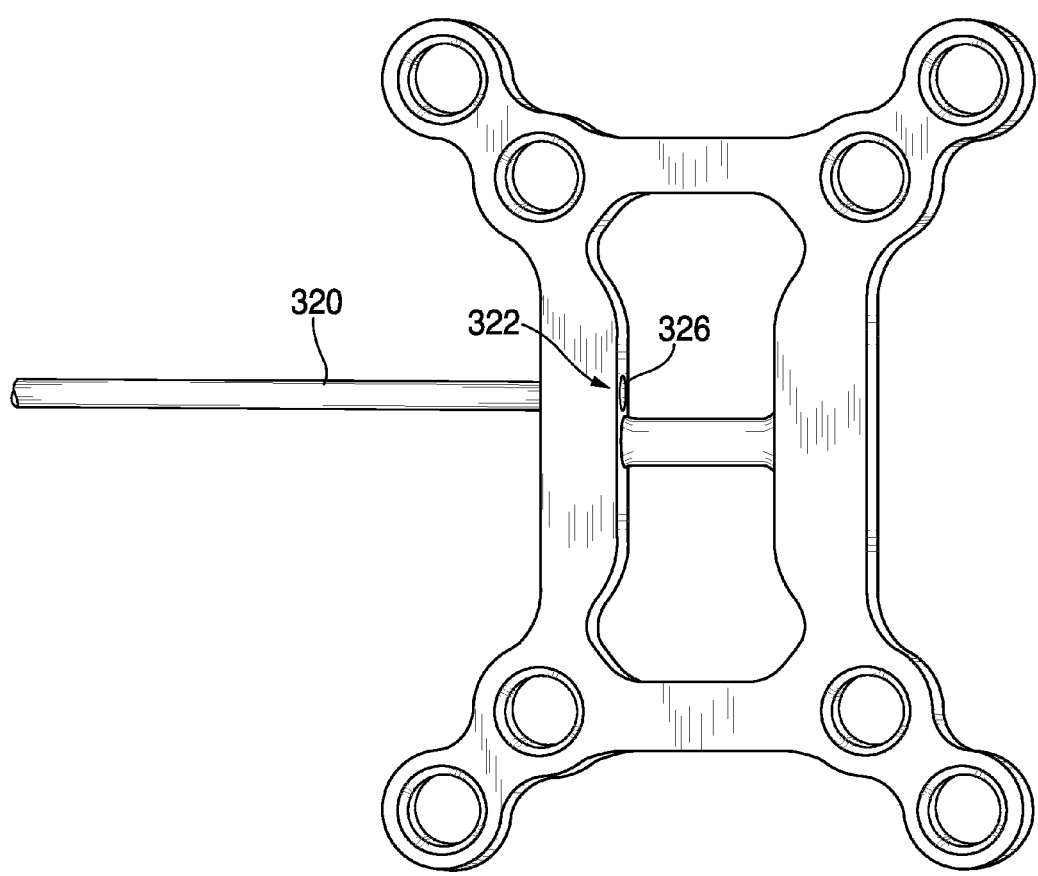
FIG. 24 is an enlarged perspective view of the bone plate and surgical cable of FIG. 23 showing the end of the surgical cable connected to the bone plate.
Figure 25:
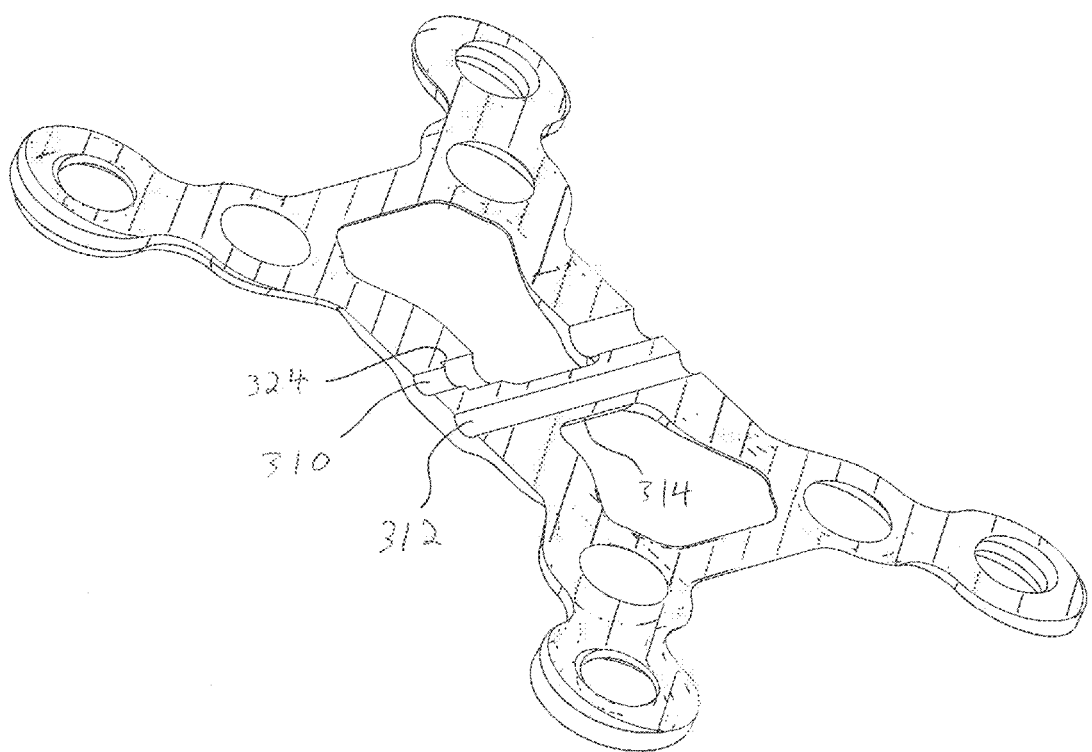
FIG. 25 is a cross sectional view taken across line 25-25 in FIG. 22 showing through apertures of the bone plate for receiving the surgical cable.

Like the locking devices 40, 41 of the bone plate 20, the locking device 302 includes a stop aperture 310, a locking aperture 312, a transverse support 314, and a tubular wall 316. The stop aperture 310 is sized to permit a surgical cable 320 (see FIG. 23) to be advanced therethrough and form a connection 322 between and annular stop surface 324 of the stop aperture 310 and a plug 326 of the cable 320 (see FIG. 24). With reference to FIG. 23, the surgical cable 320 may include a hardened integrated lead 330 and a hook 332 releasably connected thereto. The hook 332 may be used for advancing a leading end 319 of the surgical cable 320 around bones, such as the sternal halves 16, 18 of the sternum 12. Once the leading end 319 has been advanced around the bones, the hook 332 may be pulled off of the integrated lead 330 and then the integrated lead 330 may be advanced through the locking aperture 312. The locking device 302 of the bone plate 300 may then be reconfigured to a locked configuration as explained above with respect to locking device 40.

Figure 28:
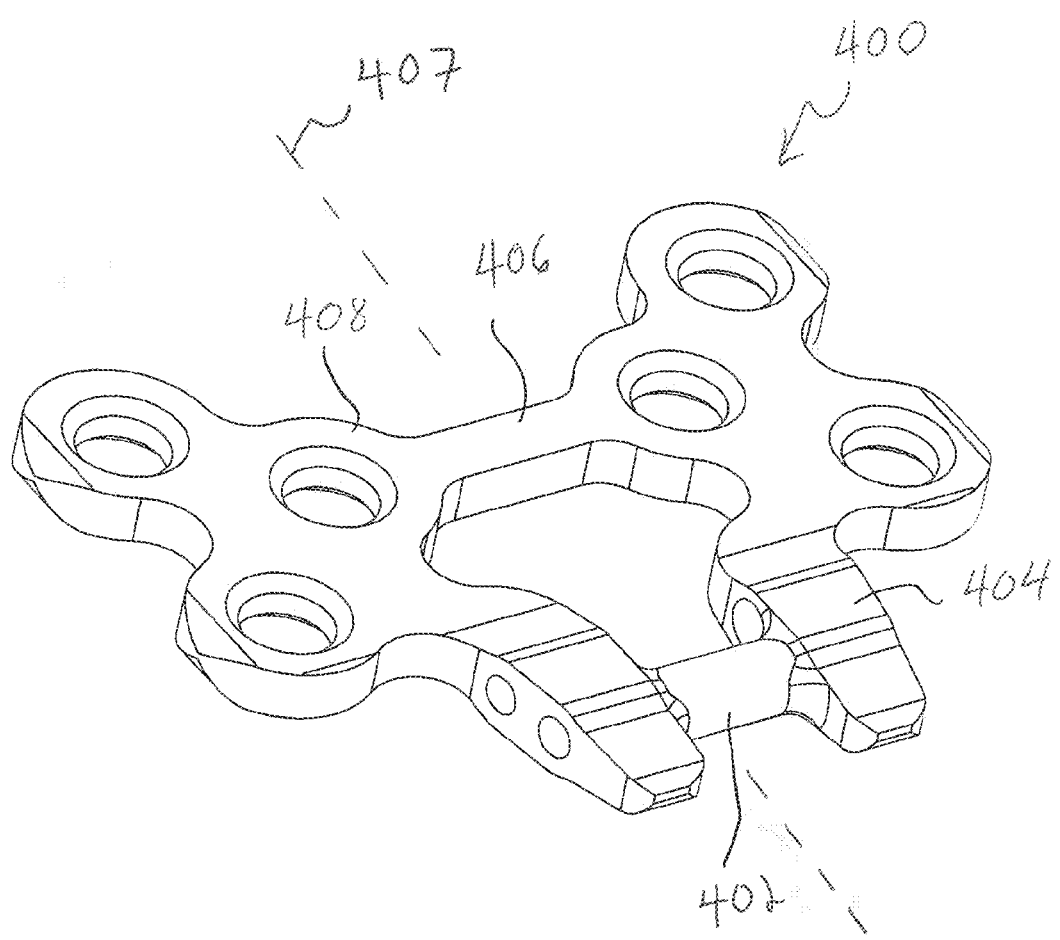
FIG. 28 is a perspective view of another plate member showing a single locking device of the bone plate disposed at one end of the bone plate.
Figure 31:
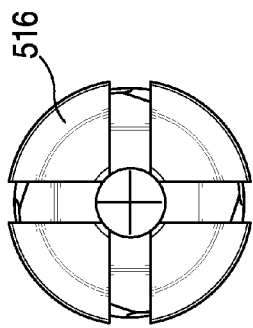
FIGS. 29-32 are views of another bone plate and screws for use therewith.
Figure 32:
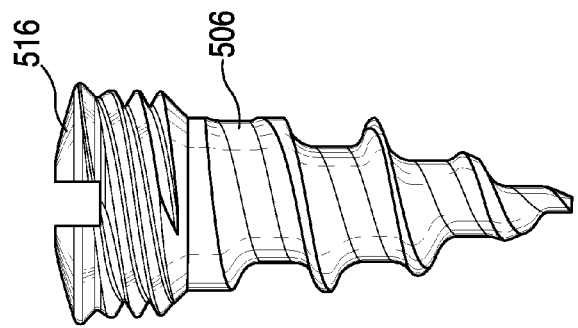
Figure 30:
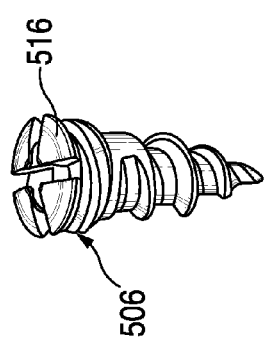
Figure 29:
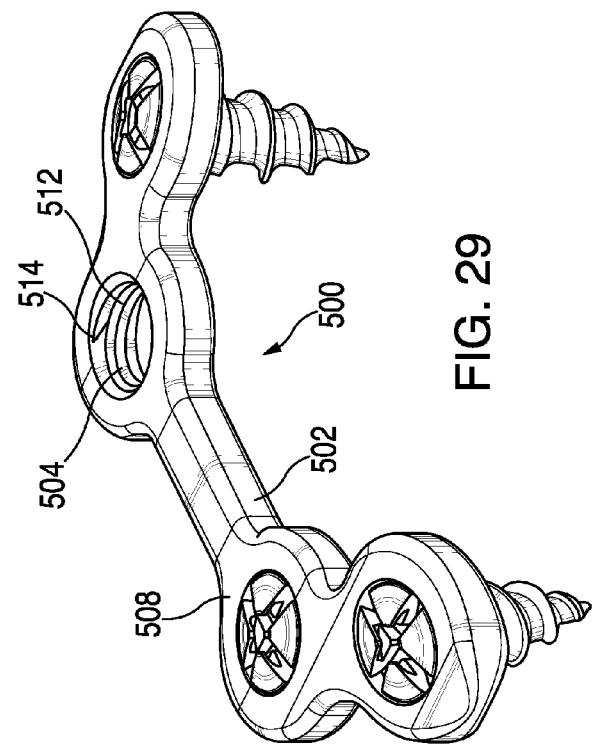

Referring now to FIGS. 28 and 29, there is illustrated another embodiment of a plate member 400. The bone plate 400 is similar to the bone plates discussed above, except that the bone plate 400 has a single locking device 402 positioned at one end 404 of the bone plate 400 opposite a transverse support portion 406 of the bone plate 400 along a longitudinal axis 407 of the bone plate 400. The bone plate 400 allows a surgical cable, such as surgical cable 24, to be offset from lobes 408 of the bone plate 400.

With respect to FIGS. 29-33, another bone plate system 500 is shown. The bone plate system 500 is similar in a number of ways to the foregoing bone plate systems in that the bone plate system 500 includes a plate member 502 having throughbores 504 therein for receiving bone anchors, such as bone screws 506, to secure the bone plate 502 to one or more bones. Further, the bone plate 502 may have a convex upper surface 508 and a concave lower surface 510 that conform to the outer surfaces of the one or more bones. Further, the bone plate throughbore 504 has threads 512 including multiple leads 514 for engaging similar threads on a head 516 of the bone anchor 506. The bone plate system 500 is different from the bone plate system 10 in that the bone plate system 500 lacks a locking device for securing a surgical cable to the bone plate 500. However, the bone plate system 500 may be used in conjunction with a surgical wire, locking device, and/or the other bone plate systems discussed above.

Figure 34:
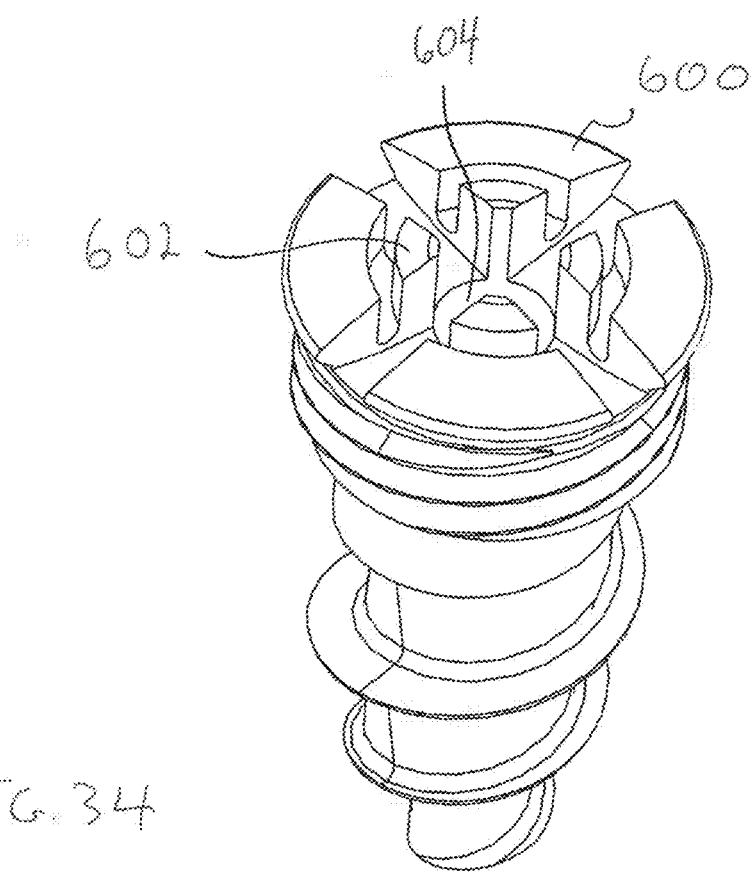
FIG. 34 is a perspective view of an alternative screw showing upstanding features of the screw head for engaging a retention feature of a driver tool.
Figure 35:
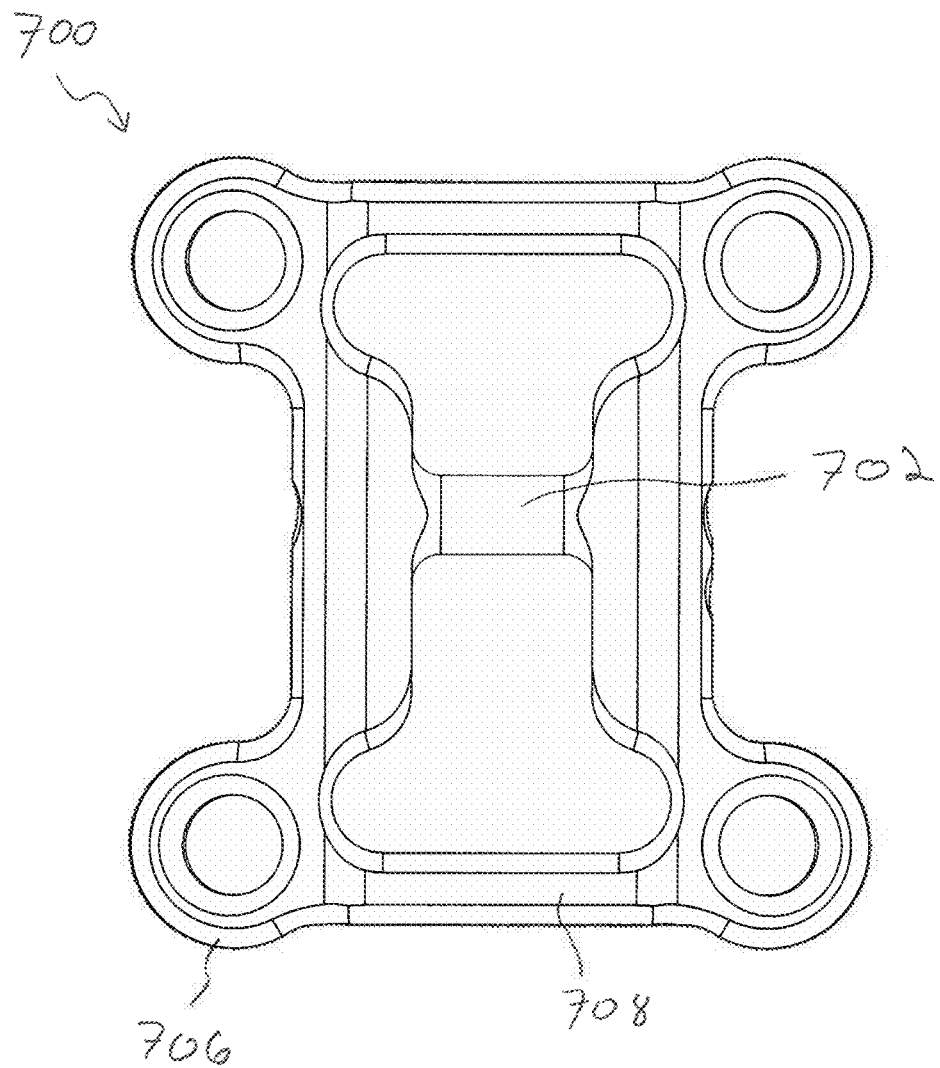
FIG. 35 is a plan view of another plate member having a single locking device for locking a surgical cable to the bone plate

An alternative embodiment of a bone screw head 600 is illustrated in FIG. 34. The head 600 includes upstanding, resilient members 602 that deform radially outward with connection of a driver tool to the head 600. For example, advancing the centering pin 198 of the driving tool 180 into a blind bore 604 of the screw head 600 causes the centering pin 198 to deflect the upstanding members 602 radially outward. Deforming the upstanding members 602 radially outward causes the upstanding members 602 to bias against the centering pin 198 and form a friction fit therewith which retains the head 600 on the driving tool.

Figure 36:
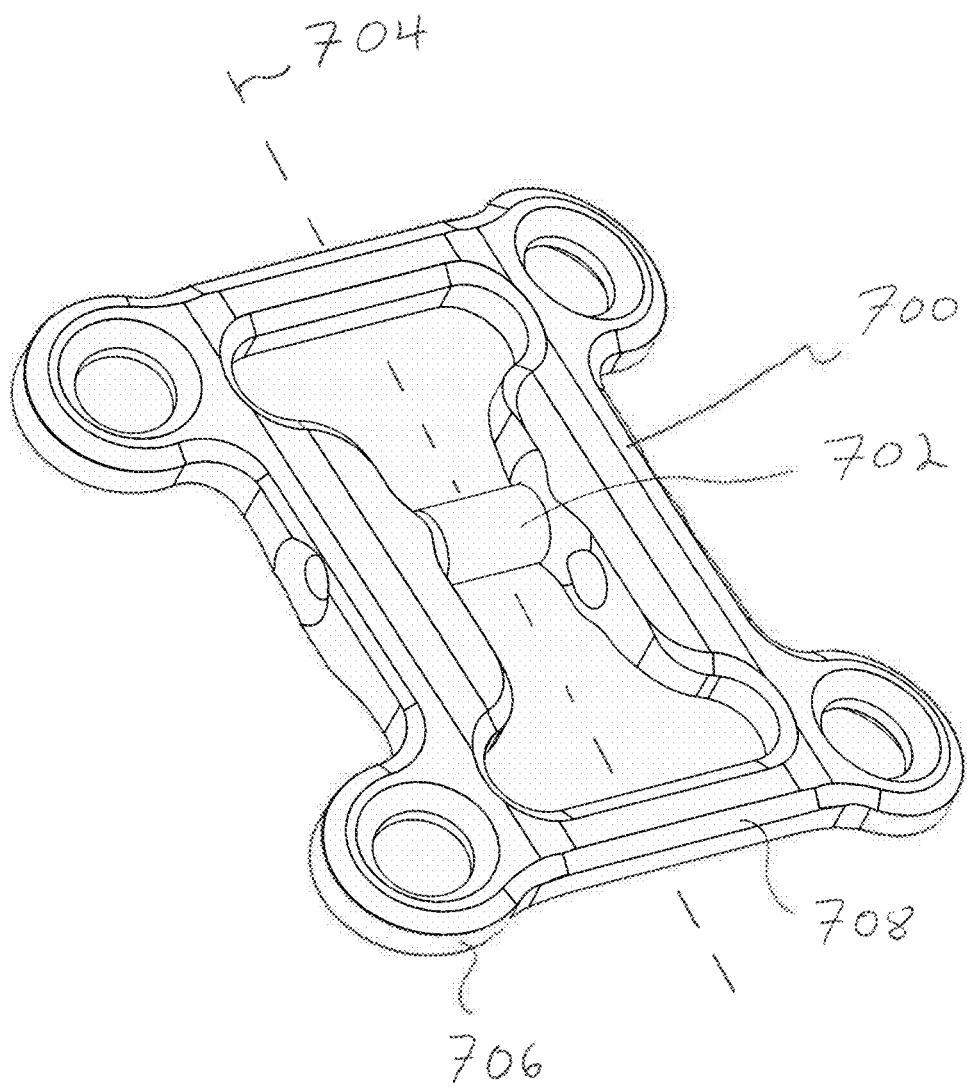
FIG. 36 is a perspective view of the bone plate of FIG. 35.
Figure 37:
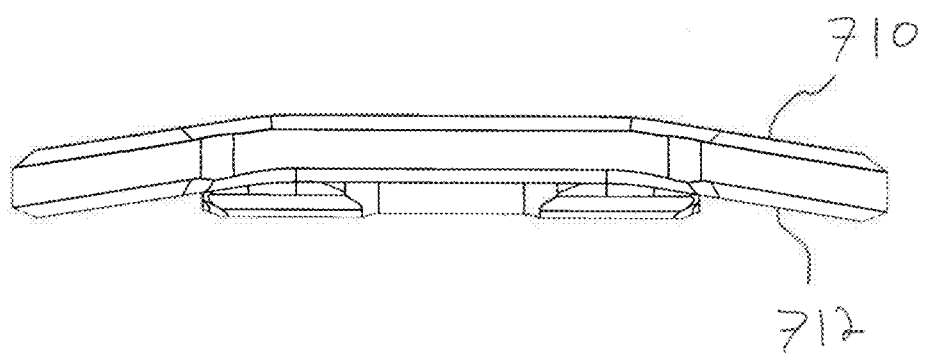
Figure 78:
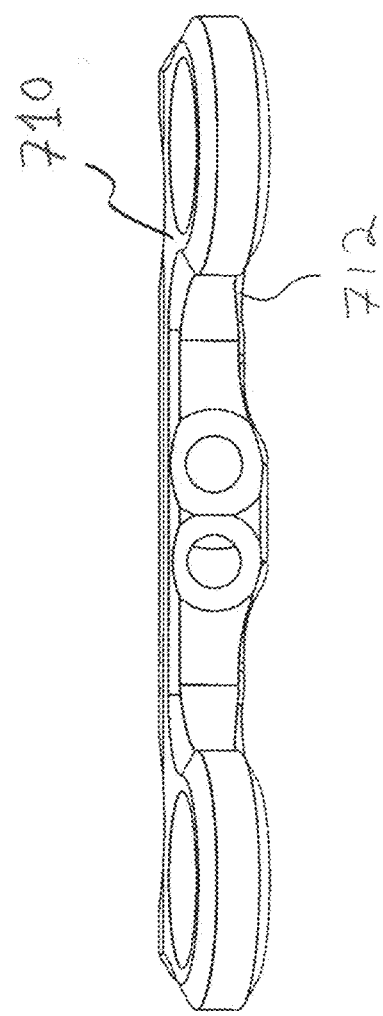

Referring now to FIGS. 36-38, there is illustrated another embodiment of a plate member 700. The bone plate 700 is similar to the bone plate 300 and includes only one locking device 702 disposed at a mid-point of the bone plate 700 along longitudinal axis 704. The bone plate 700 is also similar to the bone plate 300 in that the bone plate 700 is curved slightly about the longitudinal axis 704 such that the bone plate 700 has a convex upper surface 710 and a concave lower surface 712 which permit the bone plate 700 to be flipped to position either the upper surface 710 or the lower surface 712 against the bones depending on whether the bones have a concave or convex outer surface. The bone plate 700 differs from the bone plate 300 in that the bone plate 700 has a substantially rectangular configuration with only one lobe 706 disposed at each of the outermost corners of the bone plate 700 and transverse supports 708 extending across the axis 704 which connect the lobes 706. The more rectangular configuration of the bone plate 700 may be preferred when a plate member having a more compact footprint is desired due to patient anatomy.

Figure 46:
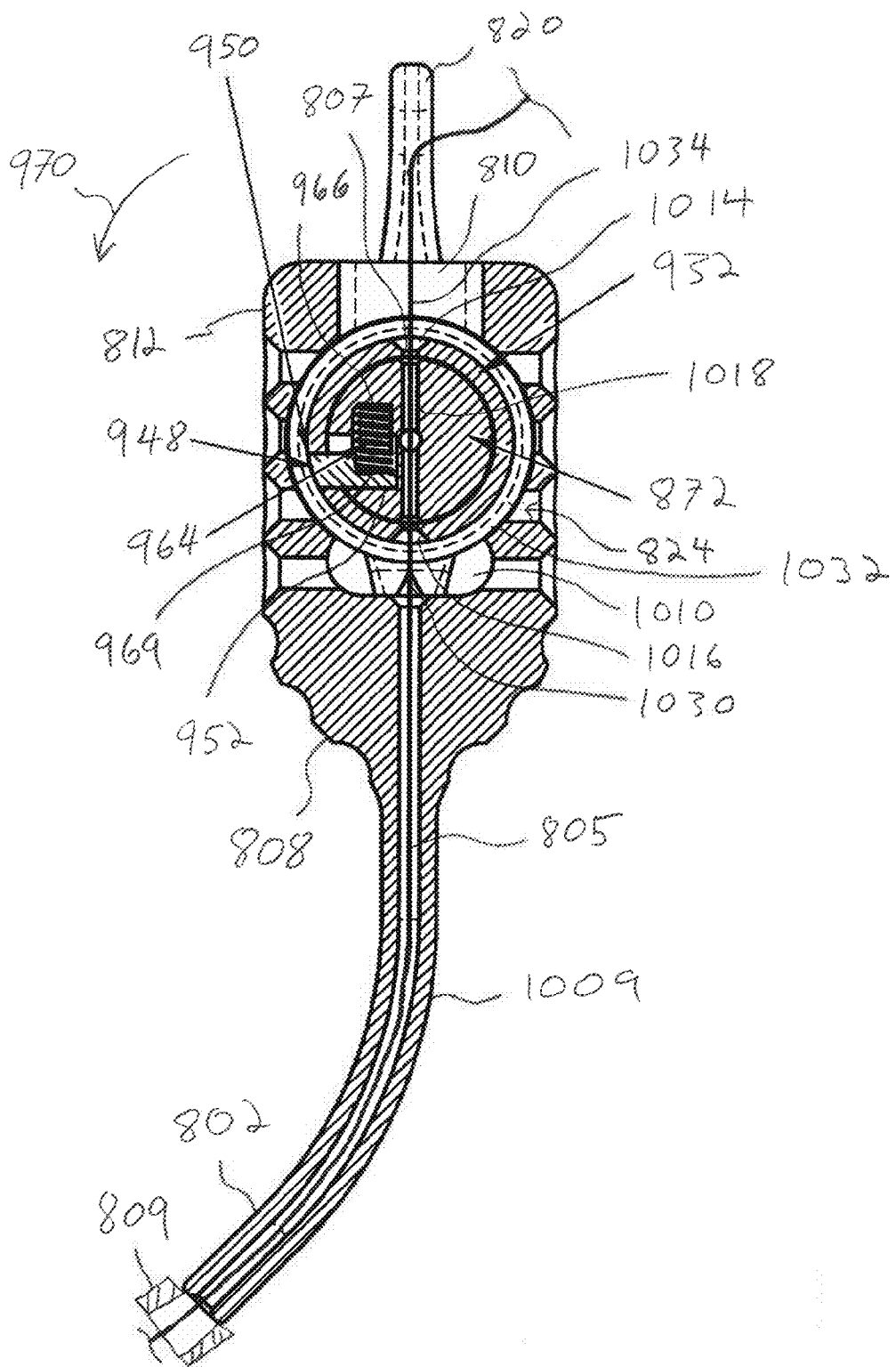
FIG. 46 is a cross sectional view taken across line A-A in FIG. 45 showing a distal end of the tensioning instrument abutting a locking device and a simplified surgical cable extending through the tensioning instrument to illustrate a path of the surgical cable from the locking device through the tensioning instrument.
Figure 47:
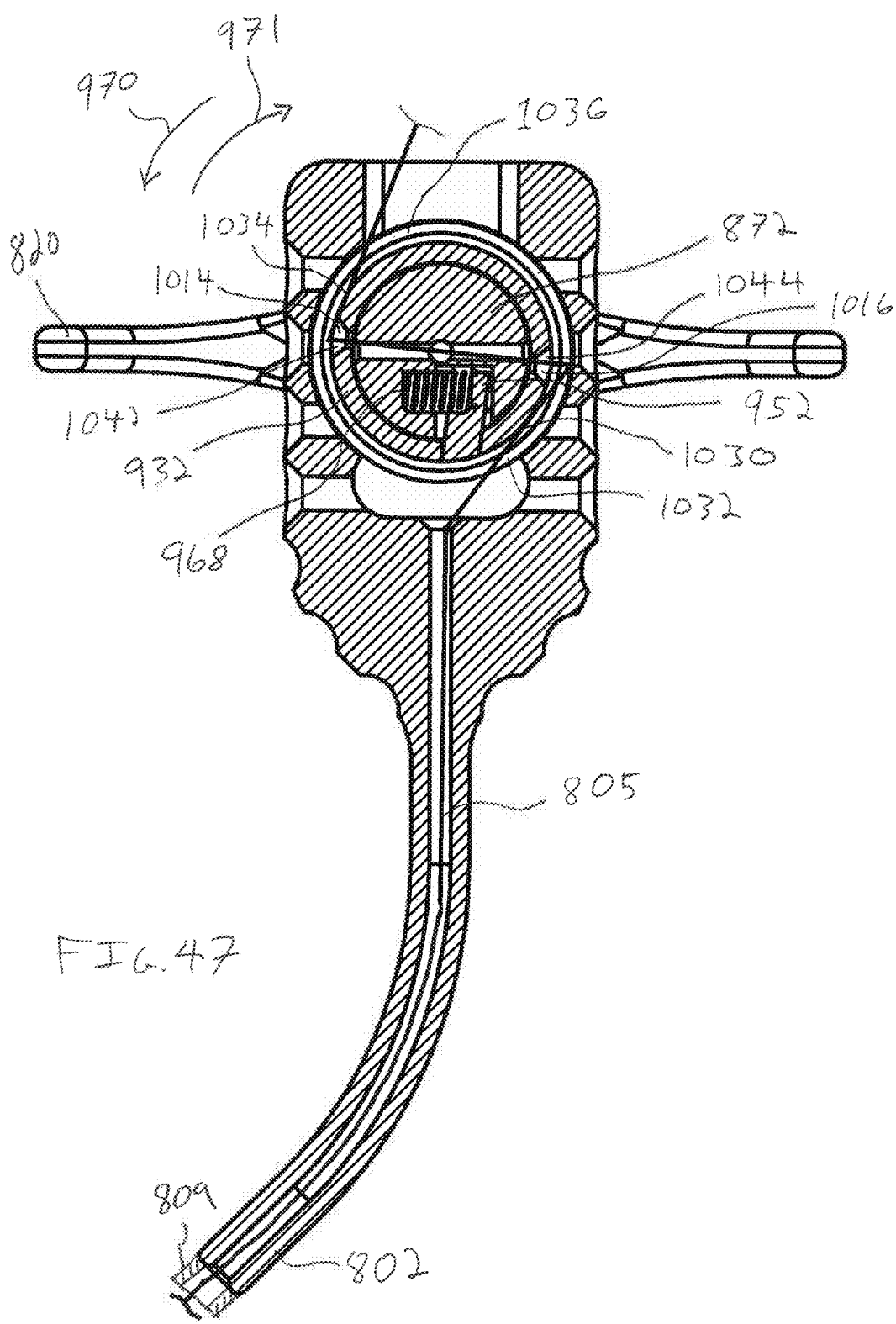
FIG. 47 is a cross sectional view similar to FIG. 46 showing the surgical cable locked to a rotary tensioning device of the tensioning instrument after a handle of the tensioning instrument has been turned ninety degrees.

Turning to FIGS. 39-51, a tensioning instrument 800 is shown that is similar to the tensioning instrument 122 and may be operated in a manner similar to the approach described above with respect to FIGS. 11-14. More specifically, the tensioning instrument 800 has a distal end 802 with an inlet opening 804 sized to permit a surgical cable 805 to be advanced through the inlet opening 804, into a body 808 of the tensioning instrument 800, and through a through opening 807 of a rotary tensioning device 824 within the body 808, as shown in FIG. 46. The surgical cable 805 is advanced in direction 806 until the surgical cable 805 exits the tensioning instrument 800 through an outlet opening 810 at a proximal end 812 of the tensioning instrument 800. With the surgical cable 805 extending outward from the outlet opening 810, a surgeon may move the tensioning instrument 800 along the surgical cable 805 toward the bone plate 20 with one hand and pull any slack out of the surgical cable 805 with the other hand (see FIGS. 12, 13, and 39). The tensioning instrument 800 has a drive 823 including a handle 820 that is configured to be turned in a wind up direction 970 to rotate the rotary tensioning device 824 within the body 808 and cause the surgical cable 805 to be wound up onto the rotary tensioning device 824, as shown in FIG. 47. The tensioning instrument 800 also has a ratchet assembly 826 that selectively restricts rotation of the rotary tensioning device 824 in a pay out direction while permitting a user to incrementally wind the surgical cable 805 onto the rotary tensioning device 824 in the wind up direction 970 (see FIGS. 39 and 46).

Figures 39, 40:
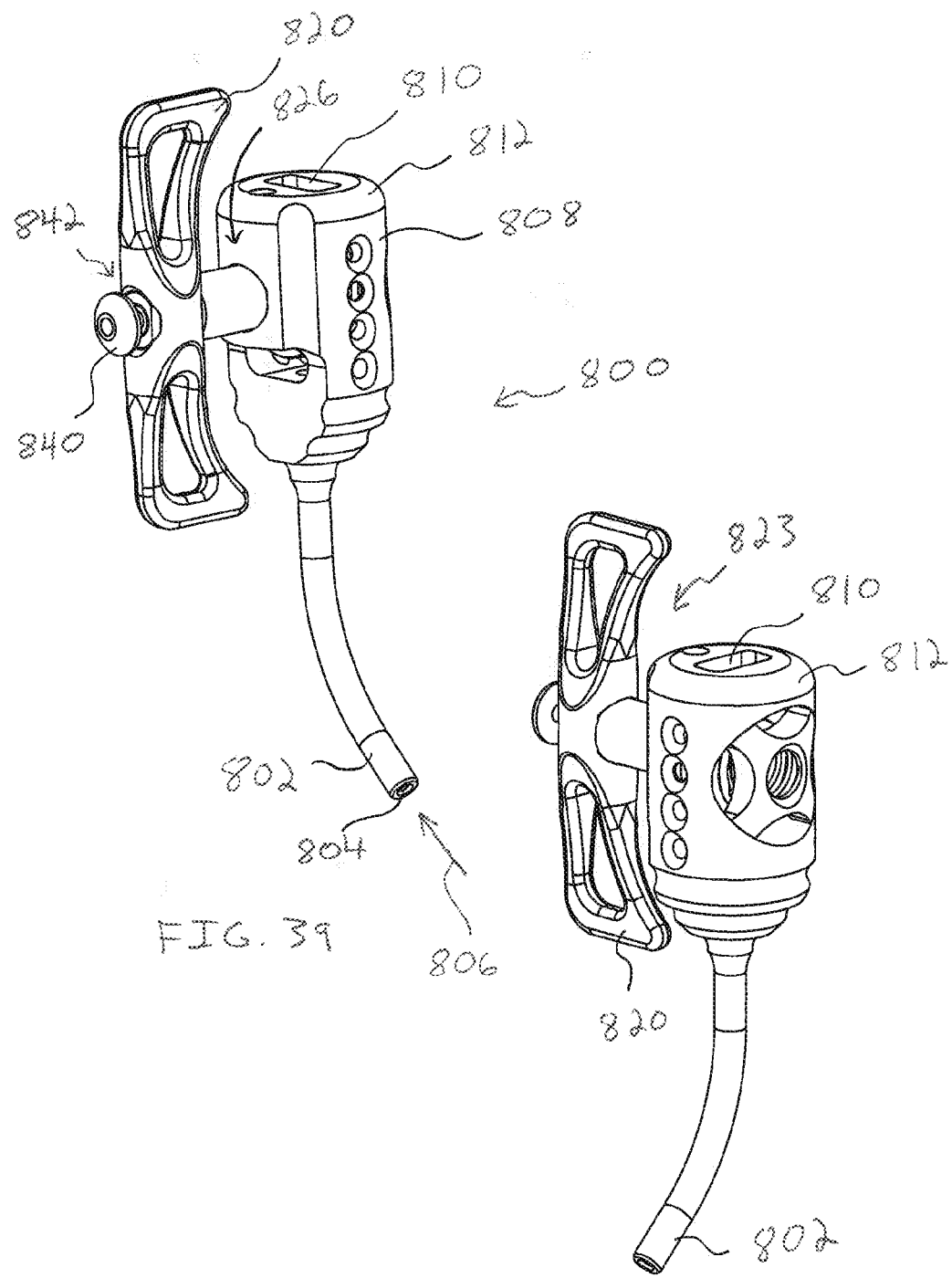
FIGS. 39 and 40 are perspective views of another cable tensioning instrument showing a distal end into which a surgical cable may be advanced and a proximal end with an outlet opening through which the surgical cable is pulled outward therefrom.
Figure 50:
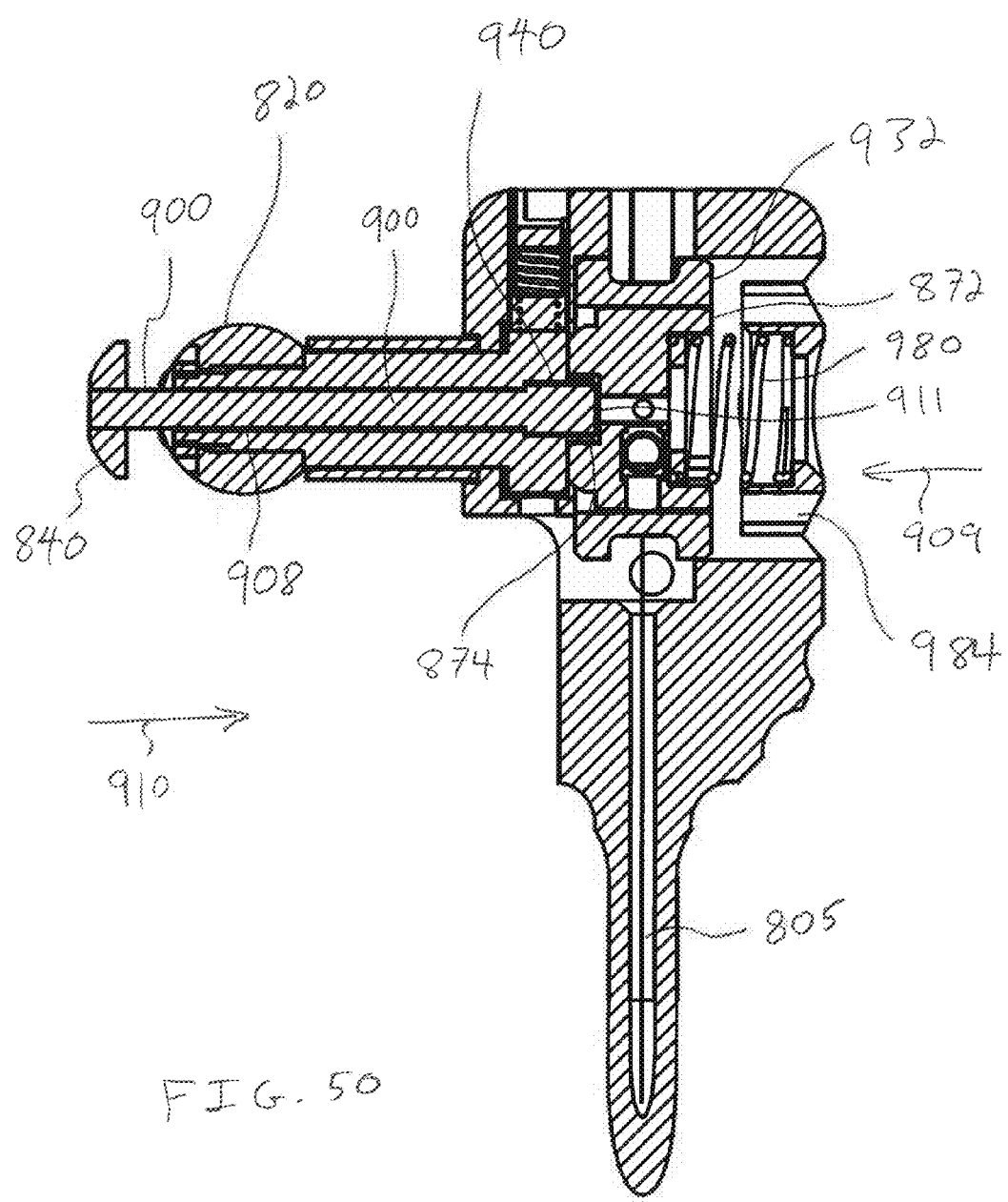
FIG. 50 is a cross sectional view similar to FIG. 49 showing the tension drive and the tension ring rotated after the handle connected to the drive has been turned ninety degrees.
Figure 51:
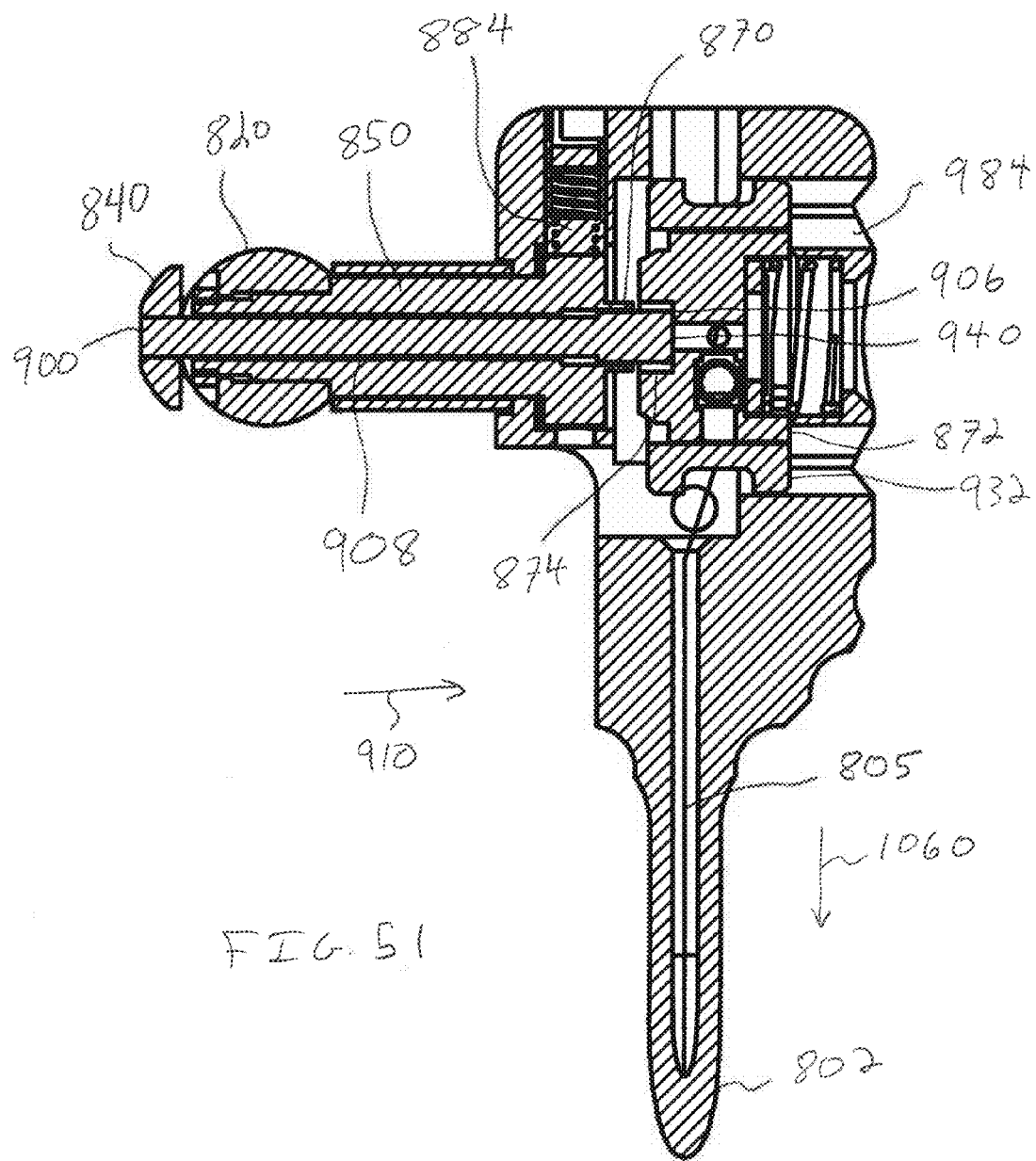
FIG. 51 is a cross sectional view similar to FIG. 50 showing a release button of the handle pressed and a button shaft connected to the release button disengaging the socket of the tension drive from the drive shaft.
Figure 52:
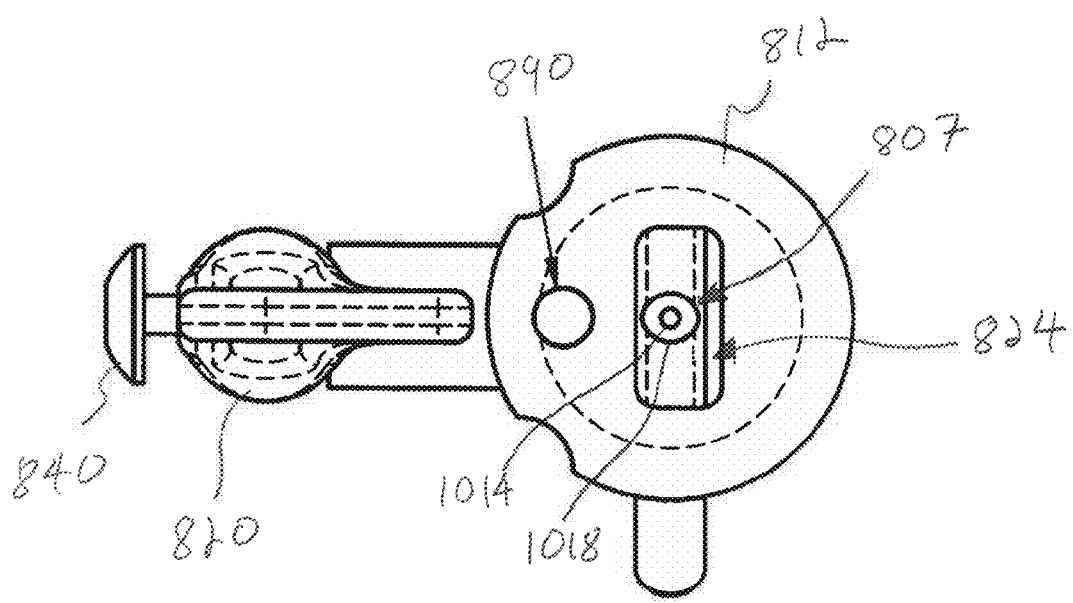
FIG. 52 is a top plan view of the tensioning device showing openings of the tension drive and the tension ring aligned with the outlet opening of the body of the tensioning device when the handle is aligned with a surgical cable path through the tensioning device.

Once a desired amount of tension has been applied to the surgical cable by rotating the drive 823 and the rotary tensioning device 824 connected thereto, a release button 840 of a release mechanism 842 is pressed to disengage the ratchet assembly 826, permit the rotary tensioning device 824 to turn freely in the pay out direction, and allow the tensioning instrument 800 to be pulled off of the surgical cable 805 (see FIGS. 39, 50, and 51). Disengaging the ratchet assembly 826 disconnects the rotary tensioning device 824 from the drive 823 and allows the surgical cable 805 to be unwound from the rotary tensioning device 824, such as by pulling the surgical cable 805 outward from the distal end 802, without rotating the handle 820. In this manner, the tensioning instrument 800 can be removed from the surgical cable 805 without the handle 820 spinning or otherwise interfering with surgery.

Figure 49:
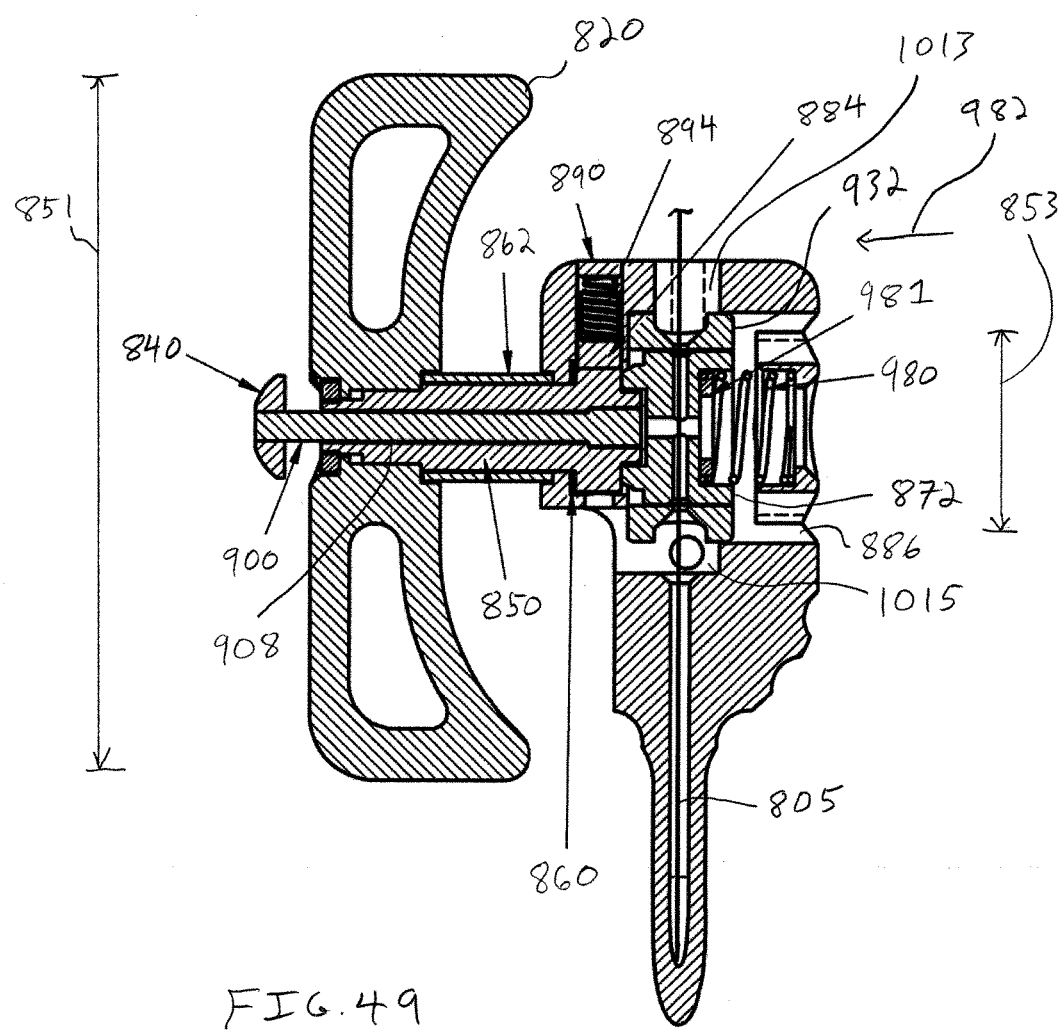
FIG. 49 is a cross-sectional view taken across line B-B in FIG. 48 showing a portion of the drive shaft received in the drive socket of the tension drive so that the drive shaft is in operative engagement with the tension drive.

With reference to FIG. 41, the drive 823 includes a drive shaft 850 having a hex drive 852 for non-rotatably mating with a hex recess 854 of the handle 820 and threads 856 for engaging a shaft nut 858 which fixes the drive shaft 850 to the handle 820. The tensioning instrument 800 has a rotary tensioning device 824 with gripping portions, such as tension drive 872 and tensioning ring 932, which are configured to shift relative to each other and fix a cable to the rotary tensioning device 824. With the drive shaft 850 operatively engaged with a tension drive 872 of the rotary tensioning device 824, turning the handle 820 turns the drive shaft 850 and the tension drive 872 connected thereto, reconfigures the tension drive 872 and the tension ring 932 from a pass-through configuration to a gripping configuration, and draws the surgical cable 805 onto the tension ring 932 carried on the tension drive 872. The direct mechanical connection between the handle 820, the drive shaft 850, and the tension drive 872 provides direct tactile feedback of the tension being applied to the surgical cable 805. Further, the handle 820 has an overall length 851 that is twice a cable-receiving diameter 853 of the tension ring 932, as shown in FIG. 49. This two-to-one relationship balances the ease of turning the handle 820 with providing sufficient tactile feedback regarding the tension in the surgical cable 805, which are both important considerations when tensioning a surgical cable to a particular tension. Although a two-to-one relationship is ideal for many applications, it will be appreciated that ½ to 1, 3 to 1, or other relationships may be desired for other applications. The tensioning instrument 800 also has a sleeve bearing 862 that supports the drive shaft 850 and handle 820 as the handle 820 is turned.

Figure 42:
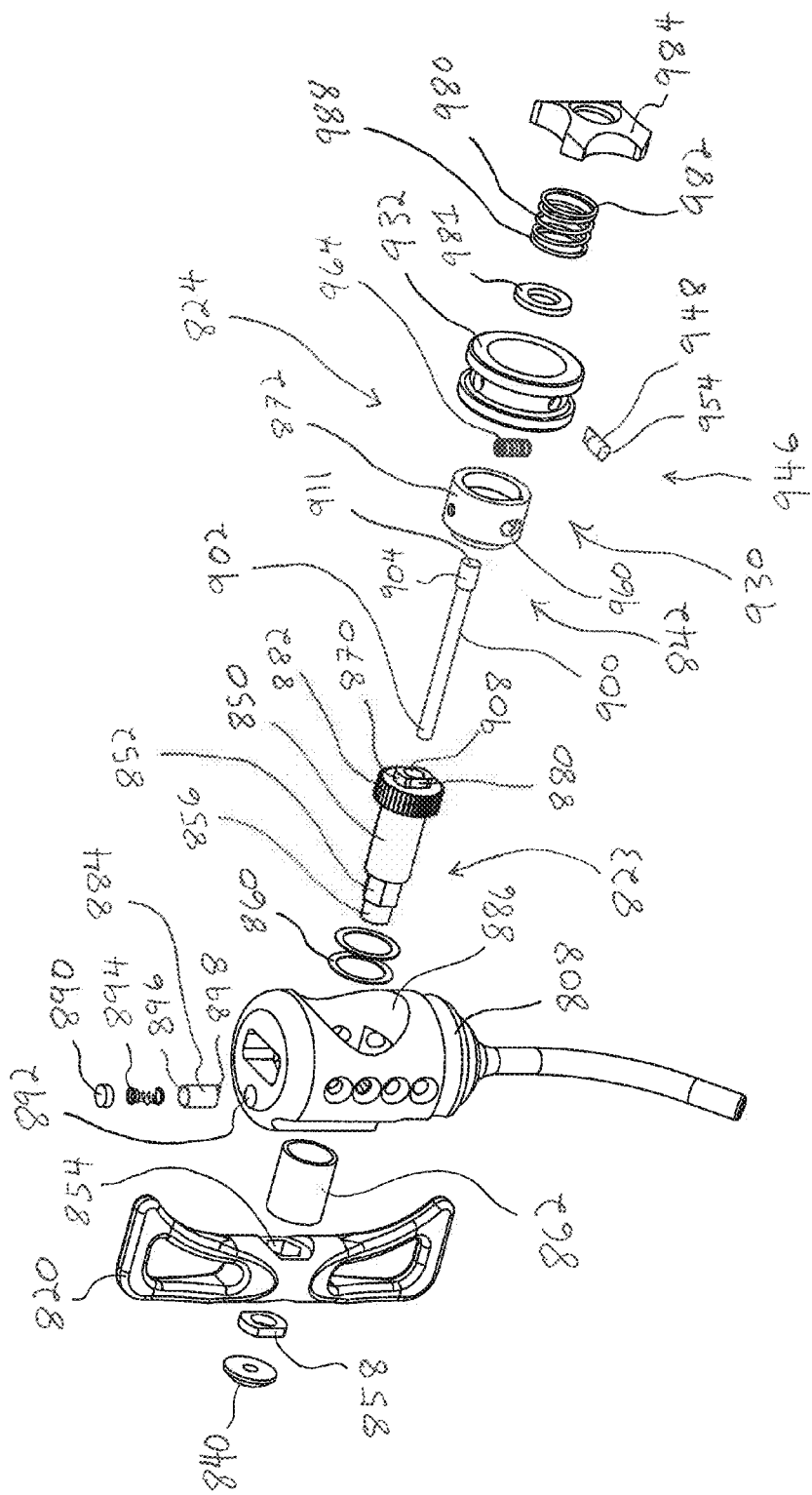
FIG. 42 is a front perspective view of a tension drive of the tensioning instrument of FIG. 39 showing a drive socket of the tension drive.
Figure 41A:
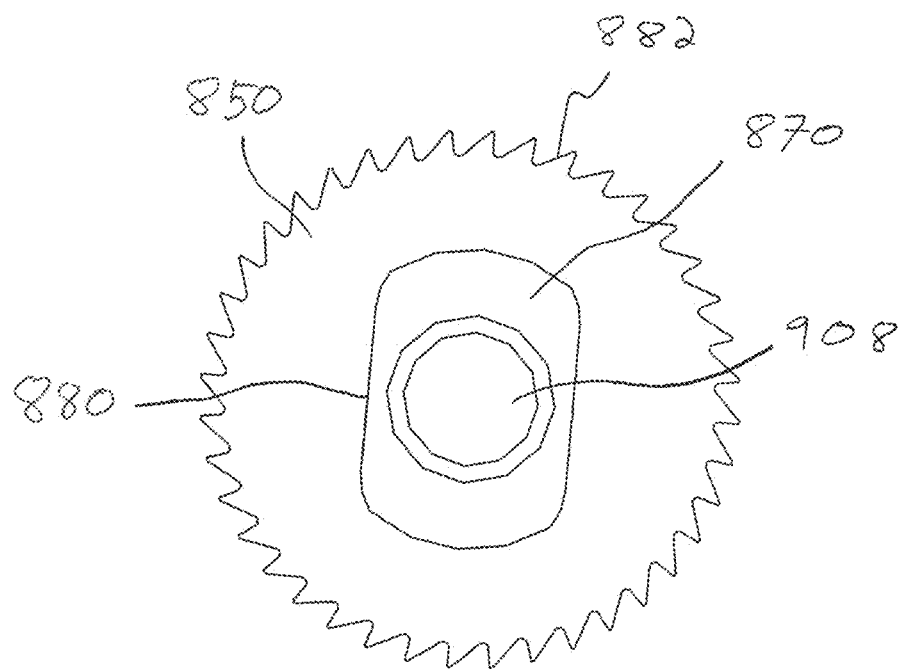
FIG. 41A is an enlarged end elevational view of a drive shaft of the tensioning instrument of FIG. 39.
Figure 42:
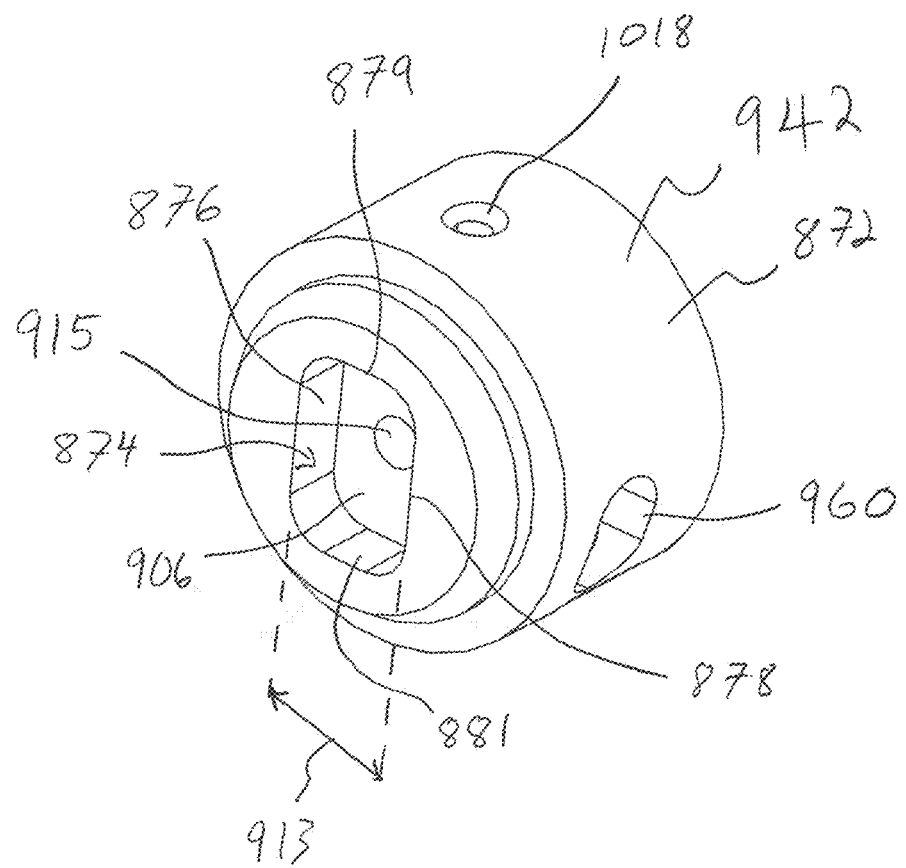
Figure 44:
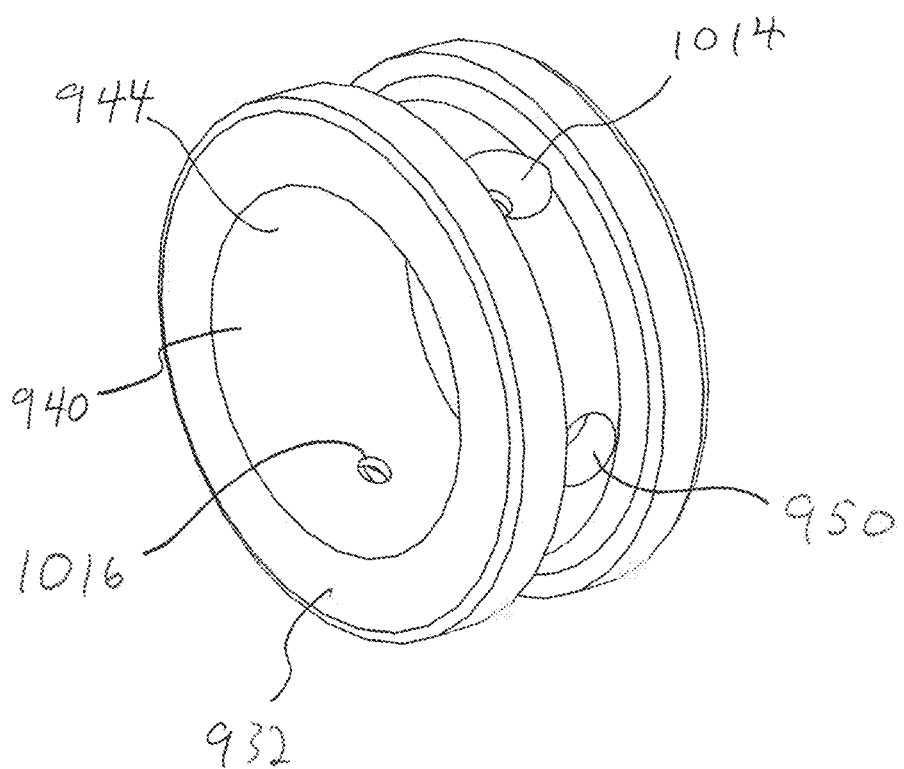
FIG. 44 is a perspective view of the tension ring of the tensioning instrument of FIG. 39 showing a central opening of the tension ring which receives the tension drive.
Figure 45:
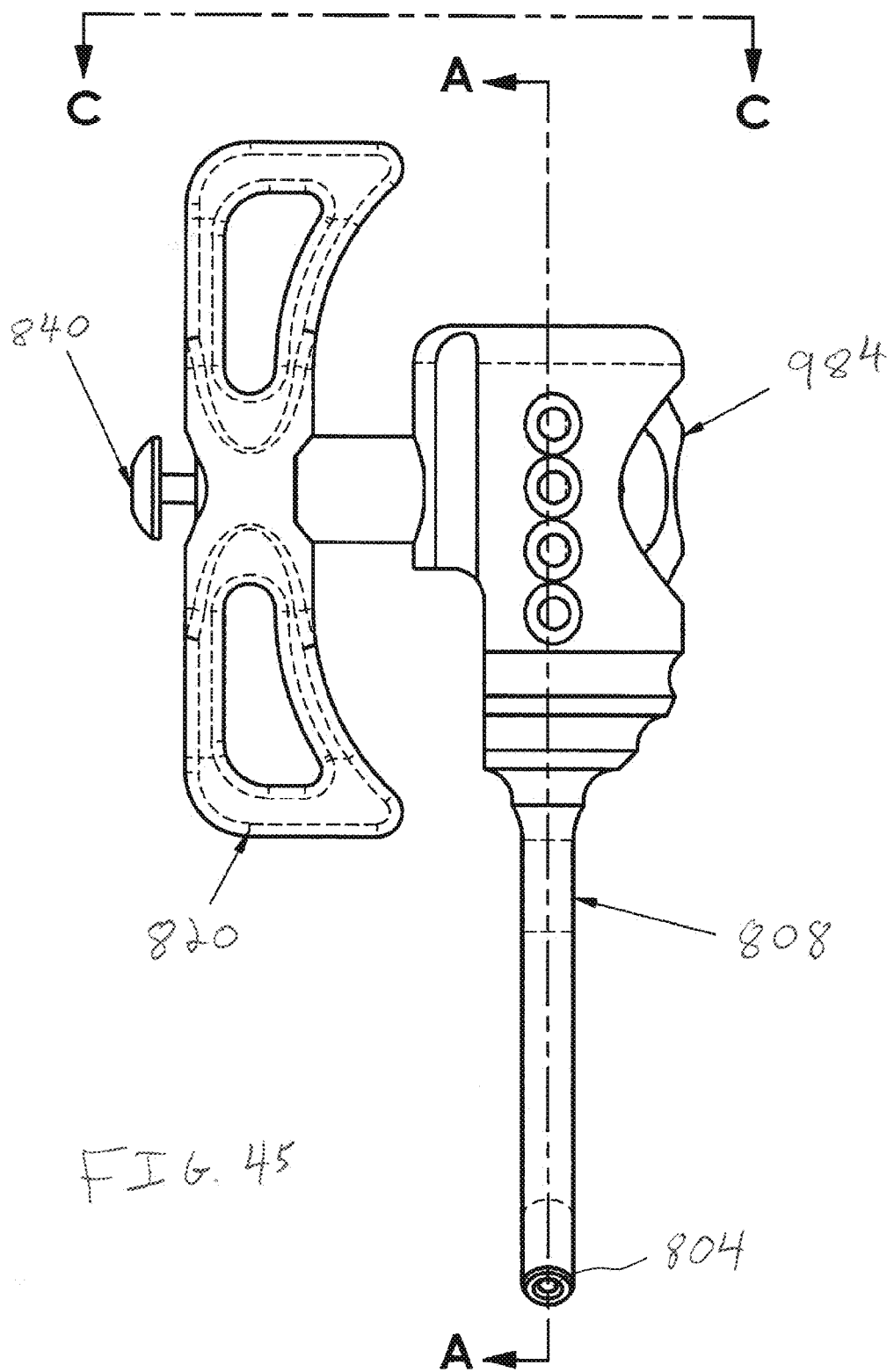
FIG. 45 is an elevational view of the tensioning instrument of FIG. 39 showing an outer profile of a body of the tensioning device.

The tensioning instrument 800 includes structures that align through apertures of the internal components of the tensioning instrument 800 and increase the ease with which the surgical cable 805 can be advanced through the tensioning instrument 800 when the handle 820 is generally aligned with the path of the surgical cable 805 through the body 808 of the tensioning instrument 800, as shown in FIG. 46. More specifically, the through opening 807 of the rotary tensioning device 824 includes a pair of apertures 1014, 1016 of the tension ring 932 and a through opening 1018 of the tension drive 872 that are aligned when the tension ring 932 and the tension drive 872 are in the pass-through configuration, as shown in FIGS. 42, 44, and 46. To ensure that the tension drive through opening 1018 is oriented to permit the surgical cable 805 to be advanced therethrough, the drive shaft 850 has a generally rectangular oblong key 870 at one end thereof for engaging the tension drive 872, as shown in FIGS. 41 and 41A. The tension drive 872 has a complementary generally rectangular oblong drive socket 874 (see FIG. 42) for transmitting torque from the handle 820 and drive shaft 850 to the tension drive 872 and the tension ring 932 carried thereon. The oblong drive socket 874 includes spaced, generally flat sidewalls 876, 878 in a vertical orientation (as shown in FIG. 42) parallel with a through opening 1018 of the tension drive 874 through which the surgical cable 805 is advanced. The socket 874 also has shorter sidewalls 879, 891 in a horizontal orientation perpendicular to the through opening 1018. Because the key 870 and the socket 874 are both oblong, the key 870 and the socket 874 fit together in only two orientations that are 180° apart from each other. In either orientation, the handle 820 is aligned with the through opening 1018 of the tension drive 872 when the drive shaft key 870 is engaged with the tension drive socket 874. Thus, when the drive shaft 850 is engaged with the tension drive 872 and the handle 820 is in a vertical orientation (see FIG. 46), the through opening 1018 of the tension drive 872 will be aligned with the path of the surgical cable 805 through the body 808. As discussed in greater detail below, the tensioning instrument 800 has a bias assembly 946 that maintains the tension ring 932 in a pass-through position about the tension drive 872 where the tension ring apertures 1014, 1016 are aligned with the tension drive through opening 1018. In this manner, the surgical cable 805 can be quickly and easily advanced through the tension ring apertures 1014, 1016 and the tension drive through opening 1018 when the handle 820 is aligned with the path of the surgical cable 805 through the tensioning instrument 800.

The drive shaft 850 also has a ratchet portion 882 with ratchet teeth configured to engage a pawl 884 and restrict rotation of the drive shaft 850 in a pay out direction, as shown in FIGS. 41 and 49. The pawl 884 is disposed within an opening 892 of the body 808 and is aligned with the ratchet portion 882 of the drive shaft 850 when the drive shaft 850 has been inserted into a cavity 886 of the body and secured to the handle 820. With reference to FIG. 41, the tensioning instrument 800 includes a plug 890 welded or otherwise secured to the body 808 to close the opening 892 and restrict removal of the pawl 884 from within the opening 892. The opening 892 is sized to permit up and down movement of the pawl 884 and a spring 894 is positioned between the plug 890 and the pawl 884 to bias the pawl 884 downwardly into engagement with the teeth of the ratchet portion 882 of the drive shaft 850. The pawl 884 has a tooth 898 at a leading end thereof for engaging and restricting rotation of the teeth of the ratchet portion 882 when the drive shaft 850 is rotated in a pay out direction 971 and permitting rotation of the teeth of the ratchet portion 882 when the drive shaft 850 is rotated in the wind up direction 970 (see FIG. 47). In one form, the plug 890 has an downwardly extending fin that engages a slot on a trailing end 896 of the pawl 884. The fin restricts rotation of the pawl 884 relative to the plug 890 and keeps the tooth 898 of the pawl 884 aligned with the teeth of the ratchet portion 882.

To disengage the tension drive 872 from the drive shaft 850, the tensioning instrument 800 has a release shaft 900 with a button end 902 connected to the button 840 and a plunger end 904 configured to abut a receiving surface 906 of the drive socket 874, as shown in FIGS. 41 and 42. The release shaft 900 is slidably received with a throughbore 908 of the drive shaft 850 and is biased in direction 909 by a spring 980, as shown in FIG. 50. Pressing the button 840 in direction 910 shifts the release shaft 900, tension drive 872, and the tension ring 932 in direction 910, as shown in FIG. 51. The plunger end 904 has a circular, flat pusher surface 911 with a diameter thereacross that is less than a width 913 of the drive socket 874 between sidewalls 876, 878 but larger than an opening 915 in the receiving surface 906, as shown in FIGS. 41 and 42. The clearance between the plunger end 904 and the socket sidewalls 876, 878, 879, 881 and the sliding contact between the pusher surface 911 and the receiving surface 906 allows the tension drive 872, and the tension ring 932 carried thereon, to rotate about the plunger end 904 once the release shaft 900 has shifted the tension drive 872 out of engagement with the drive shaft 850, as shown in FIG. 51. The tension drive 872 and the tension ring 932 may then be rotated by the tension in the surgical cable 805 as the tension is released after disengagement of the drive shaft 850 and the tension drive 872.

The tensioning instrument 800 includes a cable gripping mechanism 930 that locks onto the surgical cable 805 with rotation of the handle 820, as shown in FIGS. 41, 46, and 47. In one form, the cable gripping mechanism 930 includes the tension drive 872 and the tension ring 932 disposed coaxially thereon. When the tension drive 872 is rotated by turning the handle 820, the tension drive 872 shifts rotationally within a central opening 940 of the tension ring 932 and causes a circular outer surface 942 of the tension drive 872 to slide along an annular inner surface 944 of the tension ring 932, as shown in FIGS. 42, 44, 46, and 47. Shifting the tension ring 932 about the tension drive 872 causes the tension drive 872 and the tension ring 932 to fix the tension drive 872 and the tension ring 932 to the surgical cable 805, as discussed in greater detail below. With the tension drive 872 and the tension ring 932 fixed to the surgical cable 805, continued turning of the handle 820 continues to turn the tension drive 872 and the tension ring 932, further winds the surgical cable 805 onto the tension ring 932, and further tensions the surgical cable 805.

The cable gripping mechanism 930 also includes the bias assembly 946 configured to limit relative rotation between the tension drive 872 and the tension ring 932 and return the tension ring 932 to the pass through orientation about the tension drive 872. The bias assembly 946 has a tension pin 948 sized to fit within a pin aperture 950 of the tension ring 932 and a base 954 secured to the tension ring 932 to fix the tension pin 948 to the tension ring 932, as shown in FIGS. 41, 44, and 46. The base 954 is preferably welded or otherwise secured to the tension ring 932 after the tension drive 872 has been positioned within the central opening 940 of the tension ring 932. Further, the tension pin 948 may extend radially inward from the tension ring 932 with a tension ring tooth 952 disposed within a pin slot 960 in an outer wall 962 of the tension drive 872 (see FIGS. 42, 43, and 46). The engagement between the tension pin 948 and the pin slot 960 captures the tension drive 872 within the central opening 940 of the tension ring 932 while permitting a predetermined amount of relative rotary motion therebetween.

Figure 43:
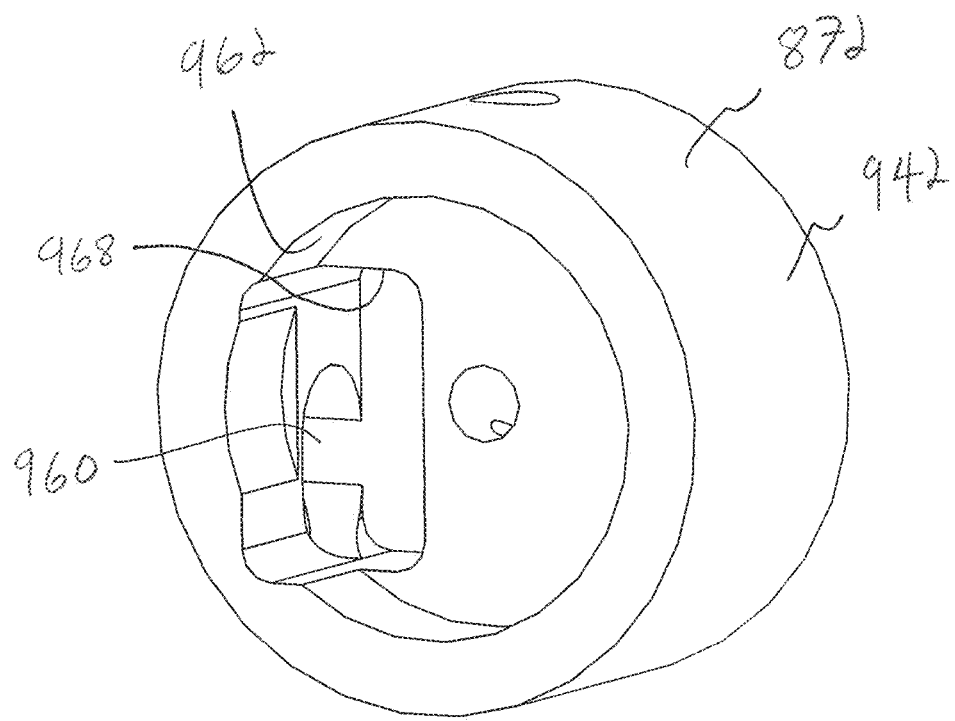
FIG. 43 is a rear perspective view of the tension drive of FIG. 42 showing a recess for receiving a pin connected to a tension ring of the tensioning device of FIG. 39.

With reference to FIGS. 43 and 46, the bias assembly 946 further includes a spring 964 having an end 966 for engaging a spring seat 968 of the tension drive 872 and an opposite end 969 abutting the tooth 952 of the tension pin 948. The pin slot 960 extends along a circumference of the outer wall 962 a distance that is longer than a diameter of the tension pin 948 to permit the tension pin 948 to slide within the slot 960 as the tension drive 872 moves rotationally relative to the tension ring 932. More specifically, movement of the tension drive 872 in direction 970 brings spring seat 968 toward the tooth 952 of the tension pin 948 and compresses the spring 964, as shown in FIG. 47. The compressed spring 964 provides a restoring force that tends to shift the tension ring 932 in direction 970 and re-align apertures 1014, 1016 of the tension ring 932 with the through opening 1018 of the tension drive 872 once tension has been released from the surgical cable 805, such as after a locking device 809 has been crimped to secure the surgical cable 805 around bones and the drive shaft 850 has been disengaged from the tension drive 872. In this manner, the cable gripping mechanism 930 may automatically release the surgical cable 805 and permit the surgical cable 805 to be withdrawn from the tensioning instrument 800 after tension has been released in the surgical cable 805.

Figure 48:
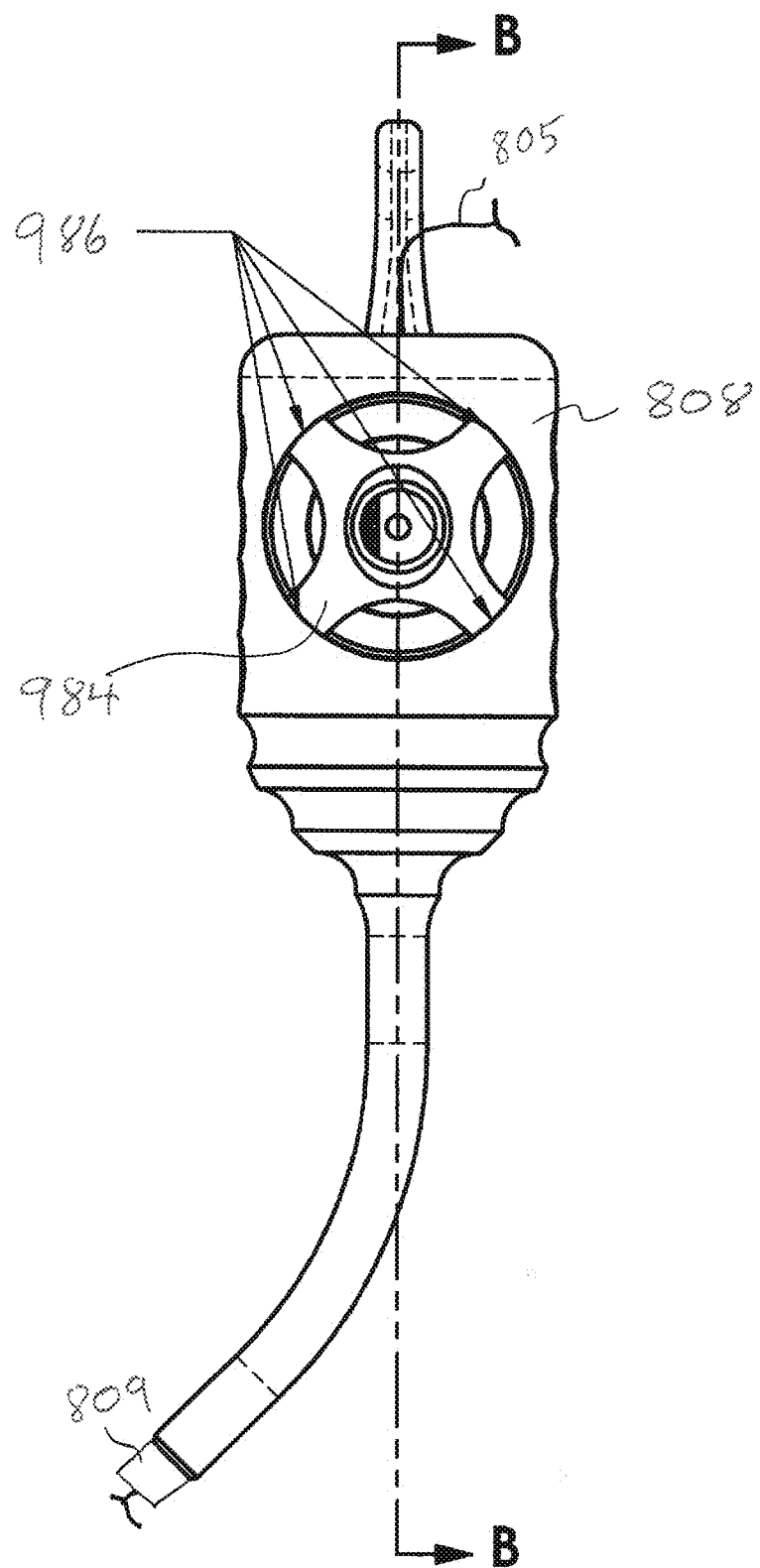
FIG. 48 is an elevational view of the tensioning instrument of FIG. 39 showing a cap welded to the body of the tensioning instrument to secure components of the tensioning instrument within the body.

The release mechanism 842 includes the spring 980 having one end 982 abutting a cap 984 welded to the body 808 at points 986, as shown in FIG. 48, and an opposite end 988 abutting a washer 981 for biasing the tension drive 872 in direction 982, as shown in FIG. 49. The spring 980 biases the washer 981 against the tension drive 872 and maintains the tension drive socket 874 firmly engaged with the drive shaft key 870. To overcome the bias force of the spring 980 and disengage the tension drive socket 874 from the drive shaft key 870, the release button 840 is pressed to shift the release shaft 900 in direction 910 which moves the tension drive 872 in direction 910, as discussed in greater detail above and shown in FIGS. 50 and 51.

The operation of the tensioning instrument 800 is substantially identical to the operation of the tensioning instrument 122 such that the following description of the operation of the tensioning instrument 800 will begin at the point where the surgical cable 805 has been advanced through the distal end 802 of the tensioning instrument 800, out from the proximal end 812, and pulled tightly to remove slack from the surgical cable, as shown in FIG. 46. More specifically, with the handle 820 in the vertical orientation and tension drive 872 and the tension ring 932 in the pass through configuration shown in FIG. 46, the surgical cable 805 may be readily advanced through the opening 807 of the rotary tensioning device 824 and out the outlet opening 810. The surgical cable 805 extends through a guide tube 1009 of the distal end 802, upward beyond an aperture 1010 in the body 808, through the opening 807 of the rotary tensioning device 824, and outward through the outlet opening 810, as shown in FIG. 46. The aperture 1010 allows a surgeon to view the surgical cable 805 within the body 808 which may be useful when advancing the surgical cable 805 into the through opening 807 of the rotary tensioning device 824.

The handle 820 is then turned in the wind up direction 970 to substantially simultaneously fix the cable gripping mechanism 930 to the surgical cable 805 at two positions along the surgical cable 805 as well as tension the surgical cable 805 by winding the surgical cable 805 onto the rotary tensioning device 824. The handle 820 is shown in FIG. 47 as having been rotated a quarter turn in the wind up direction 970 to illustrate the operation of the internal components of the tensioning instrument 800. It will be appreciated that the handle 820 may be turned farther to continue to take up the surgical cable 805 onto the tension ring 932. Further, the cavity 886 of the body 808 includes gaps 1013, 1015 disposed radially between the tension ring 932 and the body 808 that are sized to provide clearance between coils of the surgical cable 805 and the body 808 as the surgical cable 805 is drawn onto the tension ring 932, as shown in FIG. 49. These gaps 1013, 1015 permit relatively long sections of the surgical cable 805 to be wound around the tension ring 932 with continued turning of the handle 824.

Turning the handle 820 in the wind up direction 970 rotates the tension drive 872 in direction 970 and causes a surgical cable distal section 1030 to be drawn onto a lower portion 1032 of the tension ring 932 and a surgical cable proximal section 1034 to be drawn onto an upper portion 1036 of the tension ring 932. Drawing the surgical cable distal section 1030 onto the tension ring 932 tensions the surgical cable 28 between the tension ring 932 and the distal end 802 of the tensioning tool 800 which is positioned against the locking device 809. The tension in the surgical cable 805 shifts the tension ring 932 in direction 971 relative to the tension drive 872 and causes the tension ring 932 to pinch the surgical cable 805 at intersections 1042, 1044 between the apertures 1014, 1016 of the tension ring 932 and the central through opening 1018 of the tension drive 872, as shown in FIG. 47. Further, shifting of the tension ring 932 about the tension drive 872 moves the spring seat 968 toward the tension pin 952 and compresses the spring 964.

Once a desired amount of tension has been applied to the surgical cable 805, and the pawl 884 resisting turning of the drive shaft 850 in the pay out direction 971, the surgical cable 805 is secured in position such as by crimping the locking device 809. Next, the release button 840 is pressed in direction 910 to shift the release shaft 900 in direction 910, as shown in FIGS. 50 and 51. The plunger end 940 presses against the receiving surface 906 (see FIG. 42) of the drive socket 874, shifts the tension drive 872 and the tension ring 932 in direction 910, and shifts the tension drive socket 874 out of engagement with the drive shaft key 870. In this position, the tension drive 872 and the tension ring 932 may rotate in the pay out direction 971 relative to the drive shaft 850 so that any tension previously applied to the surgical cable 805 by turning of the handle 820 is released from the surgical cable 805. Further, with the release button 840 depressed, the surgical cable 805 can be withdrawn in direction 1060 from the distal end 802 of the tensioning instrument 800, as shown in FIG. 51. Because the tension drive 872 and tension ring 932 are disconnected from the drive shaft key 870, pulling the surgical cable 805 in direction 1060 off of the tension ring 932 causes the tension drive 872 and the tension ring 932 to rotate about the plunger end 940 in pay out direction 971 and permits the surgical cable 805 to be paid out from the tension ring 932. Once the surgical cable 805 has been withdrawn from the tensioning instrument 800, the tensioning instrument 800 can be removed from the surgical site and the surgical cable 805 cut to length as desired.

Figure 53:
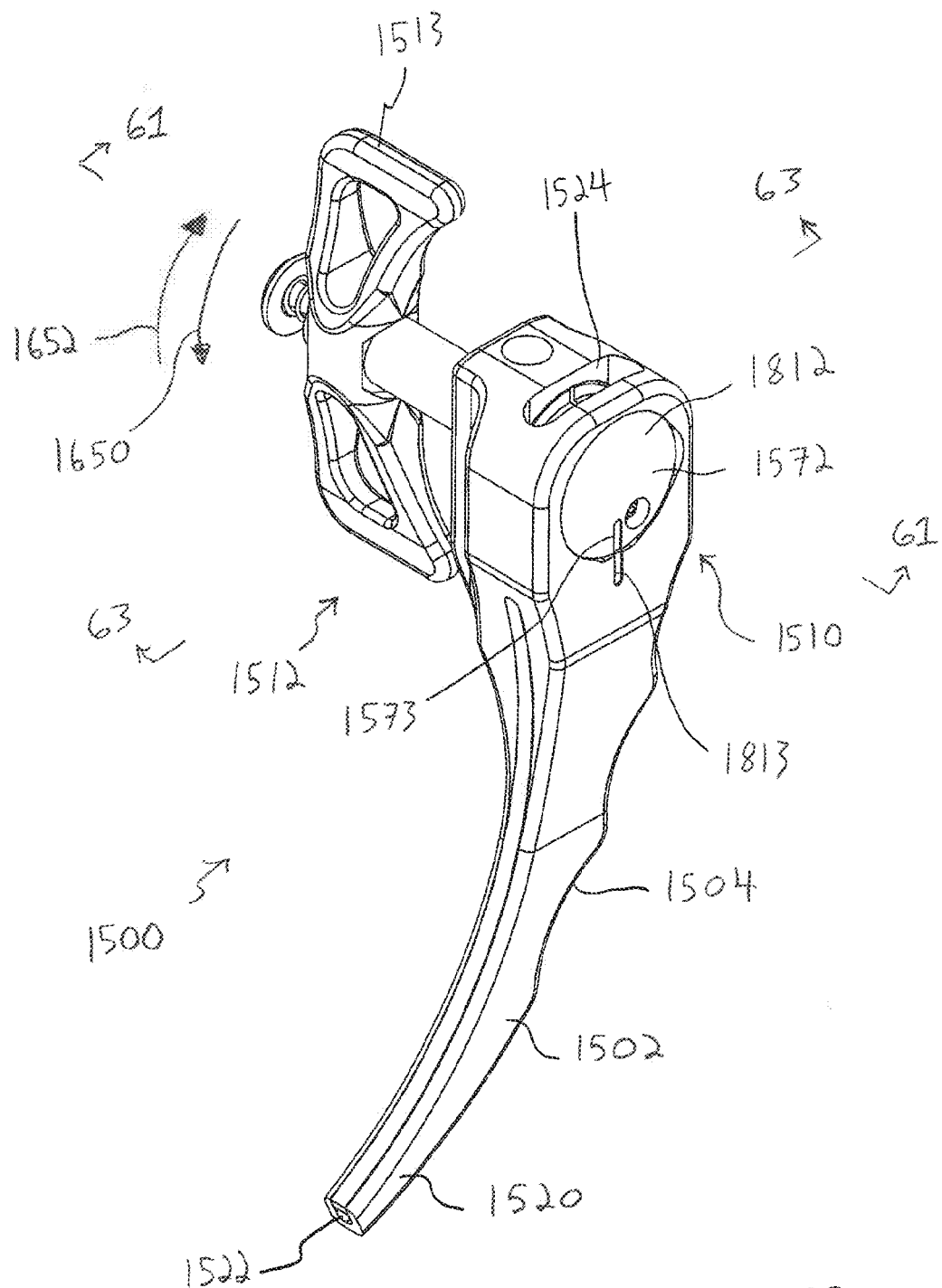
FIG. 53 is a perspective view of another cable tensioning instrument.
Figure 62:
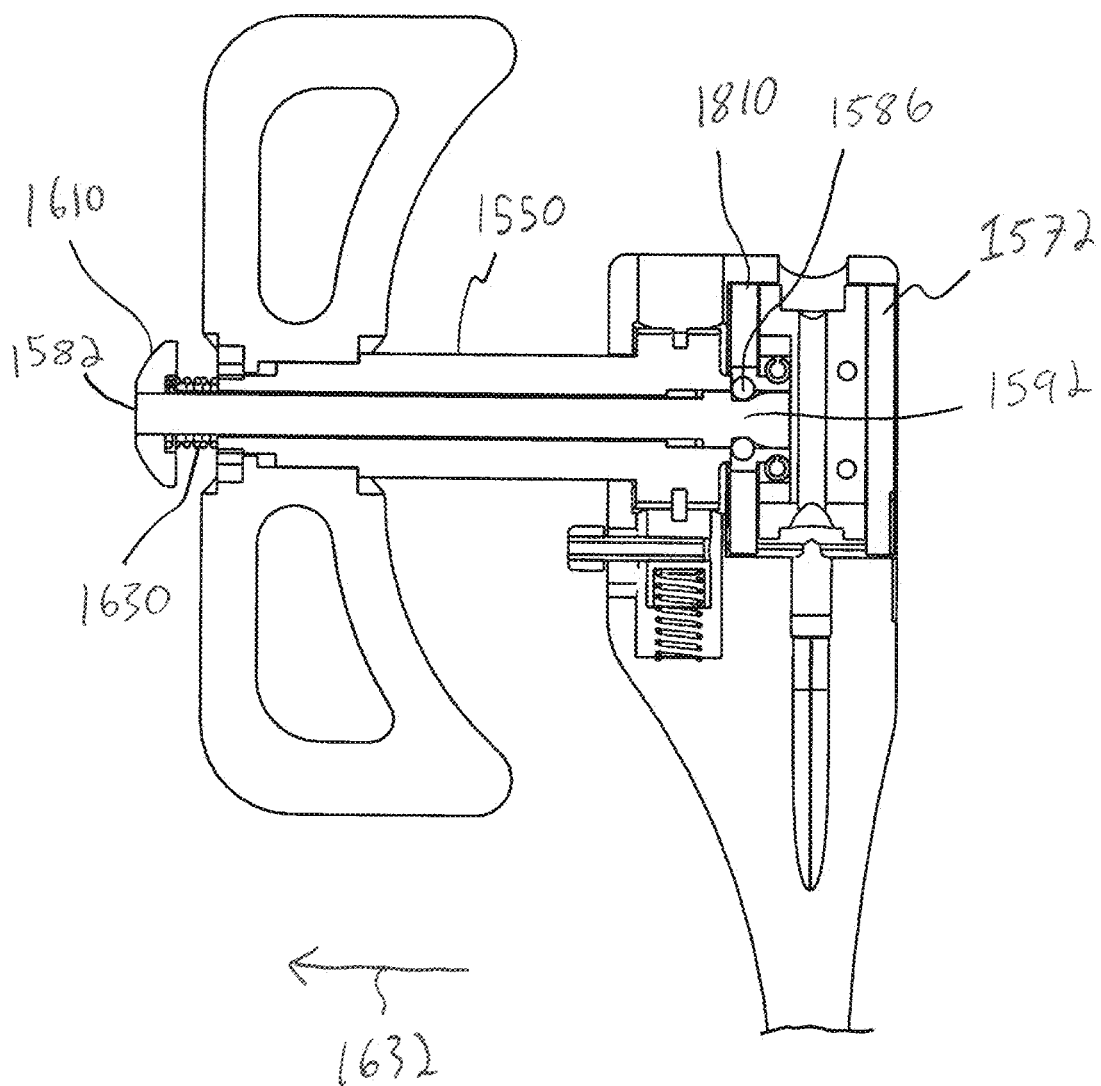
FIG. 62 is a cross-sectional view similar to FIG. 61 showing the release shaft head shifted out of alignment with the ball bearings which permits the ball bearings to shift inwardly and disengage the drive shaft from the tension drive.
Figure 63:
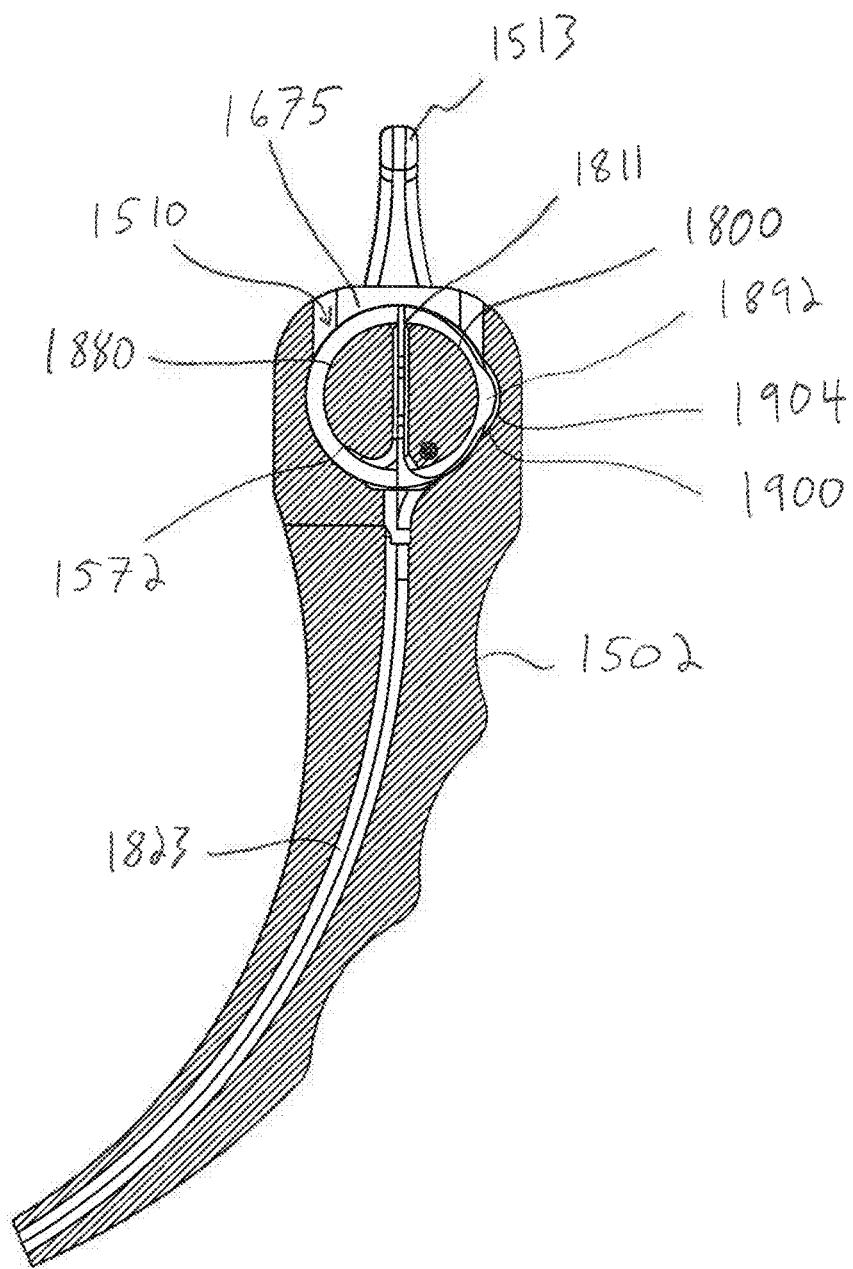
FIG. 63 is a cross-sectional view taken across line 63-63 in FIG. 53 and shows a through passage of a body of the tensioning instrument that is aligned with a through opening formed between the tension drive and the clamp member.

With reference to FIGS. 53-65, a cable tensioning instrument 1500 is shown that permits rapid and easy-to-use tensioning of surgical cable 24. The tensioning instrument 1500 has a body 1502 with a scalloped profile 1504 and a rotary tensioning device 1510 with a tension drive 1572 that is partially visible from outside of the body 1502, as shown in FIG. 53. The instrument 1500 has a drive 1512 including a handle 1513 coupled to the rotary tensioning device 1510 so that turning of the handle 1513 produces associated turning of the rotary tension device 1510 (and tension drive 1572 with etch mark 1573 thereon). With reference to FIGS. 53 and 63, the body 1502 has a distal end 1520 with an inlet opening 1522, a proximal outlet opening 1524, a passage 1823 (see FIG. 63) extending therebetween, and a through opening 1811 of the rotary tensioning device 1510. In a manner similar to the use of the tensioning instrument 122 discussed above with reference to FIGS. 10-13, the leading end portion 28 of the cable 24 is inserted into the inlet opening 1522, along the passage 1823 and through the opening 1811, and outward from the body outlet opening 1522 in order to initially connect the tensioning instrument 1500 to the cable 24.

With the cable 24 extending through the tensioning instrument 1500, a surgeon may move the tensioning instrument 1500 along the surgical cable 24 toward the bone plate 20 with one hand and pull any slack out of the surgical cable 24 with the other hand, as discussed above with respect to tensioning instruments 122 and 800. Next, the handle 1513 is turned to turn the rotary tensioning device 1510 and wrap cable 24 onto the rotary tensioning device 1510. Turning the rotary tensioning device 1510 within the body 1502 reconfigures the grip device 1514 from a pass-through configuration where the cable 24 may be advanced through the rotary tensioning device opening 1811 between the tension drive 1572 and the clamp body 1800 (see FIGS. 63 and 64), to a gripping configuration where the tension drive 1572 and clamp body 1800 are shifted together and clamp the cable 24 (see FIG. 65). Continued turning of the handle 1513 continues to wrap cable onto the rotary tensioning device 1510 while the tension drive 1572 and clamp body 1800 fix the cable 24 to the rotary tensioning device 1510. This turning of the rotary tensioning device 1510 while maintaining the 1572 and clamp body 1800 fixed on the cable 24 applies tension to the cable 24.

It will be appreciated that the tensioning instrument 1500 is similar in many respects to the structure and operation of the tensioning instruments 122, 800 discussed above such that the following discussion will highlight differences between the instrument 1500 and the instruments 122, 800. For example, the rotary tensioning device 1510 has a grip device 1514 (see FIG. 54) that clamps the cable 24 between faces 1820 (see FIG. 58), 1870 (see FIG. 60) of the tension drive 1572 and a clamp body 1800 rather than clamping a cable between the portions of tension ring 932 and tension drive 872 as in the instrument 800 (see FIGS. 46 and 47).

Figure 54:
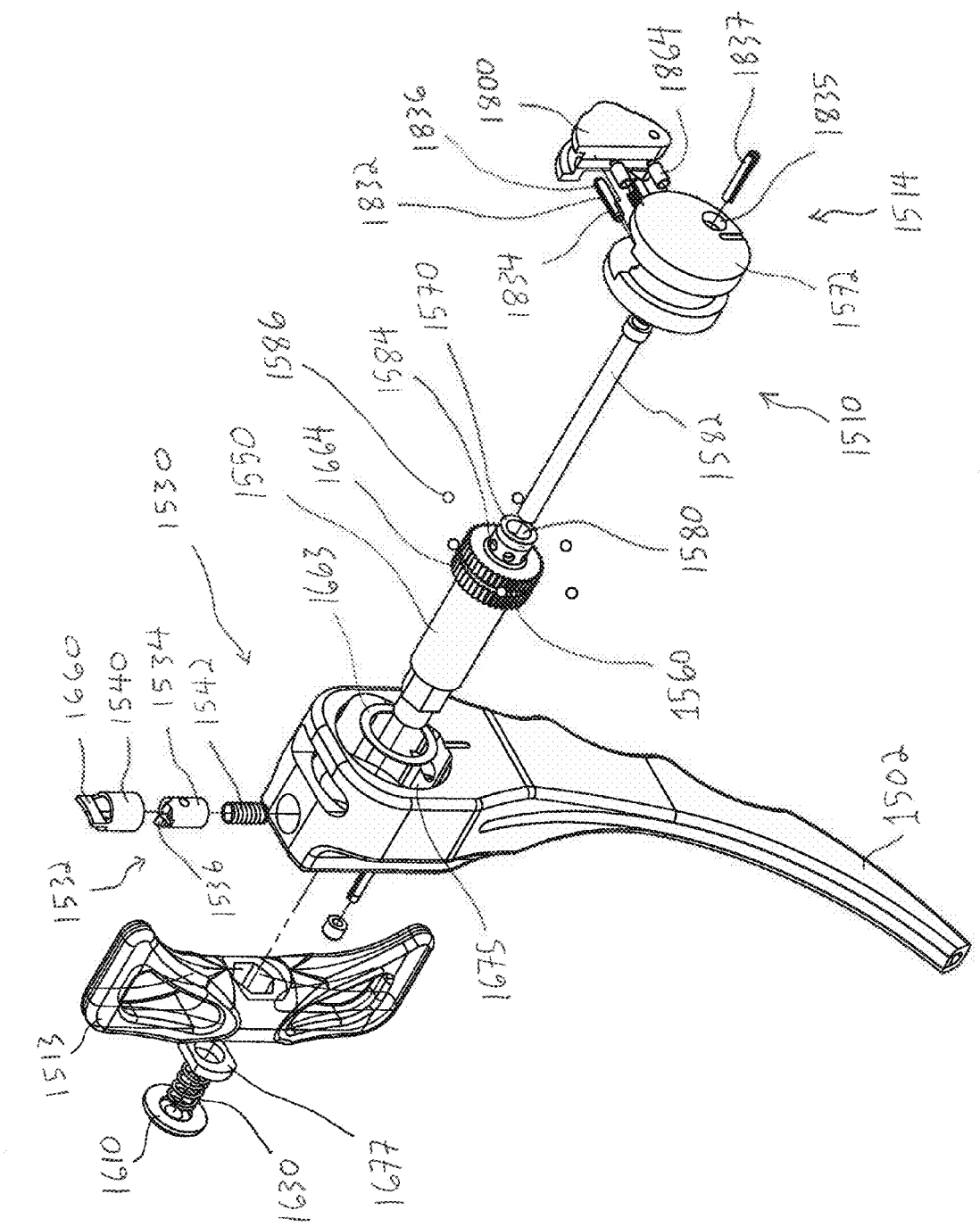
FIG. 54 is an exploded perspective view of the tensioning instrument of FIG. 53.

With reference to FIG. 54, the tensioning instrument 1500 includes a ratchet assembly 1530 configured to selectively permit turning of the rotary tensioning device 1510. The ratchet assembly 1530 includes a pawl assembly 1532 having a pawl 1534 with a split tooth 1536, the pawl 1534 being slidably received within a pawl sleeve 1540. The pawl 1534 is longitudinally movable within the pawl sleeve 1540 and is biased by a spring 1542 into engagement with a drive shaft 1550 (which is secured at its other end to the handle 1513). The pawl tooth 1536 engages teeth 1664 on a ratchet portion 1560 of the drive shaft 1550, as shown in FIG. 54. As will be discussed in greater detail below, the ratchet assembly 1530 has a different configuration than the ratchet assembly 826 in order to provide different assembly and disassembly of the instrument 1500.

Figure 56:
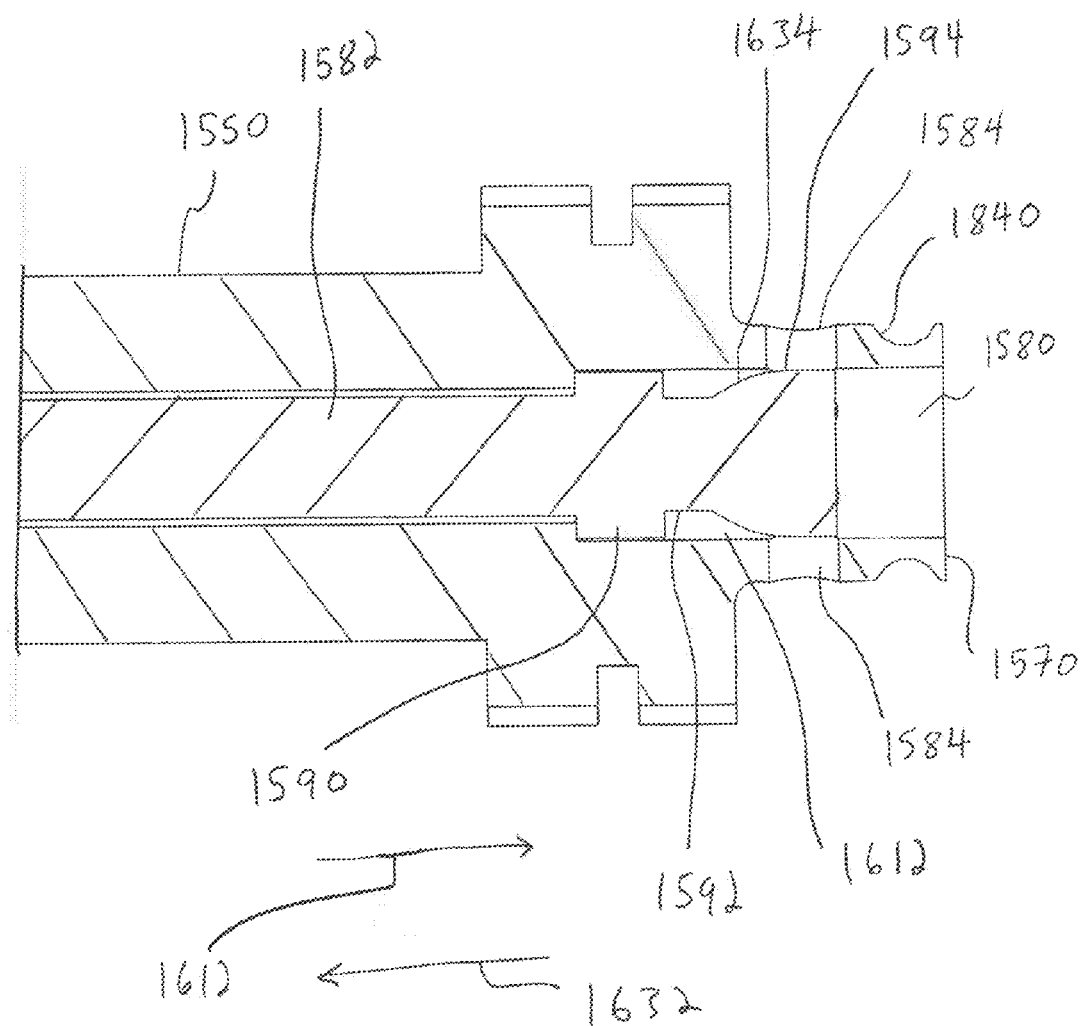
FIG. 56 is a partial cross-sectional view of a release shaft of the tensioning instrument disposed in the drive shaft.

The tensioning instrument 1500 also has a different connection between the drive shaft 1550 and the rotary tension device 1510 than the components of the tensioning instrument 800. In particular, the drive shaft 1550 has a drive portion 1570 that is selectively engaged via ball bearings 1586 with the tension drive 1572 of the rotary tension device 1510. With reference to FIGS. 54 and 56, the drive shaft 1550 has an inner throughbore 1580 with a release shaft 1582 slidably disposed therein. The drive shaft drive portion 1570 includes radially outwardly extending openings 1584 (see FIG. 56) that receive the ball bearings 1586 and are sized to permit the ball bearings 1586 to shift inwardly and outwardly within the openings 1584 based upon the position of the release shaft 1582. As shown in FIG. 56, the release shaft 1582 has an enlarged collar 1590, a neck 1592, and an enlarged head 1594 at a distal end thereof. The head portion 1594 has an outer diameter sized to fill substantially the entire throughbore 1580 and shift a portion of each of the ball bearings 1586 outwardly into pockets 1600 (see FIG. 57 and FIG. 61).

Figure 61:
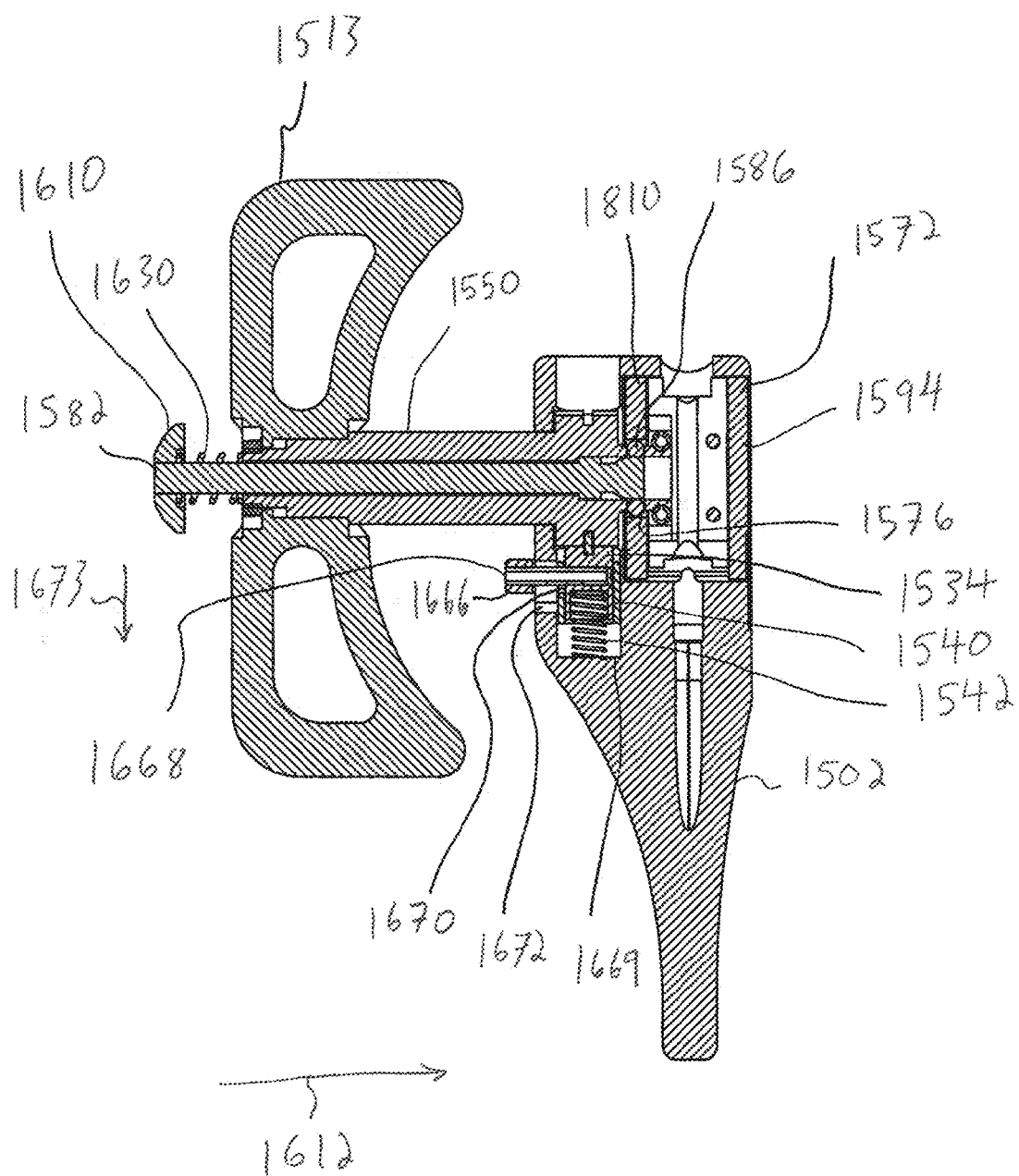
FIG. 61 is a cross-sectional view taken across line 61-61 in FIG. 53 showing the drive shaft connected to the socket of the tension drive and a head of the release shaft aligned with ball bearings in the drive shaft drive portion.

With the drive shaft drive portion 1570 engaged in the socket 1576 and the ball bearings 1586 shifted outward by the release shaft head 1590 into engagement with the pockets 1600, turning of the drive shaft 1550 produces turning of the tension drive 1572, as shown in FIG. 61. For example, if the handle 1513 is turned in a wind up direction 1650 to apply tension to the cable 24 once the cable 24 has been advanced through the instrument 1500 (see FIG. 53), the drive shaft 1550 will turn in the wind up direction 1650 while the cable 24 will resist the tensioning and tend to turn the tension drive 1572 in a pay out direction 1652. However, a section of each ball bearing 1586 is disposed in the drive shaft openings 1584 while the remaining section extends outward into the tension drive pockets 1600. The ball bearings 1586 are thereby engaged with both the drive shaft drive portion 1570 and the tension drive socket 1576 and inhibit relative movement between the drive shaft 1550 and the tension drive 1572. Thus, turning the handle 1512 and drive shaft 1550 in the wind up direction 1650 with sufficient torque produces turning of the tension drive 1572 (and clamp body 1800 connected thereto) and applies tension to the cable 24. It will be appreciated that the ball bearings 1586 are preferably made of a sufficiently hard material to resist the shearing loads applied to the ball bearings 1586 by the tension drive 1572 and the drive shaft 1550.

To disengage the drive shaft 1550 from the tension drive 1572, a button 1610 connected to the release shaft 1582 is pressed to shift the release shaft 1582 in direction 1612 toward a release position, as shown in FIG. 61. This aligns the neck 1592 of the release shaft 1582 with the radially extending openings 1584 of the drive shaft drive portion 1570, as shown in FIG. 62. Moving the neck 1592 into alignment with the openings 1584 moves a gap 1612 between the drive shaft 1550 and the release shaft 1582 into communication with the openings 1584 which permits the ball bearings 1586 to shift inwardly. To aid the ball bearings 1586 in shifting inwardly, the pockets 1600 of the tension drive 1572 have curved inner surfaces 1620 (see FIG. 57) that engage outer surfaces 1622 (see FIG. 55) of the ball bearings 1586 and cam the ball bearings 1586 radially inward upon turning of the now-disengaged tension drive 1572 about the drive shaft drive portion 1570. For example, once the button 1610 has been pressed in direction 1612 and the shaft 1582 shifted to its release position, tension in the cable 24 may turn the tension drive 1572 in the payout direction 1652 because the ball bearings 1586 are no longer held in the outwardly biased position by the release shaft 1582. The resulting turning of the now-disengaged tension drive 1572 about the drive shaft drive portion 1570 causes the pocket surfaces 1620 to cam the bearings 1586 radially inward into the gap 1612 to provide clearance for the tension drive 1572 about the drive shaft drive end 1570.

The ratchet assembly 1530 includes a spring 1630 that biases against the button 1610 and shifts the release shaft 1582 backward in direction 1632, as shown in FIG. 62. Shifting the release shaft 1582 backward returns the release shaft 1582 to its engaging position and re-aligns the release shaft head 1594 with the ball bearings 1586 to shift the ball bearings 1586 back into engagement with the tension drive socket pockets 1600. With reference to FIG. 56, the release shaft 1582 has a tapered cam surface 1634 extending outwardly from the neck 1592 toward the enlarged head 1594. The cam surface 1634 is configured to engage the ball bearings 1586 and cam the ball bearings 1586 radially outward within the openings 1584 upon return of the release shaft 1582 in direction 1632. This aids in returning the ball bearings 1586 to their engaged position within the drive shaft socket pockets 1600. With the release shaft 1582 returned to its engaged position, as shown in FIG. 61, turning of the handle 1513 in the wind up direction 1650 will again produce corresponding turning of the tension drive 1572 and the clamp body 1800 in the wind up direction 1650 and apply tension to the cable 24 if the cable 24 is present in the instrument 1500.

Figure 55:
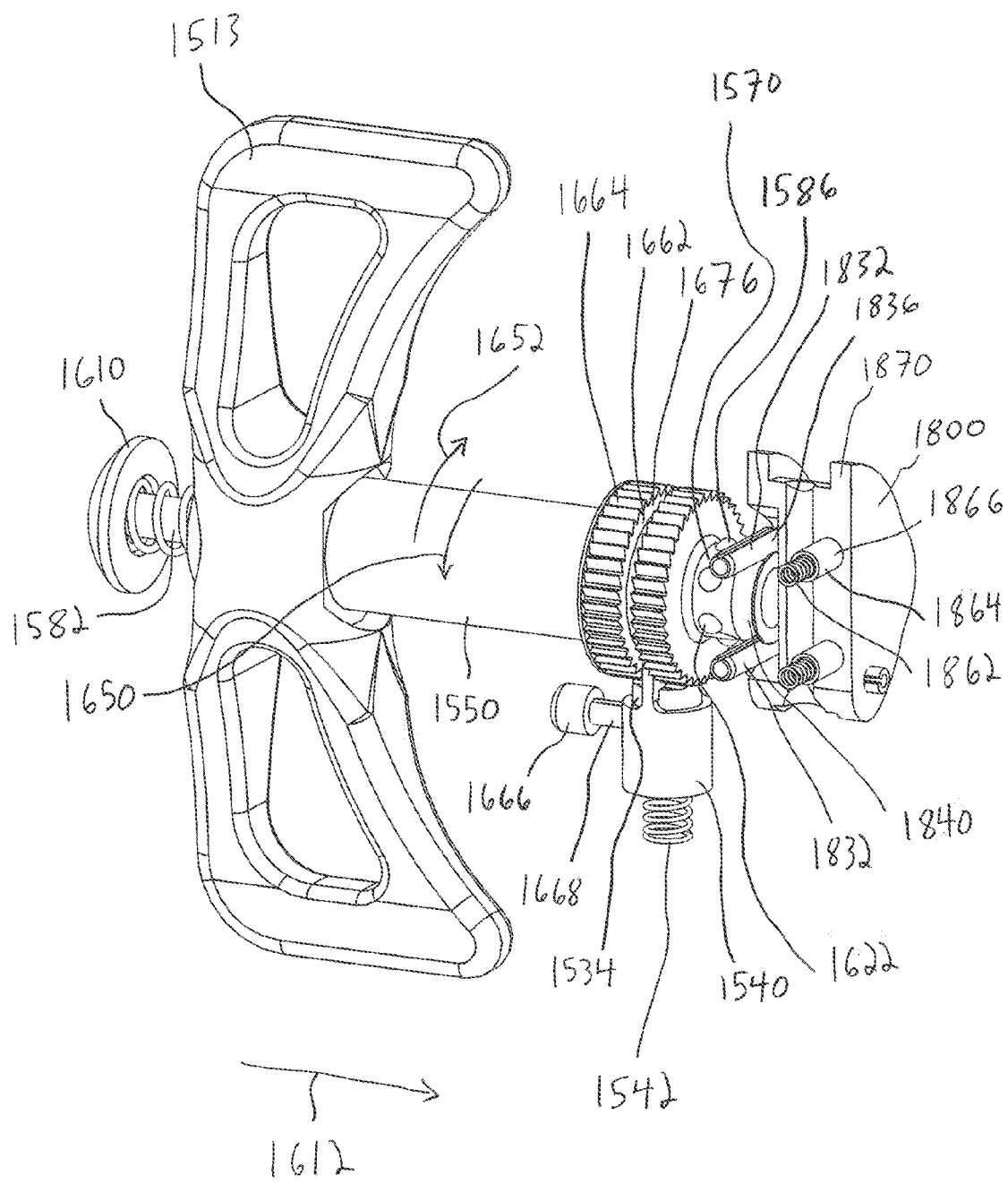
FIG. 55 is a fragmentary view of components of the cable tensioning instrument of FIG. 53 including a drive shaft and a ratchet assembly.

The pawl 1534 of the tensioning instrument 1500 is different than the pawl 884 discussed above because the pawl 1534 is slidably mounted within the pawl sleeve 1540, as shown in FIGS. 54 and 55. Further, the pawl 1534 has a split tooth 1536 with portions disposed on opposite sides of a central fin 1660 of the pawl sleeve 1540 once the pawl 1534 has been positioned within the pawl sleeve 1540, as shown in FIGS. 55 and 61. The fin 1660 fits into a channel 1662 disposed between sets of the teeth 1664 of the drive shaft ratchet portion 1560, as shown in FIG. 55. The engagement of the fin 1660 in the channel 1662 restricts axial movement of the drive shaft 1550 in direction 1612 and maintains the drive shaft 1550 mounted in the body 1502 against a bearing 1663, as shown in FIG. 54. On the other side of the body 1502 from the bearing 1663, the instrument has a nut 1677 that threadingly engages the drive shaft 1550 and further secures the drive shaft 1550 in position on the body 1502.

With reference to FIGS. 55 and 61, the pawl assembly 1532 includes a disassembly button 1666 and a pin 1668 that connects the disassembly button 1666 to the pawl 1534. The pin 1668 extends through a slot 1672 in the body 1502 and through a slot 1670 in the pawl sleeve 1540, as shown in FIG. 61. The body slot 1672 restricts the pin 1668 and pawl 1534 to axial movement up and down within a cavity 1669 of the body 1502 and the engagement of the pin 1668 within the pawl sleeve slot 1670 restricts turning of the sleeve 1540 about the pawl 1534. Thus, both the pawl 1534 and pawl sleeve 1540 are generally restricted to axial, up-and-down movement within the body cavity 1669.

To disassemble the instrument 1500, a user presses the button 1666 in direction 1673 to shift the pin 1668 and pawl 1534 connected thereto in direction 1673 and disengage the pawl tooth 1536 from the drive shaft ratchet teeth 1664. Continued movement of the button 1666 in direction 1673 contacts the pin 1668 against a lower end of the slot 1670 of the pawl sleeve 1540 and shifts the pawl sleeve 1540 in direction 1673 as well. Movement of the pawl sleeve 1540 disengages the fin 1660 from the drive shaft channel 1662 such that both the pawl 1534 and the pawl sleeve 1540 are disengaged from the drive shaft 1550. The handle 1513 can then be moved in direction 1612 (see FIG. 61) to shift the tension drive 1572, clamp body 1800, and drive shaft drive portion 1580 outward from a cavity 1675 of the body 1502, as shown in FIG. 54. In one form, the button 1610 is laser welded to the release shaft 1582 such that the drive shaft 1550 is restricted from being completely removed from the body 1502. In another form, the button 1610 is connected with threads to the release shaft 1582, such that the button 1610 and the nut 1677 can be unthreaded from the release shaft 1610 and the drive shaft 1550, respectively, to permit the drive shaft 1550 and release shaft 1610 to be fully removed from the body 1502, as shown in FIG. 54.

Another advantage of the pawl assembly 1532 is that the pawl 1534 and pawl sleeve 1540 are separate components that independently perform different functions. More specifically, the pawl sleeve 1540 and fin 1660 thereof engage the drive shaft 1550 to restrict axial movement of the drive shaft 1550. The pawl 1534 operates in an orthogonal direction with the pawl tooth 1536 moving up and down as the pawl tooth 1536 travels up and down along the drive shaft ratchet teeth 1664. Thus, the pawl assembly 1532 uses the pawl 1534 and the pawl sleeve 1534 to provide two different functions in a compact package within the instrument 1500.

More specifically, frictional engagement between the pawl sleeve fin 1660 and sidewalls 1676 of the ratchet teeth 1664 (see FIG. 55) may cause the pawl sleeve 1540 to travel axially downward within the cavity 1669 (see FIG. 61) with turning of the drive shaft 1550 in the wind up direction 1650. However, this axial movement of the pawl sleeve 1540 generally does not produce axial movement of the pawl 1534 and disengagement of the pawl tooth 1536 from the drive shaft ratchet teeth 1664. Instead, the pawl sleeve 1540 shifts downwardly along the outer surface of the pawl tooth 1536 toward the distal end 1520 of the instrument 1500. The spring 1542, however, continues to bias the pawl 1534 and tooth 1536 in an opposite direction toward the drive shaft 1550 and into engagement with the drive shaft ratchet teeth 1664 thereof despite any slight axial movements of the pawl sleeve 1540. Thus, the pawl assembly 1532 reduces the likelihood of unintentional disengagement of the pawl 1534 from the drive shaft drive portion 1570.

Figure 57:
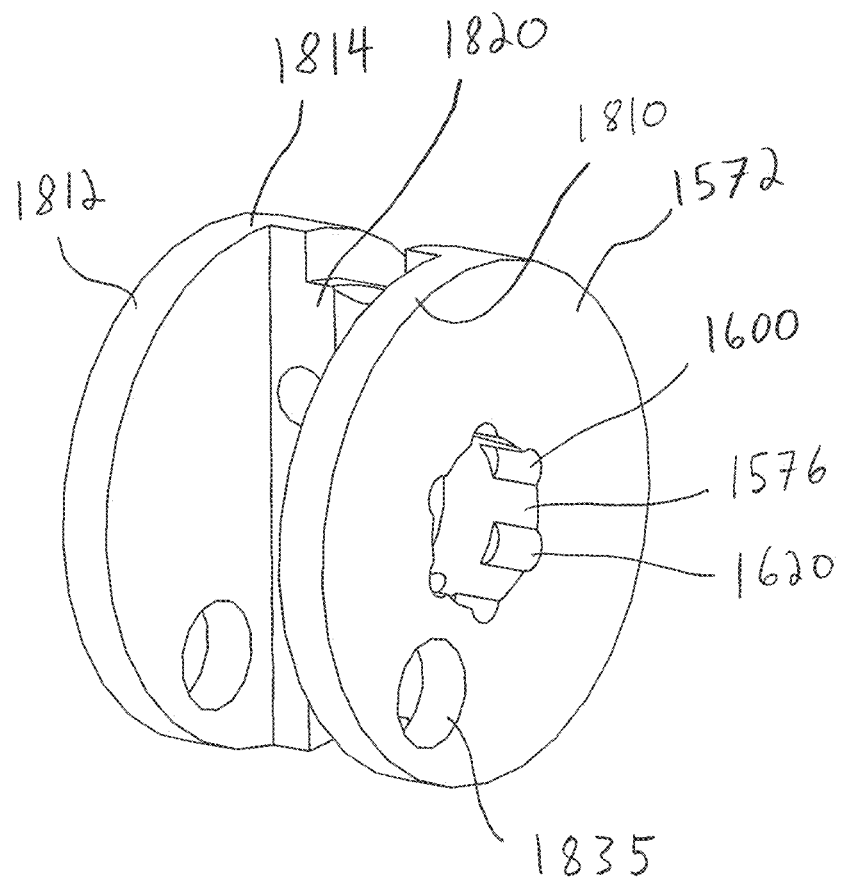
FIG. 57 is a perspective view of a tension drive of the tensioning instrument of FIG. 53 showing a socket that receives a drive portion of the drive shaft.
Figure 58:
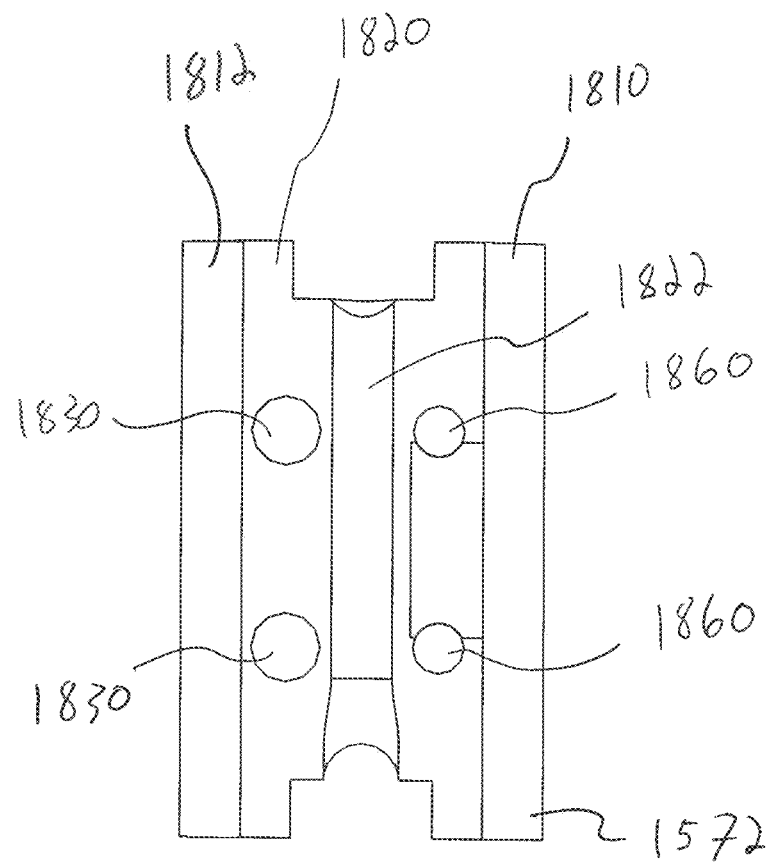
FIG. 58 is an elevational view of the tension drive of FIG. 57 showing a longitudinal groove formed in a face of the tension drive.
Figure 59:
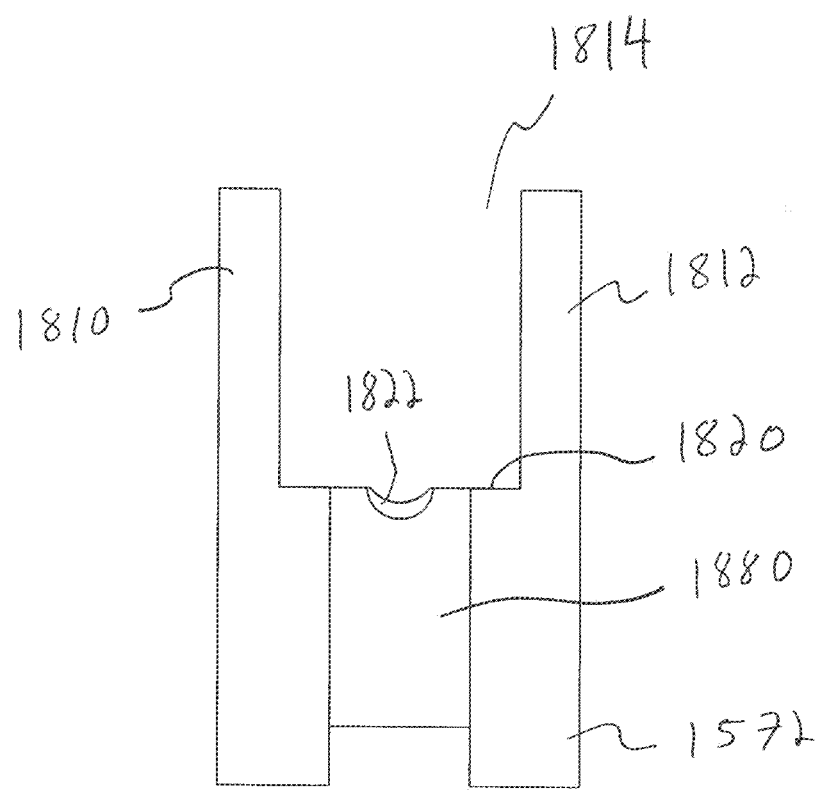
FIG. 59 is a plan view of the tension drive of FIG. 57 showing end plates of the tension drive that define a recess therebetween.
Figure 60:
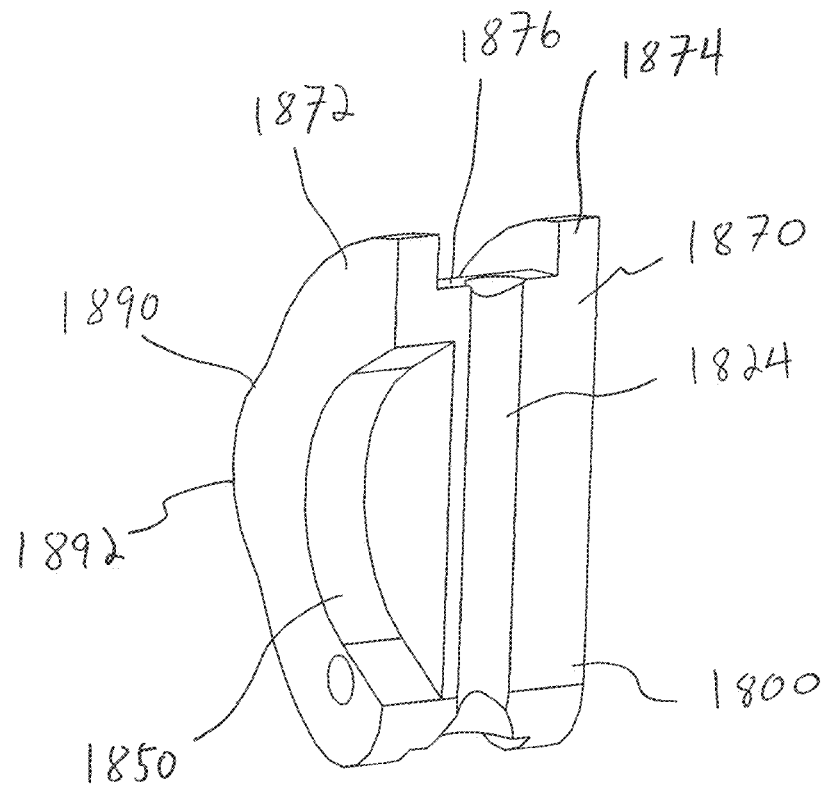
FIG. 60 is a perspective view of a clamp member that is received in the recess of the tension drive, FIG. 60 showing a face of the clamp member and a groove formed therein.

With reference to FIGS. 57-59, the tension drive 1572 has structures that guide and engage the clamp body 1800 during turning of the rotary tensioning device 1510 and reconfiguring of the grip device 1514 from the pass-through configuration to the gripped configuration. In particular, the tension drive 1572 has a drive plate 1810 and an exterior plate 1812 that define a recess 1814 therebetween sized to receive the clamp body 1800 therein, as shown in FIG. 57. The drive plate 1810 has the drive socket 1576 formed therein and the external plate 1812 forms an outer wall of the tensioning instrument 1500 that is visible from the exterior of the tensioning instrument 1500, as shown in FIG. 53. The etch mark 1573 is generally parallel to a groove 1822 of the tension drive 1572 such that the etch mark 1573 is aligned with a through opening 1811 of the grip device 1514 formed by the groove 1822 of the tension drive 1572 and a groove 1824 of the clamp body 1800, as shown in FIGS. 57, 60, and 63. By turning the handle 1513 to align the etch mark 1573 with an etch mark 1813 (see FIG. 53) on the body 1502, the surgeon can visually confirm that the opening 1811 is aligned with a through passage 1823 of the body 1502, as shown in FIG. 63. The cable 24 can then easily be passed into the inlet opening 1522, through the body passage 1823, through the rotary tensioning instrument opening 1811, and outward from the outlet opening 1524.

With reference to FIG. 59, the plates 1810, 1812 may extend from a face 1820 of the tension drive 1572 on opposite sides of the recess 1814. The face 1820 has the cable-receiving groove 1822 formed therein that cooperates with the groove 1824 (see FIG. 60) of the clamp member 1800 to define the through opening 1811 of the grip device 1514, as will be discussed in greater detail below. With reference to FIGS. 54 and 58, the tension drive face 1820 has a pair of blind bores 1830 that receive sliding pins 1832. The pins 1832 have support ends 1834 (see FIG. 54) that are fixed within the blind bores 1830 and free ends 1836 (see FIG. 55) extending outward from the tension drive face 1820 into sliding engagement with a circumferential retention groove 1840 of the drive shaft drive portion 1570, as shown in FIG. 55. The sliding pin free ends 1836 extend generally perpendicular to the length of the drive shaft 1550 and are oriented to fit into the groove 1840 on opposite sides of the drive shaft 1550. With reference to FIG. 60, the clamp member has a recess 1850 that provides clearance for the sliding pin free ends 1836. This clearance permits the clamp member 1800 to move relative to the tension drive 1572 without contacting or interfering with the engagement of the sliding pin 1832 with the drive shaft retention groove 1840. Similarly, the tension drive 1572 has a relatively large opening 1835 that receives a portion of a pin 1837 which extends outward from the clamp body 800. Because the opening 1835 is larger than the pin 1837, the opening 1835 retains the pin 1837 therein while permits the clamp body 1800 to move relative to the tension drive 1572 between the pass through and gripped configurations.

Figure 64:
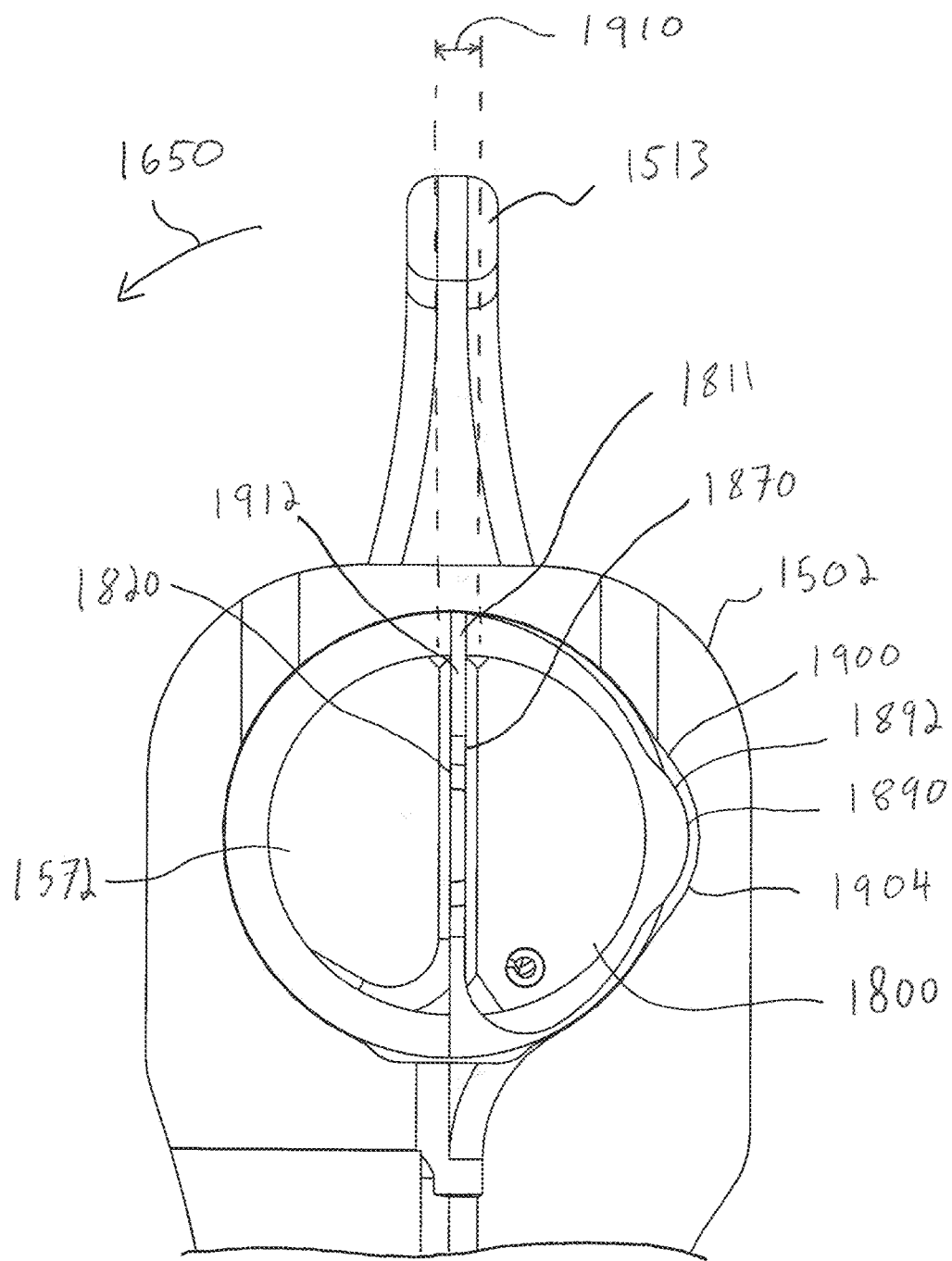
FIG. 64 is an enlarged cross-sectional view similar to FIG. 63 showing a protrusion of the clamp member disposed in a complementary recess of the instrument body.

With reference to FIGS. 55 and 58, the tension drive face 1820 also includes blind bores 1860 that receive springs 1862 and clamp plungers 1864 therein. The clamp plungers 1864 can slide in a piston-like manner within the blind bores 1860 with distal ends 1866 of the clamp plungers 1864 biased by the springs 1862 into engagement with a face 1870 of the clamp body 1800, as shown in FIG. 55. Clamp plungers 1864 operate to separate the clamp body 1800 from the tension drive 1572 once the tension drive 1572 and clamp body 1800 have been turned to a pass through configuration where the tension drive 1572 and clamp body 1800 can move apart, as shown in FIG. 64. During assembly, the clamp plungers 1864 are inserted into the bores 1860 after the springs 1862 and a portion of the tension drive 1572 surrounding the opening of the bores 1860 can be deformed to capture the plungers 1864 and springs 1862 in the bores 1860.

With reference to FIG. 60, the clamp body 1800 has a pair of end walls 1872, 1874 on opposite sides of a curved winding portion 1876. The winding portion 1876 forms a partially discontinuous spool in combination with a winding portion 1880 of the tension drive 1572 (see FIG. 59). The end walls 1872, 1874 of the clamp body 1800 each include a protrusion 1890 having an engagement surface, such as outer curved surface 1892, which is configured to engage a locking surface of the body 1502, such as curved inner surface 1900 of the cavity 1675, as shown in FIG. 63. With the tension drive 1572 and the clamp body 1800 in the pass-through configuration (see FIG. 63), the clamp end wall protrusions 1890 are positioned within a complementary recess 1904 of the body cavity 1902, as shown in FIG. 64. In this orientation, the clamp plungers 1864 can press against the clamp body 1800 and separate the clamp body 1800 from the tension drive 1572 as discussed above. The biasing force of the plungers 1864 against the clamp body 1800 positions the tension drive 1572 and clamp body 1800 so that the rotary tensioning device through opening 1811 has a release or pass-through diameter 1910. As shown in FIG. 64, there is a gap 1912 between the faces 1820, 1870 of the tension drive 1572 and the clamp member 1800 when the tension drive 1572 and the clamp body 1800 are in the pass-through configuration.

Figure 65:
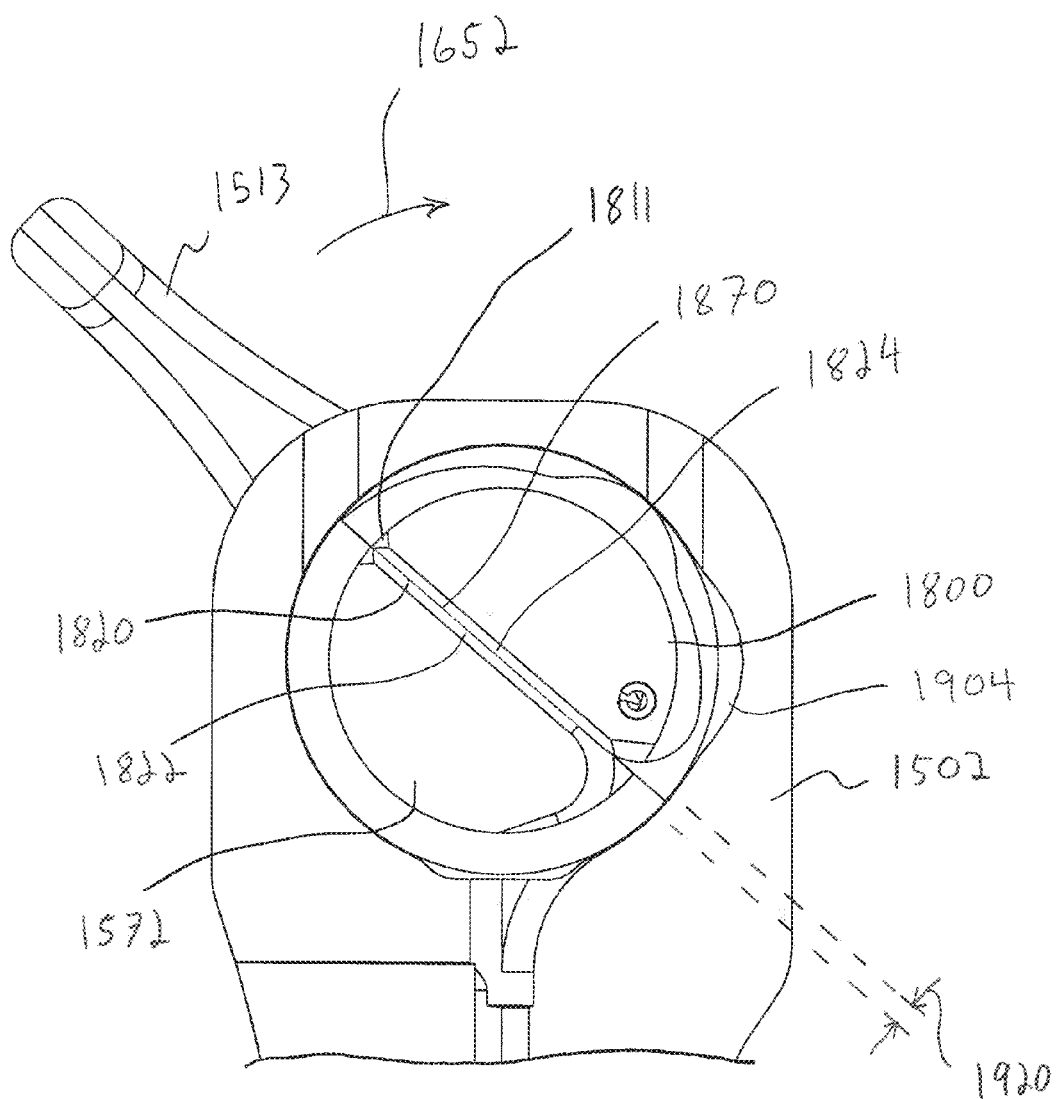
FIG. 65 is a cross-sectional view similar to FIG. 64 showing a handle of the instrument having been turned which moves the clamp member protrusion out of the body recess and into engagement with an inner surface of the body.
Figure 66:
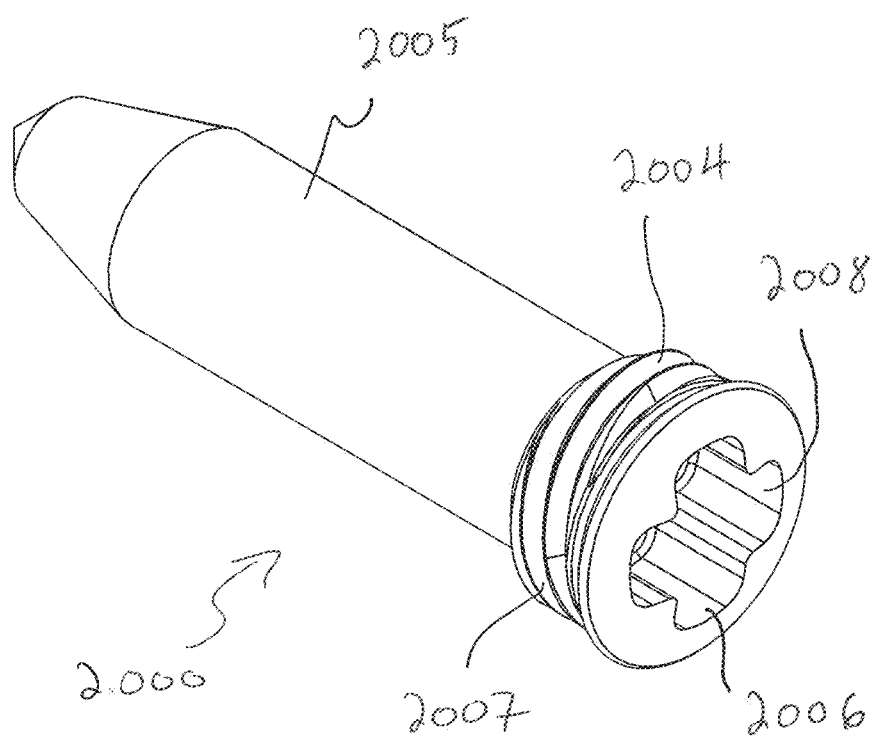
FIG. 66 is a perspective view of a bone anchor having a generally cross-shaped drive recess.
Figure 67:
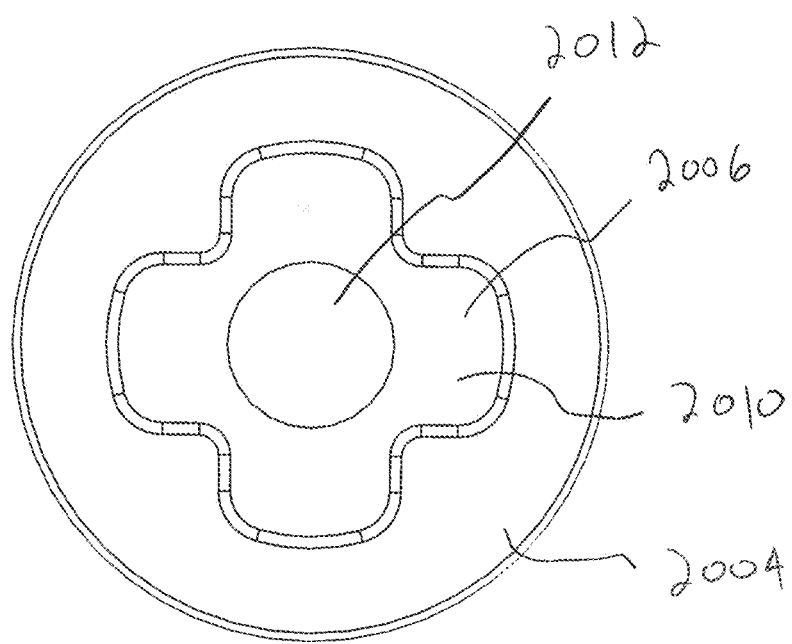
FIG. 67 is a plan view of the bone anchor of FIG. 66 showing features of the drive recess.

Turning the handle 1513 in the wind up direction 1650 brings the protrusion outer surface 1892 into camming engagement with the body inner surface 1900 which shifts the clamp member 1800 toward the face 1820 of the tension drive 1572, as shown in FIG. 65. Thus, turning the handle 1513 in the wind up direction 1650 reconfigures the tension drive 1572 and the clamp body 1800 from the pass-through configuration to the gripped configuration. With reference to FIG. 65, the rotary tensioning device through opening 1811 has an engagement diameter 1920 that is smaller than the pass-through diameter 1910 once the tension drive 1572 and clamp body 1800 have been shifted to the gripped configuration. In particular, the faces 1820, 1870 are brought into engagement with one another and the grooves 1822, 1824 compress the cable 24 therebetween. This fixes the locking clamp member 1800 and tension drive 1572 onto the cable 24. It will be appreciated that the grooves 1822, 1824 may have surface treatments or structures that increase the frictional engagement of the tension drive 1572 and clamp body 1800 with the cable 24.

To release the grip device 1514 from the cable 24, the button 1610 is pressed to shift the release shaft 1582 in direction 1612 (see FIG. 61) and disengage the tension drive 1572 from the drive shaft 1550, as discussed above. The tension in the cable 24 will then turn the tension drive 1572 and the clamp member 1800 back in the pay out direction 1652 which pays out the cable 24 from the winding portions 1876, 1880 of the tension drive 1572 and the clamp member 1800.

With reference to FIGS. 66-69, a bone anchor 2000 and a driver tool distal end 2002 are shown. The bone anchor 2000 and driver tool distal end 2002 are substantially similar to the bone screw 46 and driver 180 discussed above such that the differences from the bone screw 46 and driver 180 will be highlighted. The bone anchor 2000 has a head portion 2004 with a substantially cross-shaped drive recess 2006 with axially extending walls 2008 that extend to a floor 2010 of the recess 2006. The floor 2010 has a blind bore 2012 formed therein. The anchor 2000 has a shank 2005 depending from the head portion 2004. The shank 2005 may be threaded in a complimentary manner to threads 2007 on the head portion 2004.

Figure 68:
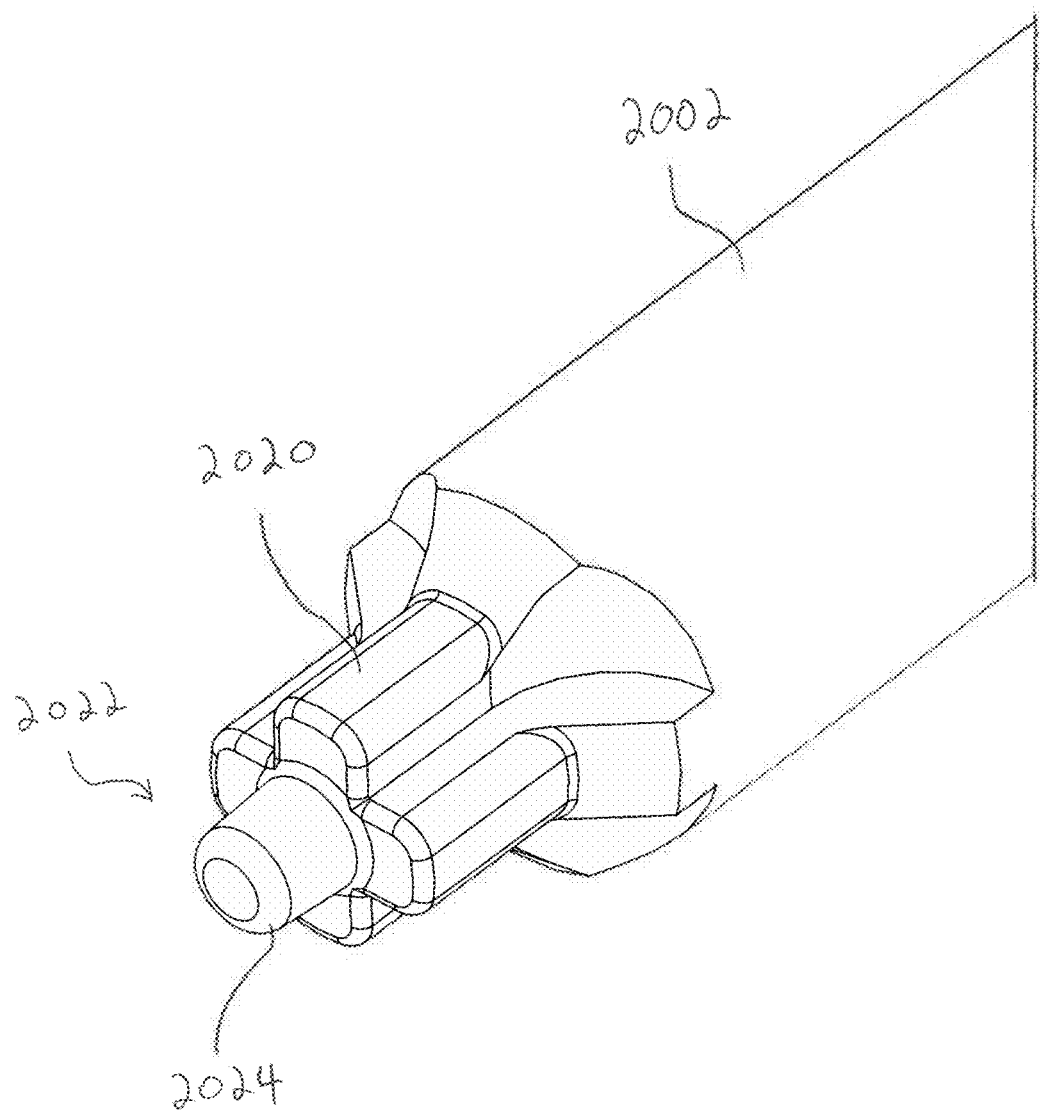
FIG. 68 is a perspective view of a distal end portion of a driver tool for use with the bone anchor of FIG. 66.
Figure 69:
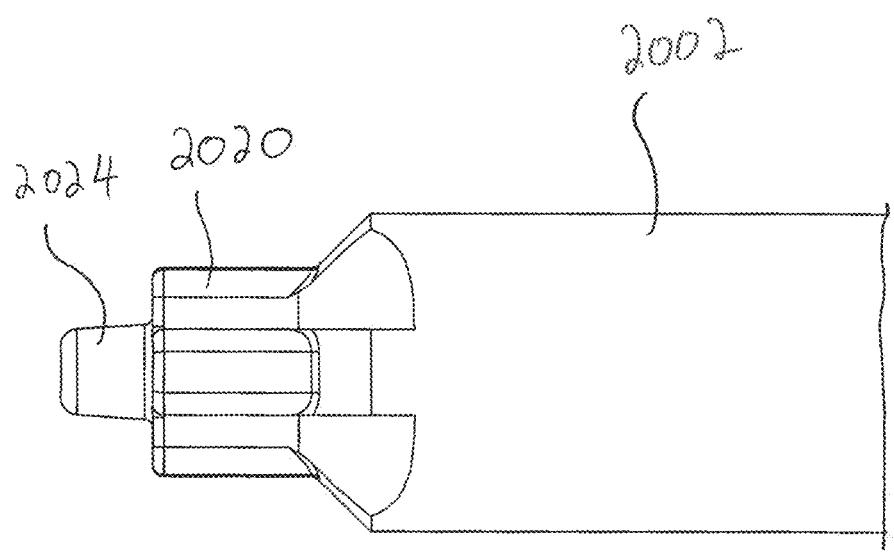
FIG. 69 is an elevational view of the distal end portion of the driver tool of FIG. 68 showing a distal tapered post of the driver tool.

With reference to FIG. 68, the driver distal end 2002 has cross-shaped drives 2020 configured to engage the walls of the drive recess 2006. The distal end 2002 also has a retention device 2022 including a tapered post 2024 which forms a press fit engagement with the blind bore 2012 of the bone anchor 2000.

Those skilled in the art will recognize that a wide variety of modifications, alterations, and combinations can be made with respect to the above described embodiments without departing from the spirit and scope of the invention, and that such modifications, alterations, and combinations, are to be viewed as being within the scope of the invention.

What is claimed is:

1. A bone plate system for stabilizing bone portions, the system comprising:
a bone plate having a longitudinal axis and a pair of opposite bone-engaging surfaces;
a cable configured to be looped around the bone portions and connected to the bone plate;
opposite halves of the bone plate that are laterally spaced from each other and include laterally outer portions defining a maximum lateral width of the bone plate, the bone plate halves being oriented to extend transversely to each other so that one of the bone-engaging surfaces of the bone plate has a generally convex curvature about the longitudinal axis and the other of the bone-engaging surfaces of the bone plate has a generally concave curvature about the longitudinal axis, the bone plate halves being configured for engaging a bone portion on either side of an incision that separates the bone portions;
throughbores of the bone plate halves for receiving bone anchors for anchoring the bone plate halves in engagement with the bone portions, the throughbores including laterally outer throughbores on opposite sides of the bone plate longitudinal axis;
a locking device of the bone plate that interconnects and extends laterally between the spaced bone plate halves and resists relative movement therebetween, the locking device having an unlocked configuration which permits the cable to be shifted relative to the bone plate and a locked configuration which fixes the cable to the bone plate;
a tubular member of the locking device having a through aperture sized to receive the cable therethrough with the aperture having a central axis extending straight through the aperture along which the cable may be advanced with one of the generally convex or concave bone-engaging surfaces of the bone plate positioned against the bone portions;
a pair of longitudinal portions of the bone plate spaced apart by the tubular member and connecting the tubular member to the bone plate halves; and
laterally outer surfaces of the longitudinal portions disposed laterally inward from the outer throughbores of the bone plate halves so that the longitudinal portions have a lateral width thereacross that is less than the maximum lateral width of the bone plate.

2. The bone plate system of claim 1 wherein the tubular member includes deformable portions disposed on opposite sides of the through aperture that are configured to be compressed about the cable and fix the cable to the bone plate.

3. The bone plate system of claim 1 wherein the tubular member through aperture extends from one bone plate longitudinal portion to the other with a substantially constant diameter along the throughbore.

4. The bone plate system of claim 1 wherein the tubular member includes a cylindrical wall extending between the bone plate longitudinal portions with a cylindrical outer surface thereof.

5. The bone plate system of claim 1 wherein the tubular member is uninterrupted such that the tubular member lacks any openings therein that are in communication with the tubular member through aperture.

6. The bone plate system of claim 1 wherein the opposite halves of the bone plate include generally triangular lobes and the bone plate includes a narrowed transverse support connecting the generally triangular lobes of the bone plate halves extending outwardly from the transverse support, the generally triangular lobes having the throughbores disposed therein.

7. The bone plate system of claim 6 wherein the lobes each include a first throughbore adjacent the narrowed transverse support and a second throughbore disposed laterally to the first throughbore and at an oblique angle from the first throughbore relative to the transverse support.

8. The bone plate system of claim 1 wherein the bone plate defines a stop opening and the cable has a leading end portion configured to be advanced through the stop opening and an enlarged, trailing end portion configured to be drawn against the bone plate adjacent the stop opening.

9. The bone plate system of claim 1 wherein the locking device is integrally formed with the spaced bone plate halves.

10. The bone plate system of claim 1 wherein the locking device of the bone plate is configured to receive only one length of the cable, the one length of cable being received in the through aperture of the tubular member.

11. The bone plate system of claim 1 wherein the tubular member of the locking device has an exposed outer surface extending about substantially the entire tubular member and an inner surface extending around the through aperture, the tubular member having a thickness defined between the outer and inner surfaces sized to permit both the tubular member and the cable received in the throughbore to be cut with cutting of the tubular member.

12. The bone plate system of claim 1 wherein the central axis extending straight through the aperture of the locking device tubular member extends substantially perpendicular to the bone plate longitudinal axis.

13. The bone plate system of claim 1 wherein the bone plate halves include lobes having the throughbores therein and the longitudinal portions include a pair of substantially parallel portions at the tubular member and angled portions extending away from the substantially parallel portions that connect the lobes to the substantially parallel portions.

14. The bone plate system of claim 1 wherein each bone plate half includes a pair of longitudinally spaced lobes with two of the throughbores therein and the tubular member is disposed intermediate the pair of lobes along the bone plate.

15. The bone plate system of claim 1 wherein the laterally outer throughbores on opposite sides of the bone plate longitudinal axis include a pair of throughbores in each of the bone plate halves and the pairs of throughbores are on opposite sides of the longitudinal axis from each other.

16. The bone plate system of claim 1 in combination with a plurality of bone anchors, wherein the bone anchors each include a threaded shank.

17. A bone plate system for stabilizing one or more bone portions, the system comprising:
a bone plate having throughbores for receiving bone anchors;
a connector device having a flexible portion for being looped around the one or more bone portions and secured to the bone plate and an end portion for being secured to the bone plate;
longitudinal portions of the bone plate that are laterally spaced from each other;
a deformable member of the bone plate connecting the longitudinal portions and extending transversely thereto, the deformable member having a throughbore configured to receive the flexible portion of the connector device extending therethrough;
exposed opposing crimp portions of the deformable member disposed across the throughbore from one another with the opposing crimp portions being configured to be deformed toward each other and fix the connector device flexible portion to the bone plate; and
a connector device interface of one of the bone plate longitudinal portions adjacent the deformable member, the connector device interface being configured to secure the connector device end portion to the one bone plate longitudinal portion of the bone plate adjacent the deformable member.

18. The bone plate system of claim 17 wherein the deformable member is a cylindrical, tubular member and the crimp portions are diametrically opposed from one another across the throughbore.

19. The bone plate system of claim 17 wherein the deformable member has a sidewall extending about the throughbore that includes the opposing crimp portions and the sidewall has a substantially uniform thickness throughout.

20. The bone plate system of claim 17 wherein the bone plate includes one or more tool-receiving through openings disposed adjacent the deformable member; and
one of the opposing crimp portions of the deformable member extends along one of the one or more tool-receiving through openings such that the one crimp portion is accessible to a tool via the one through opening with the tool received therein.

21. The bone plate system of claim 20 wherein the one tool-receiving through opening has an open-ended configuration with the deformable member of the bone plate defining a portion of the one tool-receiving through opening, the one tool-receiving through opening being open opposite the deformable member.

22. The bone plate system of claim 17 wherein the bone plate includes a pair of tool-receiving through openings disposed on opposite sides of the deformable member; and
one of the opposing crimp portions extends along one of the pair of tool-receiving through openings and the other crimp portion extends along the other of the pair of tool-receiving through openings such that the crimp portions are accessible to a tool via the through openings with the tool received therein.

23. The bone plate system of claim 17 wherein the bone plate has upper and lower surfaces and the opposing crimp portions are disposed between the upper and lower surfaces.

24. The bone plate system of claim 17 wherein the bone plate longitudinal portions include a pair of elongated, spaced tool alignment members connected to the deformable member and extending generally parallel to one another on opposite sides of the deformable member.

25. The bone plate system of claim 17 wherein the bone plate has a longitudinal axis and a pair of opposite bone-engaging surfaces, wherein one of the bone-engaging surfaces has a generally convex curvature about the longitudinal axis and the other of the bone-engaging surfaces has a generally concave curvature about the longitudinal axis.

26. The bone plate system of claim 17 wherein the bone plate has a pair of opposite bone-engaging surfaces that permit the bone plate to be flipped to position either one of the bone-engaging surfaces against the bone portions; and
the throughbores include seating surfaces at both of the bone-engaging surfaces so that the bone anchors can be driven into the throughbores and engaged with the seating surface associated with one bone-engaging surface while the other bone-engaging surface contacts the one or more bone portions.

27. The bone plate system of claim 17 wherein the connector device flexible portion includes a cable.

28. The bone plate system of claim 17 wherein the bone plate includes a pair of opposite bone-engaging surfaces with the throughbores extending between the bone-engaging surfaces; and
retention devices of the bone plate configured to resist back-out of the bone anchors from the bone plate throughbores toward either of the plate bone-engaging surfaces when the other of the plate bone-engaging surfaces is contacting the one or more bone portions.

29. The bone plate system of claim 17 wherein the connector interface includes a stop opening longitudinally offset from the deformable member and extending through the one bone plate longitudinal portion adjacent the deformable member.

30. The bone plate system of claim 17 in combination with a plurality of bone anchors, wherein the bone anchors each included a threaded shank.

31. A bone plate system for stabilizing bone portions, the system comprising:
a plurality of bone screws;
a bone plate having a longitudinal axis:
a cable configured to be looped around the bone portions and connected to the bone plate;
body portions of the bone plate that are laterally spaced from each other and include laterally outer portions defining a maximum lateral width of the bone plate, the bone plate body portions being configured for engaging bone portions on opposite sides of an incision that separates the bone portions;
throughbores of the bone plate body portions for receiving the bone screws, the throughbores including laterally outer throughbores on opposite sides of the bone plate longitudinal axis;
a tubular member of the bone plate that interconnects and extends laterally between the bone plate body portions and resists relative movement therebetween, the tubular member having a through aperture extending laterally through the tubular member and sized to receive the cable therethrough to allow the cable to be looped around the bone portions and advanced through the tubular member, the tubular member having an unlocked configuration which permits the cable to be shifted relative to the bone plate and a locked configuration which fixes the cable to the bone plate;
a pair of longitudinal portions of the bone plate spaced apart by the tubular member and connecting the tubular member to the bone plate body portions; and
laterally outer surfaces of the longitudinal portions disposed laterally inward from the outer throughbores of the bone plate body portions so that the longitudinal portions have a lateral width thereacross that is less than the maximum lateral width of the bone plate.

32. The bone plate system of claim 31 wherein the tubular member includes deformable portions disposed on opposite sides of the through aperture that are configured to be compressed about the cable and fix the cable to the bone plate.

33. The bone plate system of claim 31 wherein the tubular member is uninterrupted such that the tubular member lacks any openings therein that are in communication with the tubular member through aperture.

34. The bone plate system of claim 31 wherein the bone plate includes a transverse support longitudinally spaced from the tubular member and connecting the body portions, the body portions including lobes extending outwardly from the transverse support and having the throughbores disposed therein;
the lobes each include a first throughbore adjacent the transverse support and a second throughbore disposed laterally to the first throughbore and at an oblique angle from the first throughbore relative to the transverse support.

35. The bone plate system of claim 31 wherein the tubular member is integrally formed with the bone plate body portions.

36. The bone plate system of claim 31 wherein the tubular member of the bone plate is configured to receive only one length of the cable, the one length of cable being received in the through aperture of the tubular member.

37. The bone plate system of claim 31 wherein the tubular member has an exposed outer surface extending about substantially the entire tubular member and an inner surface extending around the through aperture, the tubular member having a thickness defined between the outer and inner surfaces sized to permit both the tubular member and the cable received in the throughbore to be cut with cutting of the tubular member.

38. The bone plate system of claim 31 wherein the aperture of the tubular member includes a central axis extending straight through the aperture and extending substantially perpendicular to the bone plate longitudinal axis.

39. The bone plate system of claim 31 wherein the bone plate body portions include lobes having the throughbores therein and the longitudinal portions include a pair of substantially parallel portions at the tubular member and angled portions extending away from the substantially parallel portions that connect the lobes to the substantially parallel portions.

40. The bone plate system of claim 31 wherein each bone plate body portion includes a pair of longitudinally spaced lobes with two of the throughbores therein and the tubular member is disposed intermediate the pair of lobes along the bone plate.

41. The bone plate system of claim 31 wherein the throughbores have a substantially X-shaped arrangement on the bone plate.

42. A bone plate system for stabilizing bone portions, the system comprising:
a bone plate having a longitudinal axis:
a cable configured to be looped around the bone portions and connected to the bone plate;
body portions of the bone plate that are laterally spaced from each other and include laterally outer portions defining a maximum lateral width of the bone plate, the bone plate body portions being configured for engaging bone portions on opposite sides of an incision that separates the bone portions;
throughbores of the bone plate body portions for receiving bone anchors, the throughbores including laterally outer throughbores on opposite sides of the bone plate longitudinal axis;
a locking device of the bone plate that interconnects and extends laterally between the bone plate body portions and resists relative movement therebetween, the locking device having an unlocked configuration which permits the cable to be shifted relative to the bone plate and a locked configuration which fixes the cable to the bone plate;
a tubular member of the locking device having a through aperture sized to receive the cable therethrough;
a pair of longitudinal portions of the bone plate spaced apart by the tubular member and connecting the tubular member to the bone plate body portions;
laterally outer surfaces of the longitudinal portions disposed laterally inward from the outer throughbores of the bone plate body portions so that the longitudinal portions have a lateral width thereacross that is less than the maximum lateral width of the bone plate; and
wherein the bone plate defines a stop opening and the cable has a leading end portion configured to be advanced through the stop opening and an enlarged, trailing end portion configured to be drawn against the bone plate adjacent the stop opening.

43. The bone plate system of claim 42 in combination with a plurality of bone anchors, wherein the bone anchors each include a threaded shank.

44. The bone plate system of claim 42 wherein the tubular member includes deformable portions disposed on opposite sides of the through aperture that are configured to be compressed about the cable and fix the cable to the bone plate.

45. The bone plate system of claim 42 wherein the tubular member is uninterrupted such that the tubular member lacks any openings therein that are in communication with the tubular member through aperture.

46. The bone plate system of claim 42 wherein the bone plate includes a transverse support longitudinally spaced from the tubular member and connecting the body portions, the body portions including lobes extending outwardly from the transverse support and having the throughbores disposed therein;

the lobes each include a first throughbore adjacent the transverse support and a second throughbore disposed laterally to the first throughbore and at an oblique angle from the first throughbore relative to the transverse support.

47. The bone plate system of claim 42 wherein the locking device is monolithically formed with the bone plate body portions.

48. The bone plate system of claim 42 wherein the locking device of the bone plate is configured to receive only one length of the cable, the one length of cable being received in the through aperture of the tubular member.

49. The bone plate system of claim 42 wherein the tubular member of the locking device has an exposed outer surface extending about substantially the entire tubular member and an inner surface extending around the through aperture, the tubular member having a thickness defined between the outer and inner surfaces sized to permit both the tubular member and the cable received in the throughbore to be cut with cutting of the tubular member.

50. The bone plate system of claim 42 wherein the aperture of the tubular member includes a central axis extending straight through the aperture and extending substantially perpendicular to the bone plate longitudinal axis.

51. The bone plate system of claim 42 wherein the bone plate body portions include lobes having the throughbores therein and the longitudinal portions include a pair of substantially parallel portions at the tubular member and angled portions extending away from the substantially parallel portions that connect the lobes to the substantially parallel portions.

52. The bone plate system of claim 42 wherein each bone plate body portion includes a pair of longitudinally spaced lobes with two of the throughbores therein and the tubular member is disposed intermediate the pair of lobes along the bone plate.

53. The bone plate system of claim 42 wherein the throughbores have a substantially X-shaped arrangement on the bone plate.

* * * * *